US007192403B2

(12) United States Patent
Russell

(10) Patent No.: US 7,192,403 B2
(45) Date of Patent: Mar. 20, 2007

(54) METHODS, APPARATUS AND ARTICLES-OF-MANUFACTURE FOR NONINVASIVE MEASUREMENT AND MONITORING OF PERIPHERAL BLOOD FLOW, PERFUSION, CARDIAC OUTPUT BIOPHYSIC STRESS AND CARDIOVASCULAR CONDITION

(76) Inventor: Ted W. Russell, 44 Middle Beach Rd., West, Madison, CT (US) 06443

( * ) Notice: Subject to any disclaimer, the term of this patent is extended or adjusted under 35 U.S.C. 154(b) by 494 days.

(21) Appl. No.: 10/222,564

(22) Filed: Aug. 16, 2002

(65) Prior Publication Data

US 2003/0135124 A1 Jul. 17, 2003

(51) Int. Cl.
*A61B 5/02* (2006.01)
(52) U.S. Cl. ..................................... 600/504; 600/485
(58) Field of Classification Search ................ None
See application file for complete search history.

(56) References Cited

U.S. PATENT DOCUMENTS

| 3,095,872 | A | | 7/1963 | Tolles |
| 3,104,661 | A | | 9/1963 | Halpern |
| 3,132,643 | A | * | 5/1964 | Baum et al. ............. 600/485 |
| 3,920,004 | A | | 11/1975 | Nakayama |
| 4,154,238 | A | | 5/1979 | Link |
| 4,205,688 | A | | 6/1980 | Hauser et al. |
| 4,240,294 | A | | 12/1980 | Grände et al. |
| 4,245,648 | A | | 1/1981 | Trimmer et al. |
| 4,564,020 | A | | 1/1986 | Link |
| 4,649,928 | A | | 3/1987 | Samaras et al. |
| 4,651,747 | A | | 3/1987 | Link |
| 4,664,126 | A | | 5/1987 | Link |
| 4,669,485 | A | | 6/1987 | Russell |
| 4,697,596 | A | | 10/1987 | Link |
| 4,699,151 | A | | 10/1987 | Link |
| 4,699,152 | A | | 10/1987 | Link |

(Continued)

OTHER PUBLICATIONS

C.W. Bryan-Brown, Blood Flow to Organs: Parameters For Function and Survival in Critical Illness, *Critical Care Medicine*, Feb. 1988, pp. 170-178, vol. 16 No. 2.

(Continued)

*Primary Examiner*—Charles A Marmor, II
*Assistant Examiner*—Patricia C Mallari
(74) *Attorney, Agent, or Firm*—David Garrod, Esq.

(57) ABSTRACT

The invention relates to methods, apparatus, articles-of-manufacture, and coded data signals for measuring cardiac output, limb blood flow, perfusion, blood pressure, artery elasticity, and cardiovascular deterioration and disease, including performing these measurements on a continuous heart beat-by-beat basis, for humans and animals. Unlike empirical methods of other noninvasive blood pressure concepts, the invention is grounded on scientifically appropriate hemodynamic principles that studies have validated as accurate, and is practical for wide clinical use. Devices constructed in accordance with the invention can be comfortably employed for numerous applications, including hospital monitoring, physician's office cardiovascular disease management and drug therapy monitoring, home monitoring, and athletic applications.

The invention may be implemented in a variety of single or multi-sensor embodiments, such as: invasive pressure cannula sensor systems; non invasive pressure transducer arrays and piezo or other strain sensing materials that are placed against the skin above arteries; "upstream" pulsing-sensors (that apply single or multi-frequency vibrations that are measured "downstream" from the first placement location); other types of plethysmographic sensors; sonic/ultrasonic/Doppler sensors; MRI blood spin magnetizer/sensors; oxygen sensors; and electrocardiographic sensors, etc.

20 Claims, 42 Drawing Sheets

U.S. PATENT DOCUMENTS

| | | | |
|---|---|---|---|
| 4,712,563 | A | 12/1987 | Link |
| 4,718,426 | A | 1/1988 | Russell |
| 4,718,427 | A | 1/1988 | Russell |
| 4,718,428 | A | 1/1988 | Russell |
| 4,729,382 | A | 3/1988 | Schaffer et al. |
| 4,858,616 | A | 8/1989 | Samaras et al. |
| 5,048,533 | A | 9/1991 | Muz |
| 5,050,613 | A | 9/1991 | Newman et al. |
| 5,099,852 | A | 3/1992 | Meister et al. |
| 5,101,828 | A | 4/1992 | Welkowitz et al. |
| 5,103,828 | A | 4/1992 | Sramek |
| 5,152,296 | A | 10/1992 | Simons |
| 5,152,297 | A | 10/1992 | Meister et al. |
| 5,241,963 | A | 9/1993 | Shankar |
| 5,289,823 | A | 3/1994 | Eckerle |
| 5,301,675 | A | 4/1994 | Tomita et al. |
| 5,423,324 | A | 6/1995 | Tomita |
| 5,626,141 | A | 5/1997 | Takeda |
| 5,724,980 | A | 3/1998 | Nakamura et al. |
| 5,724,981 | A | 3/1998 | Apple |
| 5,730,138 | A * | 3/1998 | Wang .......................... 600/485 |
| 5,743,857 | A | 4/1998 | Shinoda et al. |
| 5,755,229 | A * | 5/1998 | Amano et al. ............... 600/500 |
| 5,876,347 | A | 3/1999 | Chesey et al. |
| 6,117,087 | A | 9/2000 | Kamm et al. |
| 6,280,390 | B1 * | 8/2001 | Akselrod et al. ........... 600/485 |

OTHER PUBLICATIONS

M.E. Safar, et al., Pulsed Doppler: Diameter, Blood Flow Velocity and Volumic Flow of the Brachial Artery in Sustained Essential Hypertension, *Circulation*, Feb. 1981, pp. 393-400, vol. 63 No. 2.
E. Haber, Harvard Medical School Center for Prevention of Cardiovascular Disease, Blood Pressure Key to Fighting Septic Shock, reported in *USA Today*, Sep. 25, 1996.
D. Bates, Harvard Medical School, Study Finds Drug-Reaction Toll Is High, reported in *The Wall Street Journal*, Apr. 15, 1998.
W. Richardson, To Err Is Human: Building a Safer Health System, W.K. Kellogg Foundation Institute of Medicine Committee Report, Dec. 1, 1999.
B.S. Gow, et al., Measurement of Viscoelastic Properties of Arteries in the Living Dog, *Circulation Research*, Jul. 1968, pp. 111-122, vol. 23.
H.R. Warner, et. al., Quantification of beat-by-beat changes in stroke volume from the aortic pulse contour in man, *J. Applied Physiology*, 1953, p. 495, vol. 5 as referred to in D.A. McDonald, *Blood Flow in Arteries*, 1960 pp. 426-428, Arnold Press.
N.T. Kouchoukos, et. al., Estimation of stroke volume in the dog by a pulse contour method, *Circulation Research*, 1970, pp. 611-623, vol. 26 as referred to in D.A. McDonald, *Blood Flow In Arteries*, 1960, pp. 429-430, Arnold Press.
H. Aars, Diameter and Elasticity of the Ascending Aorta During Infusion of Noradrenaline, *Acta Physiol. Scand.*, Mar. 1971, pp. 133-138, vol. 83.
M. Anliker, et al., Transmission Characteristics of Axial Waves in Blood Vessels, *J. Biomechanics*, 1968, pp. 235-246, vol. 1, Pergamon Press, Great Britain.
J. O. Arndt, et al., Mechanics of the Aorta in Vivo. A Radiographic Approach, *Circulation Research*, Jun. 1971, pp. 693-704, vol. 28.
E.O. Attinger et al., Model of the Peripheral Vascular System, *Engineering In Medicine and Biology, Proceedings of the 18th Annual Conference*, 1965, p. 81, vol. 7.
E.O. Attinger et al., Pressure-Flow Relations in Dog Arteries, *Circulation Research*, Aug. 1966, pp. 230-246, vol. 19.
H. Bader, Dependence of Wall Stress in the Human Thoracic Aorta on Age and Pressure, *Circulation Research*, Mar. 1967, pp. 354-361, vol. 20.
G.O. Barnett, The Technique of Estimating Instantaneous Aortic Blood Velocity in Man from the Pressure Gradient, *American Heart J.*, Sep. 1961, pp. 359-366, vol. 62 No. 3.
D.H. Bergel, The Static Elastic Properties of the Arterial Wall, *J. Physiol.*, 1961, pp. 445-457, vol. 156.
D.H. Bergel, The Dynamic Elastic Properties of the Arterial Wall, *J. Physiol.*, pp. 458-469, vol. 156.
D.H. Bergel, Arterial Viscoelasticity, in *Pulsatile Blood Flow*, E.O. Attinger (ed.) 1964, pp. 275-292, McGraw-Hill.
K. Berliner, et al., The Accuracy of Blood Pressure Determinations, A Comparison of Direct and Indirect Measurements, *Cardiologia*, 1960, pp. 118-128, vol. 37 No. 2.
M.A. Biot, *Mechanics of Incremental Deformation*, 1965, pp. 56,72, 82-85, 89-95, J. Wiley, New York.
B. Bodner, et al., Multifactorial Analysis of Mortality and Morbidity in Perforated Peptic Ulcer Disease, *Surgery, Gynecology & Obstetrics*, Oct. 1990, pp. 315-320, vol. 171.
J.M.R. Bruner, et al., Comparison of Direct and Indirect Methods of Measuring Arterial Blood Pressure, Part I, *Medical Instrumentation*, Jan.-Feb. 1981, pp. 1-11, vol. 15 No. 1.
J.M.R. Bruner, et al., Comparison of Direct and Indirect Methods of Measuring Arterial Blood Pressure, Part II, *Medical Instrumentation*, Mar.-Apr. 1981, pp. 12-16, vol. 15 No. 2.
J.M.R. Bruner, et al., Comparison of Direct and Indirect Methods of Measuring Arterial Blood Pressure, Part III, *Medical Instrumentation*, May-Jun. 1981, pp. 17-23, vol. 15 No. 3.
A.C. Burton, Relation of Structure to Function of the Tissues of the Wall of Blood Vessels, *Physiological Reviews*, Oct. 1954, pp. 619-642, vol. 34 No. 4, The American Physiological Society, Inc.
A.C. Burton, *Physiology and Biophysics of the Circulation*, 1965, pp. 76-85, Year Book Medical Publishers, Chicago.
H.R. Butcher and W.T. Newton, The Influence of Age, Arteriosclerosis and Homotransplantation Upon the Elastic Properties of Major Human Arteries, *Annals of Surgery*, Jul. 1958, pp. 1-20, vol. 148 No. 1.
T.E. Carew, et al., Compressibility of the Arterial Wall, *Circulation Research*, Jul. 1968, pp. 61-68, vol. 23.
C.G. Caro et al., Atheroma and Arterial Wall Shear. Observation, Correlation, and Proposal of a Shear Dependent Mass Transfer Mechanism for Atherogenesis, *Proc. Roy. Soc. Lond. B*, 1971, pp. 109-159, vol. 177.
L. A. Cobb et al., External Iliac Vein Flow: Response to Exercise and Relation to Lactate Production, *Journal of Applied Physiology*, May 1969, pp. 606-610, vol. 26 No. 5.
J.N. Cohn, Blood Pressure Measurement in Shock, *JAMA*, Mar. 27, 1967, pp. 972-976, vol. 199 No. 13.
Sir Charles Darwin, John R. Womersley Obituary Tribute, *Nature*, May 3, 1958, p. 1240, vol. 181 No. 461.
R.B. Devereaux and T.G. Pickering, Relationship Between Ambulatory and Exercise Blood Pressure and Cardiac Structure, *American Heart Journal*, Oct. 1988, pp. 1124-1133, vol. 116 No. 4.
P.B. Dobrin and A.A. Rovick, Influence of Vascular Smooth Muscle on Contractile Mechanics and Elasticity of Arteries, *American Journal of Physiology*, Dec. 1969, pp. 1644-1651, vol. 217 No. 6.
W. Feske, et al., Arterial Vascular Compliance Response to Exercise in Hypertension, *Biomedical Sciences Instrumentation*, 1988, pp. 161-165, vol. 24.
W. Feske, et al., Vascular Compliance After Nitroprusside in Hypertension, *IEEE Conf. Proc. 0277*, 1988, pp. 277-280.
S.M. Finkelstein, et al., Vascular Hemodynamic Impedance in Congestive Heart Failure, *American Journal of Cardiology*, Feb. 1985, pp. 423-427, vol. 55.
S.M. Finkelstein, et al., Vascular Compliance in Hypertension, *IEEE Engineering in Medicine & Biology Society 10th Annual Conference Proceedings 0241*, 1988.
D.L. Fry, et al., The Mathematical Approach to Hemodynamics, with Particular Reference to Womersley's Theory, in *Pulsatile Blood Flow*, E.O. Attinger (ed.), 1964, pp. 85-99, McGraw-Hill.
D.L. Fry, et al., In Vivo Studies of Pulsatile Blood Flow: The Relationship of the Pressure Gradient to the Blood Velocity, in *Pulsatile Blood Flow*, E.O. Attinger (ed.), 1964, pp. 101-114, McGraw-Hill.
D.L. Fry, et al., Acute Vascular Endothelial Changes Associated with Increased Blood Velocity Gradients, *Circulation Research*, Feb. 1968, pp. 165-197, vol. 22.

D.L. Fry, Certain Chemorheologic Considerations Regarding the Blood Vascular Interface with Particular Reference to Coronary Artery Disease, *Circulation* (Supplement 4), Nov. 1969, pp. IV38-IV57, vol. 39 & 40.

R.M. Gardner, Direct Blood Pressure Measurement—Dynamic Response Requirements, *Anesthesiology*, Mar. 1981, pp. 227-236, vol. 54 No. 3.

R.M. Gardner, et al., Monitoring Systemic Arterial Blood Pressure: Strip Chart Recording Versus Digital Display, Univ of Utah/LDS Hospital thesis, *Heart & Lung*, publication accepted 1986.

R.M. Gardner, et al., Optimizing the Electrocardiogram and Pressure Monitoring, *Critical Care Medicine*, Jul. 1986, pp. 651-658, vol. 14 No. 7.

L. Goldman, et al., Risks of General Anesthesia and Elective Operation in the Hypertensive Patient, *Anesthesiology*, Apr. 1979, pp. 285-292, vol. 50 No. 4.

B.S. Gow, An Electrical Caliper for Measurement of Pulsatile Arterial Diameter Changes in Vivo, *Journal of Applied Physiology*, 1966, pp. 1122-1126, vol. 21.

B.S. Gow, Viscoelastic Properties of Conduit Arteries, *Circulation Research* (Supplement II), Oct. 1970, pp. 113-122, vol. 26 & 27.

I. Gratz, et al., Continuous Noninvasive Cardiac Output as Estimated from the Pulse Contour Curve, *J. Clin. Monit.*, 1992, pp. 20-27, vol. 8.

J.S. Gravenstein, et al., Sampling Intervals for Clinical Monitoring of Variables During Anesthesia, *J. Clin. Monit.*, Jan. 1989, pp. 17-21, vol. 5 No. 1.

H. Gray, *Gray's Anatomy: Anatomy, Descriptive and Surgical*, T.P. Pick and R. Howden (ed.) of 15th English edition, 1977, pp. 533-538, Bounty Books (div. Of Crown Publishers, Inc.), New York.

J.C. Greenfield, et al., Evaluation of the Pressure Time Derivative Method for Estimating Peak Blood Flow, *American Heart Journal*, Jul. 1962, pp. 101-105, vol. 64 No. 1.

J.C. Greenfield and D.J. Patel, Relation Between Pressure and Diameter in the Ascending Aorta of Man, *Circulation Research*, May 1962, pp. 778-781, vol. 10.

J.C. Greenfield and D.L. Fry, Measurement Errors in Estimating Aortic Blood Velocity by Pressure Gradient, *J. Appl. Pysiol.*, 1962, pp. 1013-1019, vol. 17 No. 6.

J.C. Greenfield and D.L. Fry, A Critique: Relationship of the Time Derivative of Pressure to Blood Flow, *J. Appl. Physiol.*, pp. 1141-1147, vol. 20 No. 6.

J.C. Greenfield and D.L. Fry, Relationship Between Instantaneous Aortic Flow and the Pressure Gradient, *Circulation Research*, Oct. 1965, pp. 340-348, vol. 17.

A.C. Guyton, et al., Evidence for Tissue Oxygen Demand as the Major Factor Causing Autoregulation, *Circulation Research* (Supplement I), Aug. 1964, pp. 60-69, vol. 14 & 15.

A.C. Guyton, *Circulatory Physiology III: Arterial Pressure and Hypertension*, 1980, pp. iii-v, 1-14, 29, 55-56, 85-86, 287-306, 346-353, 357-363, 483-484, 487-496, 506-513, WB Saunders, Philadelphia, PA.

A.C. Guyton, *Textbook of Medical Physiology*, (7th edition), 1986, pp. 272, 278, 295-297, 303-304, 336-346, WB Saunders Co., Philadelphia, PA.

G.M. Haas, Relations Between the Structure of the Aging Aorta and the Properties of Isolated Aortic Elastic Tissue, *Archives of Pathology*, 1943, pp. 29-45, vol. 35.

D.P. Harrington, (Dir. of Medical Engineering @ Tufts-New England Medical Center), Letter of Aug. 1, 1986: Invasive accuracy of 132 monitors at Tufts NE MC: average (all types of) systolic error was 11 mmHg mean with 18 mmHg std dev of diff. Syst std dev est of 3 other hospitals were 16-26 mmHg for ICU/CCU and 12 mmHg for anesth.

D.P. Harrington, Disparities Between Direct and Indirect Arterial Systolic Blood-Pressure Measurements, *CVP*, Aug./Sep. 1978.

G.G. Harrison, Death Due to Anaesthesia at Groote Schuur Hospital, Cape Town—1956-1987, *South African Medical Journal*, Apr. 21, 1990, pp. 416-421, vol. 77.

J. Hildebrandt, Extension of Small-Strain Theory to Finite Deformation of Cylindrical Vessels by Internal Over-Pressure, *Angiologica*, 1970, pp. 257-272, vol. 7.

Invasive accuracy performance letters from: P.A. Burke, (ICU Head Nurse, Northport NY VA MC) Jul. 17, 1986; and N. Claflin (CCN Supervisor and CCN Instructor, Phoenix VA MC) Sep. 1985.

W.B. Jones, et al., An Evaluation of Computed Stroke Volume in Man, *American Heart Journal*, Dec. 1966, pp. 746-750, vol. 72 No. 6.

W.B. Jones, et al., Velocity of Blood Flow and Stroke Volume Obtained from the Pressure Pulse, *J. Clin. Invest.*, 1959, pp. 2087-2090, vol. 38.

W.B. Jones, et al., Comparison of Computed Aortic Blood Velocity with that of Electromagnetic Flowmeter, *J. Appl. Phys.*, 1962, pp. 482-486, vol. 17 No. 3.

W. Kaufman, *Fluid Mechanics*, 1963, pp. 50-54, 141-159, 228-237, McGraw-Hill.

E.S. Katkin, et al., Classical Conditioning of Human Blood Pressure, 1996, in publication; one of several published studies using Continuous Noninvasive Blood Pressure (CNBP) prototype.

R.L. Keenan, et al., Cardiac Arrest Due to Anesthesia: A Study of Incidence and Causes, *JAMA*, Apr. 16, 1985, pp. 2373-2377, vol. 253 No. 16.

J.W. Kennedy, Cardiac Hemodynamics, in *Hemodynamics for Surgeons*, D.E. Strandness, et al., 1975, pp. 47-72, Grune & Stratton, New York.

L.J. Krovetz, et al., Limitation of Correction of Frequency Dependent Artefact in Pressure Recordings Using Harmonic Analysis, *Circulation*, Nov. 1974, pp. 992-997 vol. 50.

L. Laszt and A. Müller, Vergleich der Druckverhältnisse in den Gefässen des Halses und der oberen Extremitäten mit dem Drucke in der Aorta ascendens, *Helv. Physiol. Acta*, 1952, pp. 469-481, vol. 10.

M.G. Learoyd and M.G. Taylor, Alterations with Age in the Viscoelastic Properties of Human Arterial Walls, *Circulation Research*, Mar. 1966, pp. 278-292, vol. 18.

J.M. Levett and R.L. Replogle, Thermodilution Cardiac Output: A Critical Analysis and Review of the Literature, *Journal of Surgical Research*, 1979, pp. 392-404, vol. 27.

R.W. Lieberman, et al., Hemodynamic Predictors of Myocardial Ischemia During Halothane Anesthesia for Coronary-Artery Revascularization, *Anesthesiology*, 1983, pp. 36-41, vol. 59.

R.G. Linford and N.W. Ryan, Pulsatile Flow in Rigid Tubes, *J. Appl. Physiol.*, 1965, pp. 1078-1082, vol. 20 No. 5.

S.C. Ling, et al., Nonlinear Analysis of Aortic Flow in Living Dogs, *Circulation Research*, Aug. 1973, pp. 198-212, vol. 33.

S.C. Ling, et al., Application of Heated-Film Velocity and Shear Probes to Hemodynamic Studies, *Circulation Research*, Dec. 1968, pp. 789-801, vol. 23.

D.A. McDonald, The Relation of Pulsatile Pressure to Flow in Arteries, *J. Physiol.*, 1955, pp. 533-552, vol. 127.

D.A. McDonald, et al., Left Ventricular Output Derived from the Time-derivative and Phase Velocities of the Aortic Pressure Wave, *Medical and Biological Engineering*, Nov. 1973, pp. 678-690, vol. 11.

D.A. McDonald, *Blood Flow in Arteries*, 1974, pp. 118-145, 268, 432-445, Edward Arnold Ltd., London.

F.H. Messerli, Osler's Maneuver, Pseudohypertension, and True Hypertension in the Elderly, *The American Journal of Medicine*, May 1986, pp. 906-910, vol. 80.

V. Mooser, et al., Non-invasive Measurement of Internal Diameter of Peripheral Arteries During the Cardiac Cycle, *Journal of Hypertension*, 1988, pp. S179-S181, vol. 6.

T. Nakashima and J. Tanikawa, A Study of Human Aortic Distensibility with Relation to Atherosclerosis and Aging. *Angiology*, 1971, pp. 477-490, vol. 22.

W.W. Nichols and D.A. McDonald, Wave Velocity in the Proximal Aorta, *Med. & Biol. Engng.*, 1972, pp. 327-335, vol. 10.

M.I.M. Nobel, *The Cardiac Cycle*, 1979, pp. 134-151, 163-209, Blackwell Scientific Public., London.

M.I.M. Nobel, et al., Left Ventricular Filling and Diastolic Pressure-Volume Relations in the Conscious Dog, *Circulation Research*, Feb. 1969, pp. 269-283, vol. 24.

M.I.M. Nobel, et al., Effect of Changing Heart Rate on Cardiovascular Function in the Conscious Dog, *Circulation Research*, Jul. 1966, pp. 206-213 vol. 19.

A. Noordergraaf, Hemodynamics, in *Biological Engineering*, H.P. Schwan (ed), 1969, pp. 391-545, McGraw-Hill, New York.

D.J. Patel, et al., Relation of Radius to Pressure Along the Aorta in Living Dogs, *J. Appl. Physiol.*, 1963, pp. 1111-1117, vol. 18 No. 6.

D.J. Patel, et al., Static Anisotropic Elastic Properties of the Aorta in Living Dogs, *Circulation Research*, Dec. 1969, pp. 765-779, vol. 25.

B.L. Pentecost, The Effect of Exercise on the External Iliac Vein Blood Flow and Local Oxygen Consumption in Normal Subjects, and in those with Occlusive Arterial Disease, *Clin. Sci.*, 1964, pp. 437-445, vol. 27.

L.H. Peterson, et al., Mechanical Properties of Arteries in Vivo, *Circulation Research*, May 1960, pp. 622-639, vol. 8.

L.H. Peterson, Vessel Wall Stress-Strain Relationship, in *Pulsatile Blood Flow*, E.O. Attinger (ed.), 1964, pp. 263-274, McGraw-Hill, New York.

C. Ragan, et al., The Accuracy of Clinical Measurements of Arterial Blood Pressure, With a Note on the Auscultatory Gap, *Bull. Johns Hopkins Hosp.*, 1941, 504-528, vol. 69.

J.K. Raines, et al., A Computer Simulation of Arterial Dynamics in the Human Leg, *J. Biomechanics*, 1974, pp. 77-91, vol. 7.

M. Ramsey, III, Noninvasive Automatic Determination of Mean Arterial Pressure, *Medical & Biological Engineering & Computing*, Jan. 1979, pp. 11-18, vol. 17.

M. Ramsey, III, Noninvasive Blood Pressure Monitoring Methods and Validation, in *Essential Noninvasive Monitoring in Anesthesia*, J.S. Gravenstein, et al. (ed), 1980, pp. 37-51, Grune & Stratton, New York.

J.W. Remington, Physiology of the Aorta and Major Arteries, in *Handbook of Physiology*, W.F. Hamilton (ed.), 1963, pp. 799-838. Sec 2/II.

M.R. Roach, et al., The Effect of Age on the Elasticity of Human Iliac Arteries, *Canadian Journal of Biochemistry and Physiology*, 1959, pp. 557-570, vol. 37.

R. F. Rushmer, Cardiovascular Responses During Exertion, in *Cardiovascular Dynamics*, 1970, pp. 220-243, W.B. Saunders Co., Philadelphia.

K. Sagawa, et al., Static Pressure-Flow Relation in the Total Systemic Vascular Bed of the Dog and its Modification by the Baroreceptor Reflex, *Circulation Research*, Mar. 1975, pp. 406-413, vol. 36.

D.L. Schultz, Pressure and Flow in Large Arteries, in *Cardiovascular Fluid Dynamics-VI*, D.H. Bergel (ed.), 1972, pp. 287-314, Academic Press.

P.A. Steen, et al., Myocardial Reinfarction After Anesthesia and Surgery, *JAMA*, Jun. 16, 1978, pp. 2566-2570, vol. 239 No. 24.

D.E. Strandness and D.S. Sumner, *Hemodynamics for Surgeons*, 1975, pp. 13-20, 163, Grune & Stratton, New York.

M.G. Taylor, Hemodynamics, *Ann. Rev. Physiol.*, 1973, pp. 87-116, vol. 35.

M.G. Taylor, Wave-travel in a Non-uniform Transmission Line, in Relation to Pulses in Arteries, *Phys. Med. Biol.*, 1965, pp. 539-550, vol. 10 No. 4.

M.G. Taylor, The Input Impedance of an Assembly of Randomly Branching Elastic Tubes, *Biophysical Journal*, 1966, pp. 29-51, vol. 6.

M.G. Taylor, Wave Travel in Arteries and the Design of the Cardiovascular System, in *Pulsatile Blood Flow*, E.O. Attinger (ed.), 1964, pp. 343-372, McGraw-Hill, New York.

L. Tiret, et al., Complications Associated with Anaesthesia—a Prospective Survey in France, *Canadian Anaesthetists' Society Journal*, 1986, pp. 336-344, vol. 33 No. 3.

F.H. Van Bergen, et al., Comparison of Indirect and Direct Methods of Measuring Arterial Blood Pressure, *Circulation*, Oct. 1954, pp. 481-490, vol. 10 No. 1.

T.B. Watt, Jr., et al., Arterial Pressure Contour Analysis for Estimating Human Vascular Properties, *J. Appl. Phys.*, Feb. 1976, pp. 171-176, vol. 40 No. 2.

A.M. Weissler, et al., Relationships between Left Ventricular Ejection Time, Stroke Volume, and Heart Rate in Normal Individuals and Patients with Cardiovascular Disease, *Am. Heart J.*, Sep. 1961, pp. 367-378, vol. 62 No. 3.

J.P. Welch and P.J. Martin, Hemodynamic Monitoring Signal Processing Report, Dec. 1, 1985.

N. Westerhof, et al., Comparison of an Electrical Model of the Human Systemic Arterial Tree with Measurements in Humans, *Proceedings of the 18th Annual Conference of Engineering in Medicine and Biology*, 1965, p. 35, vol. 7.

C.J. Wiggers, et al., Active Changes in Size and Distensibility of the Aorta During Acute Hypertension, *Am. J. Physiol.*, 1938, pp. 603-611, vol. 124.

K. Witzig, Über erzwungene Wellenbewegungen zäher, inkompressibler Flüssigkkeiten in elastischen Röhren, Inaugural-Dissertation, 1914, Bern: Wyss.

J.R. Womersley, Method for the Calculation of Velocity, Rate of Flow and Viscous Drag in Arteries When the Pressure Gradient is Known, *J. Physiol.*, 1955, pp. 553-563, vol. 127.

J.R. Womersley, Oscillatory Flow in Arteries: The Constrained Elastic Tube as a Model of Arterial Flow and Pulse Transmission, *Phys. in Med. Biol.*, 1957, pp. 178-187, vol. 2.

J.R. Womersley, An Elastic Tube Theory of Pulse Transmission and Oscillatory Flow in Mammalian Arteries, 1957, Wright Air Development Center Technical Report WADC TR 56-614.

J.R. Womersley, Oscillatory Flow in Arteries: Effect of Radial Variation in Viscosity on Rate of Flow, *Proceedings of the Physiological Society*, Dec. 1954, pp. 38P-39P, vol. 127.

J. Zvargulis (Clinical Professor of Anesthesiology, Jefferson Medical College), Invasive accuracy performance letter, Jul. 1986.

F.H. Newman and V.H.L. Searle, *The General Properties of Matter* (5th edition), 1957, pp. 363-380, Edward Arnold, London.

J.R. Brobeck (ed), *Best & Taylor's Physiological Basis of Medical Practice* (9th edition), 1973, pp. 3.151, 3.196, The Williams & Wilkins Co., Baltimore.

D.P. Harrington, Three-way long term continuous monitoring clinical comparison—invasive and nurse versus Cor7000. Tufts NE MC study of 17 ICU/recovery subjects; avg duration of 5.5 hrs (2-10 hr range) with an avg of 1.5 recals per subject; results: 3/0 mmHg sys/dia A-line-CNBP mean diff., Completed Apr. 15, 1988.

Two independent hospital three-way predecessor CNBP accuracy studies performed pursuant to FDA PMA guidelines, From Cor Medical Model 7000 Clinical Accuracy Report, 1992.

A.E.H. Love, *A Treatise on the Mathematical Theory of Elasticity* (4th edition), 1927, Cambridge University Press, London.

D.L. Fry, Certain Aspects of Hydrodynamics as Applied to the Living Cardiovascular System, *IRE Transactions on Medical Electronics*, Dec. 1959, pp. 252-259, vol. ME-6.

D.L. Fry, Measurement of Pulsatile Blood Flow by the Computed Pressure Gradient Technique, *IRE Transactions on Medical Electronics*, Dec. 1959, pp. 259-264, vol. ME-6.

T.B. Levine, et al., Regional Blood Flow Supply and Demand in Heart Failure, *American Heart Journal*, Dec. 1990, pp. 1547-1551, vol. 120 No. 6 Part 2.

A.C. Guyton, *Textbook of Medial Physiology* (7th edition), 1986, pp. 277 (Figure 23-5), W.B. Saunders Co., Philadelphia, PA.

G.W. Roach, Adverse Cerebral Outcomes After Coronary Bypass Surgery, *New England Journal of Medicine*, Dec. 19, 1996, vol. 335 No. 25.

D. Lawson, et al., Blood Flow Limits and Pulse Oximeter Signal Detection, *Anesthesiology*, Oct. 1987, pp. 599-603, vol. 67 No. 4.

G.L. Duff, Experimental Cholesterol Arteriosclerosis and its Relationship to Human Arteriosclerosis, *Archives of Pathology*, 1935, pp. 81-123, 259-304, vol. 20.

R. Winslow, Heart-Disease Sleuths Identify Prime Suspect: Inflammation of Artery, as reported in *The Wall Street Journal*, Oct. 7, 1999.

L.J. Launer, et al., The Association Between Midlife Blood Pressure Levels and Late-Life Cognitive Function: The Honolulu-Asia Aging Study, *JAMA*, 1995, pp. 1846-1851, vol. 274.

N.O. Borhani, et al., Final Outcome Results of the Multicenter Isradipine Diuretic Atherosclerosis Study (MIDAS): A Randomized Controlled Trial, *JAMA*, Sep. 11, 1996, pp. 785-791, vol. 276 No. 10.

Editorial from the Authors of JAMA, Calcium Channel Blockers, Lessons Learned from MIDAS and Other Clinical Trials, *JAMA*, Sep. 11, 1996, pp. 829-830, vol. 276 No. 10.

S.D. Moore and R. Winslow, Roche Recalls Drug to Reduce Blood Pressure, as reported in *The Wall Street Journal*, Jun. 9, 1998.

Dow Jones Newswires, Pfizer Faces Lawsuit Over Alleged Risks of Hypertension Drug, as reported in *The Wall Street Journal*, May 31, 2000.

V.L. Streeter, et al., Energy Dissipation in Pulsatile Flow Through Distensible Tapered Vessels, in *Pulsatile Blood Flow*, E.O. Attinger (ed.), 1964, pp. 149-177, McGraw-Hill, New York.

* cited by examiner continued from FIG. 8

Using the previously-determined $O_p$ and $O_{ra}$ shift factors, determine systolic pressure, $S_i$, using a radius of $R_{s_i} = R_{a_i} + \Delta_i/2$, and for the equations:

$$S_i = 119 + O_p + \frac{e^{50.7(R_{s_i} - 0.2145 + O_{ra})}}{0.195} \qquad S_i > 200 \; mmHg$$

$$S_i = 49 + O_p + \frac{e^{50.7(R_{s_i} - 0.2145 + O_{ra})}}{0.105} \qquad 60 < S_i \le 200 \; mmHg$$

$$S_i = \left[\frac{1.8}{60 + O_p}\right] \times e^{50.7(R_{s_i} - 0.2145 + O_{ra})} \qquad S_i \le 60 \; mmHg$$

— 809

Using the previously-determined $O_p$ and $O_{ra}$ shift factors, determine mean pressure, $M_i$, using a radius of $R_{m_i} = R_{a_i} - \Delta_i/2 + \Delta_{mean_i}$, and for the equations:

$$M_i = 119 + O_p + \frac{e^{50.7(R_{m_i} - 0.2145 + O_{ra})}}{0.195} \qquad M_i > 200 \; mmHg$$

$$M_i = 49 + O_p + \frac{e^{50.7(R_{m_i} - 0.2145 + O_{ra})}}{0.105} \qquad 60 < M_i \le 200 \; mmHg$$

$$M_i = \left[\frac{1.8}{60 + O_p}\right] \times e^{50.7(R_{m_i} - 0.2145 + O_{ra})} \qquad M_i \le 60 \; mmHg$$

— 810

The blood pressure sample waveform for heart beat cycle i is converted from radial displacement samples using the relationship below, which is depicted in FIG. 27:

$$\hat{p}_i(t) \; for \; M = \left[\frac{M_i - D_i}{\Delta_{mean_i}}\right] x_i(t) + D_i$$

$$\hat{p}_i(t) \; for \; S = \left[\frac{S_i - M_i}{\Delta_i - \Delta_{mean_i}}\right] x_i(t) + M_i$$

— 811

Compute and display with trace, three-beat averages of diastolic pressure, mean pressure, systolic pressure and rate.

— 812

800, cont.

*FIG. 9* continued from FIG. 10

Compute Womersley phase factors, $e'_{10}$, for at least the first three harmonic frequency components, $f_H$, using the approximative formula:

$$\left[e'_{10}\ (rad)\right]_H = \frac{\sqrt{2}}{[\alpha]_H} + \frac{1}{[\alpha]_H^2} + \frac{19}{24\sqrt{2} \times [\alpha]_H^3}$$

More precisely computed tabular Womersley values are in D.A. McDonald, *Blood Flow in Arteries*. Arnold Press (1960).

— 905

Compute a group propagation velocity (for a non-viscous fluid), $c'_o$, in accordance with the formula:

$$c'_o = \sqrt{\frac{[\bar{E}_{yf}]_3 \cdot (2-\gamma)}{3\rho}} \quad \text{or} \quad \approx \sqrt{\frac{2\,[\bar{E}_{yf}]_3\,h}{3\rho R_a}}$$

where $$\langle \bar{E}_{yf} \rangle_3 = \frac{E_{yf,i-1} + E_{yf,i-2} + E_{yf,i-3}}{3} \quad \text{represents}$$

a moving average of the last three composite, flow-based elasticity values. (Alternatively, or for the initial approximation pass, e.g., before $E_{yf}$ is computed, the time-domain computed incremental elasticity, $E_{inc}$, is used).

— 906

Compute, for beat cycle i, a first-pass pressure-gradient sample waveform, $\nabla p_i(t)$, in accordance with the formula:

$$\nabla p_i(t) = \frac{SR \cdot Z_{cal}}{c'_o} \cdot \left[(\hat{p}_i(t) - \hat{p}_i(t - \frac{1}{SR})\right]$$

where $Z_{cal}$ represents a sampling length, initially assumed to be 2 cm, and subsequently adjusted, if necessary, to match time-domain and frequency-domain elasticities. A pressure gradient waveform is shown in FIG. 21.

FIG. 11 continued from FIG. 12

Compute, for heart beat i, a first-pass pressure-flow phase lag, $\phi_N$, for at least the first three harmonic frequencies, $f_H$, with a "normalization process" that computes a plurality of phase-shifted flow waveforms, $[[V_i(t)]_H]_{-\phi}$, and, for each harmonic frequency, determining the minimum amount of phase shift, $\phi = [\phi_N]_H$, that produces a simultaneous peaking of the pressure waveform, $[\bar{p}_i(t)]_H$, and the flow-based elasticity waveform, $[E_{vf_i}(t)]_H$, where:

$$[E_{yf_i}(t)]_H = \frac{[\bar{p}_i(t)]_H^2}{[[V_i(t)]_H]_{-\phi}^2} \left[\frac{3}{\gamma_i(2-\gamma_i)\rho}\right]\left[\frac{1}{[\Delta C_{a_i}]_H^2}\right]$$

and $$[V_i(t)]_H = \left[\frac{R_{a_i}^2 \cdot [M_{zp_i}]_H}{\mu}\right]\left[\frac{[\dot{M}_{\cdot_i}]_H}{[\alpha]_H^2}\right] \times$$
$$\sin(2\pi f_H t - [\phi_{zp_i}]_H + [\dot{e}_{\cdot 0}]_H)$$

and where interpolation is used to determine the precise pressure-flow phase lag, $[\phi_N]_H$, for each harmonic frequency, $f_H$.

— 911

For the samples in beat cycle i, determine the time, $t_{\bar{p}_i\_max}$, at which the blood pressure waveform, $\bar{p}_i(t)$, exhibits its maximum value.

— 912

Compute at least the first three FFT components of the $\bar{p}_i(t)$ converted pressure waveform, i, such that:

$$\bar{p}_i(t) = \sum_H [M_{\bar{p}_i}]_H \cos(2\pi f_H t - [\phi_{\bar{p}_i}]_H)$$

where $M_{\bar{p}_i}$ and $\phi_{\bar{p}_i}$ represent the magnitude and phase, respectively, of the i$^{th}$ beat pressure waveform

FIG. 13 from FIG. 14

Determine, for beat cycle i, the final-pass harmonic components of flow velocity, $\left[\hat{V}_i(t)\right]_H$, for at least the first three harmonic frequencies, $f_H$, in accordance with the formula:

$$\left[\hat{V}_i(t)\right]_H = \left[\frac{R_{ai}^2 \cdot [M_{\nabla p_i}]_H}{\mu}\right]\left[\frac{[\dot{M}_{10}]_H}{[\alpha]_H^2}\right] \times \sin(2\pi f_H t - [\phi_{\nabla p_i}]_H + [\dot{e}_{10}]_H)$$

where $M_{\nabla p_i}$ and $\phi_{\nabla p_i}$ represent the magnitude and phase, respectively, of the frequency components of the $i^{th}$ beat, final-pass pressure-gradient waveform, such that:

$$\nabla \vec{p}_i(t) = \sum_H \left[M_{\nabla p_i}\right]_H \cos(2\pi f_H \times t - \left[\phi_{\nabla p_i}\right]_H)$$

— 918

900, cont.

Using the first-pass pressure-flow phase lag values, $[\phi_{N_i}]_H$, to provide a phase lag-corrected flow waveform, $\vec{P}_i(t)$, determine the peak flow sample, $t_{\vec{p}\_\text{max}}$, for beat cycle i, where:

$$\hat{V}_i(t) = \sum_H \left[\left[\hat{V}_i(t)\right]_H\right]_{-[\psi_{N_i}]_H}$$

$$= \sum_H \left[\frac{R_{ai}^2 \cdot [M_{\nabla p_i}]_H}{\mu}\right]\left[\frac{[\dot{M}_{10}]_H}{[\alpha]_H^2}\right] \sin(2\pi f_H t - [\phi_{\nabla p_i}]_H + [\dot{e}_{10}]_H)$$

— 919 continued on FIG. 16

*FIG. 15* continued from FIG. 15

Compute, for beat cycle i, a final-pass pressure-flow phase lag, $\vec{\phi}_N$, for at least the first three harmonic frequencies, $f_H$, with a "normalization process" that computes a plurality of phase-shifted, final-pass flow waveforms, $\left[[\vec{V}(t)]_H\right]_{\to \phi}$, and, for each harmonic frequency, determining the minimum amount of phase shift, $\phi = [\vec{\phi}_N]_H$, that produces a simultaneous peaking of the pressure waveform, $[\vec{p}_i(t)]_H$, and the final-pass, flow-based elasticity waveform, $[\vec{E}_{yf_i}(t)]_H$, where:

$$[\hat{E}_{yf_i}(t)]_H = \frac{[\hat{p}_i(t)]_H^2}{\left[[\hat{V}_i(t)]_H\right]_{\to \phi}^2}\left[\frac{3}{\gamma_i(2-\gamma_i)\rho}\right]\left[\frac{1}{[\Delta \hat{C}_{i_i}]_H^2}\right]$$

and $$[\hat{V}_i(t)]_H = \left[\frac{R_{a_i}^2 \cdot [M_p]_H}{\mu}\right]\left[\frac{[\dot{M}_{1v}]_H}{[a]_i^*}\right]\sin(2\pi f_n t - [\phi_p]_H + [\dot{e}_{i0}]_H)$$

and where interpolation is used to determine the precise pressure-flow phase lag, $[\phi_N]_H$, for each harmonic frequency, $f_H$.

⎯ 920

900, cont.

Determine the $i^{th}$ beat brachial mean flow velocity by summing harmonic components and computing the average sample of the velocity waveform, with: $V_{\text{brachmv}} = \frac{HR}{60 \cdot SR} \sum_{\text{over HR}} \sum_H [\hat{V}_i(t)]_H$

⎯ 921

Determine a final-pass composite, flow-based elasticity, using: $\vec{E}_{yf_i} = \sum_H \left[\vec{E}_{yf_i}(t_{\vec{p}\_\max})\right]_H$

⎯ 922

Composite pressure and flow waveforms are averaged over a running multi-beat sequence of 3-6 beats approximately, for display:

$$\langle \vec{p}(t) \rangle_6 = \frac{1}{6} \sum_{\substack{6-\text{beat} \\ \text{phase-3 cal}}} \vec{p}_i(t) \qquad \langle \vec{V}(t) \rangle_6 = \frac{1}{6} \sum_{\substack{6-\text{beat} \\ \text{phase-3 cal}}} \vec{V}_i(t)$$

where the notation $\langle \rangle_6$ denotes the average waveform contour.

⎯ 923 continued on FIG. 17

FIG. 16 continued from FIG. 18a – <u>Two-point Flow Monitoring</u>

Compute at least the first three FFT components of the $\hat{p}_R(t)$ and $\hat{p}_D(t)$ converted $i^{th}$ heart beat pressure waveforms, such that:

$$\hat{p}_R(t) = \sum_H [M_{\hat{p}_P}]_{i,H} \cos(2\pi f_H t - [\varphi_{\hat{p}_P}]_{i,H})$$

$$\hat{p}_D(t) = \sum_H [M_{\hat{p}_D}]_{i,H} \cos(2\pi f_H t - [\varphi_{\hat{p}_D}]_{i,H})$$

where $M_{\hat{p}_P}$ and $M_{\hat{p}_D}$ are the magnitude, and $\varphi_{\hat{p}_P}$ and $\varphi_{\hat{p}_D}$ are the phase, respectively, of the $i^{th}$ beat pressure waveform — 958

Compute $\Delta\varphi$ phase shift for each corresponding harmonic pair of the computed FFT components of the converted $i^{th}$ heart beat pressure waveforms, $\hat{p}_R(t)$ and $\hat{p}_D(t)$, with: $[\Delta\varphi_{\hat{p}_P}]_{i,H} = [\varphi_{\hat{p}_D} - \varphi_{\hat{p}_P}]_{i,H}$ — 959

The apparent phase velocity of each harmonic component between the two sensors is computed at right, whereby $\omega$ is equal to $2\pi f$.

$$[c'_{i,H}] = \frac{\omega_H \cdot \Delta z}{[\Delta\varphi_{\hat{p}_P}]_{i,H}}$$

— 960

950, cont.

Derive the $i^{th}$ blood flow waveform, $[\hat{Q}_{P_i}(t)]_H$, as a summation of at least the first three harmonic flow components in accordance with the formula:

$$\hat{Q}_{P_i}(t) = \sum_H \left[\frac{\pi R_{a i}^2 \cdot [M_{\hat{p}_P}]_{i,H}}{\omega_H}\right] \left[\frac{\Delta\varphi_{\hat{p}_P} \cdot [\dot{M}_{10}]_{i,H}}{\Delta z}\right] \times$$

$$\sin(2\pi f_H t - [\phi_{\hat{p}_P}]_{i,H} + [\dot{e}_{10}]_{i,H} + \pi/2)$$

— 961 where $\dot{M}_{\nabla \hat{p}_P}$ and $\varphi_{\nabla \hat{p}_P}$ are the magnitude and phase, respectively, of the frequency components of the dp/dz pressure gradient waveform at the proximal sensor, which is:

$$\nabla \hat{p}_P(t) = \sum_H |\frac{\omega_H \cdot M_{\hat{p}_P}}{c'_{i,H}}|_{i,H} \cos(2\pi f_H t - [\varphi_{\hat{p}_P}]_{i,H} + \pi/2)$$

and where $M'_{10}$ and $e'_{10}$ are determined by processes 903-905, and forward flow is computed similar to processes 932-934.

*FIG. 18b*

ELEVATED FLOW CUFF MEASUREMENT ERROR

[ View of Cuff-Constricted Artery, Pulsed Open]

$$p_s = \frac{\rho}{2}\left[V_m\left[1 - \frac{r_0^2}{R_n^2}(2 - 2y + y^2)\right]\right]^2 \quad \text{with:} \quad y = \frac{r_p}{R_n - 01\left[\frac{R_n - r_p}{R_n}\right]}$$

FLOW-BASED ELASTICITY    FIG. 29

FIG. 29a-c from the McDonald-Womersley flow tech...

Womersley's work extends Poiseuille steady-state flow concepts to oscillatory flows. Flow velocity profiles and parameters are determined by Womersley Bessel function differential equation solutions. This applies Newtonian Navier-Stokes equations of motion, which adds effects of fluidic shear stresses of viscous fluids to Euler motion equations.

FIG. 29a - Flow waveforms are harmonic pressure gradient, blood inertia and viscosity effects:

Forward flow (darkened part lower graph) is propelled by about 1/8th of the pressure gradient dp/dz (right) that precedes the propagating pressure waveform (both graphs). Harmonic Q flows are computed solely from externally estimated radius and dp/dz. Flow phase effects of blood viscosity, inertia, lumen size, and wall mass-constraint are applied with Womersley-computed Bessel moduli $M'_{10}$ and phase $e'_{10}$ functions of $\alpha$, which CNH computes with the Womersley estimators:

$$\alpha = R\sqrt{\omega/\nu}, \quad M_{10} = 1 - \frac{\sqrt{2}}{\alpha} - \frac{1}{\alpha^2}, \quad e_{10}(rad) = \frac{\sqrt{2}}{\alpha} - \frac{1}{\alpha^2} - \frac{19}{24\sqrt{2}\alpha^3}$$

$\nu$ is kinematic viscosity $\eta/\rho$, $\rho$ is blood density (1.05 gm/cm³); $\phi = \tan^{-1}A/B$;
$M$ is pressure gradient modulus $\sqrt{A^2+B^2}$ of real [Mcos$\phi$] & imaginary [Msin$\phi$] parts.

And flow waveforms are FFT-computed by: $\dot{Q} = \left[\frac{\pi R^4 M}{\mu}\right]\left[\frac{M'_{10}}{\alpha^2}\right] \sin(\omega t - \phi - e_{10})$ McDonald's aorta gradient was from phase velocities (C) computed from pressure differences between two invasive sites 4 cm apart with:

$$dp/dz = -\frac{1}{C}\frac{dP}{dt} = M\cos(\omega t - \phi) \text{ with } C = \frac{\omega \cdot \Delta z}{\Delta \phi}$$

McDonald's large study had exceptional accuracy:
(.97 correlation) with extreme cardiac and vasoactive stimulations (APPENDIX I-M)

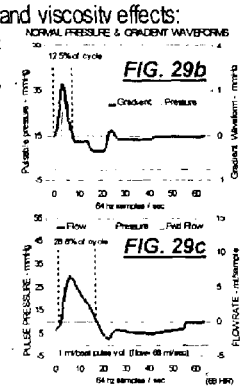

FIG. 29d-h the invented flow-based elasticity was derived using Womersley's flow velocity-distensibility relationship (AT RIGHT) and phase-adjusted propagation velocity relationships (AT FAR RIGHT)

FIG. 29d - FLOW & VELOCITIES

Womersley's flow derivation also defines the blood-wall mass interaction in relation to radial displacement:

where V is peak flow velocity (average translumenal); $\xi$ is phase-adjusted prop velocity, and $2\xi =\Delta$ or $\pm\xi$ about Rm mean radius $$\frac{2\xi}{R_m} = \frac{V}{C}$$

This shows radial distension reflects the pulsatile gradient acceleration of flow, whereby more fluid enters than leaves an artery segment pursuant to flow continuity principles. With the C being related to elasticity, radial distensibility decreases with increased wall stiffness.

FIG. 29e - PHASE-ADJUSTED PROPAGATION VELOCITY

Invented system harmonically phase-adjusts propagation velocity with wall-constrained blood viscosity (#2) and visco-elastic effects (#3):

1. Propagation velocity of thin-walled vessels with non viscous fluid is:
$$c_o = \sqrt{\frac{E_y(2-\eta)}{3\rho}}$$

2. Womersley $\Delta C\alpha$ phase effect of blood-wall mass interaction is harmonically applied in modifying $c_0$ to $C_1$:
$$C_1 = c_{o1} \cdot C_{\alpha 1} = c_{o1} \cdot \sqrt{\frac{M_{10}}{(1-\sigma^2)}} \cdot \sec\left[\frac{e_{10}}{2}\right]$$

3. which is modified to $C_2$ with Rmw normalization-determined $\phi_N$, the artery visco-elastic phase retardation of flow. $E_{yf}$ elasticity incorporates artery phase effects with $\Delta C_z$:
$$C_2 = C_1 - \Delta C_N = C_1 \cdot \left[\frac{\Delta\phi_N \cdot 60 \cdot SR}{2\pi \cdot HR \cdot J}\right] \text{ where } \Delta C_2 = \frac{C_2}{c_{o2}}$$

SR is sampling rate, J is peak sample #

Closely analogous to liquid in an elastic tube (Kaufman-1963) Newton first applied this in defining velocity of sound in air
$$c_o = \sqrt{\frac{VOL.ELASTICITY}{density}}$$

Original elastic tubework (Young-1809) derived to
$$c_0 = \sqrt{E_y h/2R_m \rho}$$

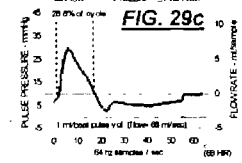

---

Simulations confirm: (i) McDonald's contention that the Womersley method is impervious to inaccuracy of elasticity changes, and (ii) its derivation confirms flow waveform accuracy properly compensates for pressure reflectances of peripheral resistance, which are included in the system's pressure waveform contours. This provides for accurate elasticity-based pressure gradient solutions

FIG. 29f - FLOW-BASED ELASTICITY

Elasticity is a function of the 2nd-order ratio of pulse pressure to flow velocity:

$$E_{yf} = \frac{P^2}{V^2}\left[\frac{3}{(2-\eta)\rho}\right]\frac{1}{\Delta C_z^2}$$

Wave energy principles dictate the velocity of the propagating pressure wave relative to the volumetric elasticity of its fluidic medium. With travel distance being the product of time (1/f) and velocity, greater constraint (reduced travel) in the transverse direction (due to diminished wall compliance) diverts the pulse energy to travel faster longitudinally. And with wavelength being proportional to propagation velocity at any frequency with $c_o = \lambda \cdot f$, the pressure gradient and flow is reduced with increased stiffness and propagation, in that the pressure wavelength increases.

FIG. 29g - FLOW

Pulsatile flow is:

$$\dot{Q} = \frac{P \cdot R^2}{\sqrt{E_{yf}}} \cdot w$$

DEFINITIONS: Flow $|Q| V=R^2|$, elasticity $[E_y]$, pulse pressure $[P]$, radius $[R]$. Non-dynamic $[w]$ wall affects are thickness, and blood viscosity & density:

$$w = \frac{3}{\Delta C_2}\sqrt{\frac{3}{(2-\eta)\rho}}$$

Aortic and conduit artery flow and resistance are pulsatile measures. Cuff site beat-by-beat flows account for distal capillary delivery.

FIG. 29h - RESISTANCE

Flow impedance is:

$$\ddot{Z} = \frac{P}{\dot{Q}} = \frac{\sqrt{E_{yf}}}{R^2 \cdot w}$$

Elasticity and bore, which vary in relation to arteriole regulation, are the dynamic flow resistance factors. The $E_y$ curve indicates both elasticity and radius vary substantially. $E_{yf}$ is the dominate impedance factor in hypertension, and R (radius) varies most in circulatory failure.

CARDIAC STROKE OUTPUT

With flow continuity principle:

$$Q_1 = V_{m_1} \cdot \pi R_1^2 = n Q_1 = n \cdot V_{m_2} \cdot \pi R_2^2$$

Normal aorta and brachial blood flows show artery tree branching "n" for the brachial artery to be 73.5

METHODS, APPARATUS AND ARTICLES-OF-MANUFACTURE FOR NONINVASIVE MEASUREMENT AND MONITORING OF PERIPHERAL BLOOD FLOW, PERFUSION, CARDIAC OUTPUT BIOPHYSIC STRESS AND CARDIOVASCULAR CONDITION

FIELD OF THE INVENTION

The present invention relates generally to the field of medical devices, instruments and methods, and more particularly to such instruments and methods used in the noninvasive hemodynamic measurement and heart beat-by-beat monitoring of cardiac and peripheral blood flows, blood pressure, and physiologic cause-and-effect conditions of cardiovascular disease.

BACKGROUND OF THE INVENTION (Prefatory Note: The following is intended as a detailed explanation of the justification for the present invention. It is believed that this information will assist the skilled reader in appreciating the various aspects, features and applications of the invention. While this background section makes reference to, and draws support from, various prior-art sources (such as published articles), significant portions of this section present the inventor's own analysis and findings which, though based upon the prior art, is not prior art itself. Accordingly, no assumption should be made that non-published information discussed in this background section constitutes, by admission or otherwise, prior art to the present invention.)

Blood flow is a specific indicator of medical condition and cardiovascular health, however, its measurement impracticality is impeding focus on important problems:

inadequate warning of abnormal blood flow and volumes in hospital care;
ineffective warning of conditions that cause heart attacks and strokes;
high mortalities of septic shock and drug problems;
ineffective assessment and costly management of congestive heart failure;
brain impairment with surgery of patients with cardiovascular disease; and
ineffective disease management due to inaccuracy and limited relevance of BP.

Hospital pulse oximeter medical devices are practical for measuring relative hemoglobin oxygen content in the blood, however, the impracticality of measuring blood flow and its companions, perfusion and cardiovascular disease, has caused these physiologic parameters to be neglected for a long time. Invasive monitoring is costly and has inherent risks, and noninvasive flow monitoring has been unreliable and impractical: instead, blood pressure, pulse oximeter and ECG monitoring is used, which inadequately specify patient condition. ECG trace monitoring also lacks practicality and hemodynamic significance. Thus, clinicians are dependent on blood pressure (the simple blood pressure cuff is used professionally over 12 billion times yearly) and pulse oximeters to determine patient condition and treatment needs.

Physicians rely on blood pressure as the principal indication of blood flow and cardio-vascular disease, but this is often misleading, especially with abnormal flows. The relationship between flow and pressure is misunderstood and unpredictable. Even when measured accurately, BP yields little information about its companion blood flow, the carrier of nutrients and waste products. Nor is blood pressure a specific measure of cardiovascular disease, a principal cause of impaired blood flow and perfusion.

Physiologic sustainment depends on "perfusion", i.e., the blood flow transport of oxygen and other materials through conduit arteries, arterioles and capillaries to tissue. Pulse oximeters are mistakenly used as an indicator of perfusion while being used to monitor blood oxygen; this is because these devices give no indication of reduced blood flow transport until flow ceases altogether. Moreover, pulse oximeter oxygen content measurements can be many minutes latent without this being recognized by the anesthesiologist.

The above misleading measurement propensities may be part of why an estimated 25% of the population are said to be untreated or treated inappropriately. Exemplifying effects of this in hospital care, authorities "have produced very convincing evidence that the so-called vital signs of every day medical care have little to do with the survival of the critically ill patient." See C. Bryan-Brown, *Blood Flow to Organs: parameters for function and survival in critical illness*, Critical Care Med. 16:170 (1988).

Additional observations about monitoring of blood flow are:

1. Blood flow is pulsatile, moving forward only briefly during each heart beat; accurate measurement requires computations based on flow waveforms, which is not done with approximative heart catheterization and other methods that are used today in hospitals.

2. Blood flow is abnormally low, by as much as 60%, in those with cardiovascular disease. See M. E. Safar, *Pulsed doppler: diameter, flow velocity and volumic flow of brachial artery in sustained essential hypertension*. Circulation 63:2 393–400 (1981). Also see T. B. Levine, *Regional blood flow supply and demand in heart failure*. Am Heart J 120:1547 (1990). Conversely, elevated flows are usually associated with blood infections, anemia, various hormonal imbalances, anxiety and any physical activity. See A. C. Guyton's *Textbook of Medical Physiology*, FIG. 23–5, W. B. Saunders Co. (7th ed. 1986).

3. The body's total blood flow (cardiac output) varies greatly to meet physiologic needs; the variable portion of the cardiac output is the approximate 70% of high resistance flow to skin, skeletal muscle and organs other than the heart and brain; high resistance flow is controlled by the sympathetic nervous system and arteriole arteries with strong contractible vessel walls. Forearm blood flow of the brachial artery is representative of this blood flow "safety reserve" that serves to protect the brain and heart from disruptions of supply. Limb blood flow monitoring, therefore, can be a valuable analytical indication of cardiac output because it is a more obvious and earlier warning of physiologic transitions than cardiac output, which is a weighted average of both high and low resistance blood flows.

4. Although low blood flow and blood pressures generally change together, pressure and flow do not correspond at relatively normal and higher blood pressures as is commonly believed. Blood flow decreases at higher blood pressures, and the amount and rate of diminution varies among individuals. Flow varies unpredictably because the body's auto-regulation processes strive to maintain blood pressure constant and because of cardiovascular disease. Large unrecognized flow abnormalities can go unnoticed for long periods of time when blood pressure monitoring is relied upon.

5. Blood pressure also hides vital regional flow variations within the circulatory system. When cardiac output is reduced, blood flow is usually maintained to the heart and brain, while flow to other less critical regions and organs is total shutdown, which would be when flow to the brain becomes compromised. This redistribution normally occurs in part by auto regulated constriction of the wall muscle of thousands of end-arteries (arterioles). Some degree of predictability might apply to the hemodynamic effects of such vasoactivity if it were not for cardiovascular disease. However, thickened arteriole walls causes significant static impairment of the flow safety reserve, a high risk of adverse consequences of hospital patients with cardiovascular disease.

6. Anesthesiologists and critical care providers use pulse oximeters to measure the oxygen content in peripheral blood hemoglobin (the "$O_2SAT$"), usually in a patient finger. Although an indication of respiration or ventilator function, the $O_2SAT$ does not reflect the blood oxygen transport, or "perfusion". Perfusion monitoring involves measuring pulse oximeter $O_2SAT$ and blood flow most preferably in the main artery of a left arm, whereby a beat-by-beat blood flow value can be multiplied by the corresponding $O_2SAT$ oxygen content to determine the perfusion value or index for display on the monitor screen.

7. Along with being an erroneous indicator of blood flow, the pulse oximeter $O_2SAT$ values can be misleading indicators of respiratory function during and after periods of blood flow change, which is when measurement reliability is often most critical. Thus, anesthesiologists may be misled into erroneously (i) believing blood flow is normal when it is greatly reduced (such as just prior to cardiogenic shock) to being as little as 5% of normal, (ii) believing a distressed patient with a respiratory or ventilator problem is normal for minutes before the pulse oximeter discloses the problem, and (iii) treating a patient for a respiratory or ventilator problem that no longer exists.

8. Blood flow reveals critical conditions significantly earlier and more specifically than does blood pressure. In emergency rooms, patients can be in cardiogenic shock with peripheral blood flow shutdown for a prolonged period before blood pressure changes significantly whereby it often "crashes" to first reveal the condition. In critical care, it is believed that practical flow monitoring can provide early warning of drug interactions and dosage errors that kill over 44,000 hospital patents, and septic shock (e.g. systemic inflammatory response syndrome) that afflicts 751,000 hospital patients annually and kills 215,000. See studies in Critical Care Medicine magazine report of hospital discharges as reported in Wall Street Journal (Sep. 11, 2001), E. Haber, Harvard Medical School, Center for Prevention of Cardiovascular Disease, as reported in USA Today (Sep. 25, 1996); D. Bates, Harvard Medical School "Study Finds Drug-Reaction Toll Is High" (Associated Press Apr. 14, 1998); and W. Richardson,'s W. K. Kellogg Foundation Institute of Medicine committee report (Dec. 10, 1999). In surgery, when practical blood flow monitoring is available, the hemodynamic cardiovascular conditions that cause neuropsychiatric brain dysfunction (discussed below) and heart attacks may be identified for preventive intervention.

9. In addition to not providing an indication of blood flow changes, present non invasive blood pressure devices, by not taking into account blood flow variations, often give inaccurate or delayed blood pressure readings, which occur most commonly for the critically ill and patients with cardiovascular disease. Blood pressure inaccuracy and the lack of continuous surveillance are acknowledged hospital safety and health care issues.

10. With cardiovascular adversity probably being the greatest risk of hospital care, physicians need an effective means of warning of disease and drug interactive toxicity effects that cause heart attacks, strokes and neuropsychiatric dysfunction morbidity. See G. W. Roach, et al. *Adverse cerebral outcomes after coronary by-pass surgery*. NEJMed v335 no25 (1997). As part of this, prior to and during surgery, anesthesiologists need a reliable way, without trial and error, to select and gauge effects of powerful vasoactive agents. Along with blood flow, the heart loads (resistance) and work are important. For example, if the source of low blood flow is the heart, avastly different drug regimen is used than if flow is decreasing because of high peripheral arterial resistance. The simultaneous determination of central and peripheral blood flow and heart loads is needed for many patients.

Beyond the needs of hospital monitoring, the literature is replete with indications of need for better measurement and knowledge of the cause and effects of cardiovascular disease. It is widely held that early and more specific disease measurement of at-risk cardiovascular disease patients can reduce heart attacks, strokes and congestive heart failure rates. Hemodynamic science indicates that hemodynamic principles need be applied to achieve reliable non-invasive blood pressure accuracy. Hemodynamic science also teaches that, even if measured accurately, blood pressure can not be a reliable indication of cardiovascular disease. High blood pressure readings cannot reveal if the effect is temporary, such as being caused by a drug reaction, or is chronic and an effect of cardiovascular disease or other origin. Moreover, if it is the effect of cardiovascular disease, elevated blood pressure can not disclose: (i) the stage of the disease; (ii) whether it might be worsened by a drug therapy; (iii) how rapidly the condition is worsening; and (iv) the resulting increased likelihood of heart attack and stroke. The significance of these limitations is that present measurement methods are effectively contributing to reduced life span. Prevention of the disease, heart attacks and strokes for approximately 80 million Americans is needed, including for 35% of those with cardiovascular disease that will experience sudden death without prior diagnosis, largely because of understated and inconsistent BP measurements. A broader patient population needs to be screened, diagnosed and monitored in hospitals using more specific information, and at an earlier phase in the disease progression, for more effective preventive care. This raises vital issues:

Diagnosis and management of cardiovascular disease is based primarily on risk factor information that is inexact and subjective;

The reduced blood flows of cardiovascular disease can distort non invasive blood pressure measurement accuracy;

Blood pressure is a fluidic measure that tells little about effects on the heart and arteries. To illustrate, at a high blood pressure, thicker artery walls are damaged less than thin artery walls when other aspects are unchanged; and Biophysics, based on Newton's second law, indicates that blood flow anomalies must be a major unrecognized determinant of cardiovascular disease.

Unlike most other diseases, biochemical factors may not to be the principal initiator of cardiovascular disease. Historically, research has been focused mostly on cholesterol, homocysteine, nitric oxide and artery wall relaxation. However, these appear to be secondary effects of a more basic underlying biophysical cause. See G. L Duff, *Experimental cholesterol arteriosclerosis and its relationship to human arteriosclerosis*. Arch. Path. 20:81–123; 259–304 (1935). As evidence of current thinking, Dr. Paul Ridker, Harvard Medical School, is credited for discovering an inflamed coronary artery phenomena and a related sudden "popcorn" closure, the precipitating event of 70% of heart attacks. Although the cause of artery inflammation is not known, Ridker indicates it is "characterized by a decades-long cycle of irritation, injury, healing and re-injury to the inside of the blood vessels." This source also states "researchers wonder if more benefit might be gained by investigating causes of the arterial injury". R. Winslow, *Heart-disease Sleuths Identify Prime Suspect: Inflammation of Artery*. Wall Street Journal Oct. 7, 1999.

Hemodynamics researchers have yet to measure physical phenomena that science would assert to be an acceptable biophysic cause of hypertension, cardiovascular disease and its mortality. Specifically, in material science, excessive higher frequency stresses (internal forces of materials that exceed stress limits) are known to produce tiny structural fractures that can invite intrusion by extrinsic elements. This concept must apply to blood flow conditions that alter and cause deterioration of the principal cardiovascular vessels (left heart and arteries). By applying elasticity stress measurement relationships, physiologic simulations conducted by the inventor reveal that higher frequency artery elasticity moduli can easily exceed the limit of cardiovascular elastin-smooth muscle wall structure. This limit, according to measurements of hemodynamic researchers that assessed the effects of contractility and frequency, is approximately $13 \times 10^6$ dynes/cm$^2$. See D. A. McDonald's *Blood Flow in Arteries*, Arnold Press (1960), pages 244, 268 and 279. The simulated high or erratic heart rates, as well as waveforms that are indicative of vasoconstriction (e.g., caused by nicotine) and cardiovascular disease, produces higher frequency elastic stiffnesses that exceed the limit by many times.

With 41% of U.S. mortality being related to cardiovascular disease (as compared to 23% being cancer-related), scientifically acceptable measurement and analytical relevance is needed for understanding and controlling the cause and progression of the disease. Thus, biophysic pulsatile cardiovascular stress is a measurement that is needed to improve the specificity of blood pressure measurement, and may become valuable for physicians to specify the most effective pharmacologic treatment regimen for patients and for determining when patients should be referred for costly diagnostic tests. Cardiovascular stress measurement specificity in disease management can also confirm the nature of the commencement of hypertension and cardiovascular disease, which is hypothesized to occur irreversibly in infancy. Simulations suggest that excessive stresses, which are produced by underdeveloped or slower developing infant hearts, may be a principal catalyst of cardiovascular disease. Specifically, a fast heart beat (e.g., 110–140 BPM at birth), which is needed to supply the body's oxygen, produces significant higher-frequency pulsatile stresses, even at lower blood pressure. Relatively smaller, or slowly developing, infant hearts would need to continue beating at a fast rate for a larger number of months or years before the heart's growth catches-up to fulfill the body's circulatory needs at a normal lower heart rate. It is believed that the extra work of prolonged increased pulsatile wall stress of end-arteries (the arterioles and pre-capillary sphincter vessels) cause excessive developmental thickening of the end artery muscular walls. Such thickening results in smaller, statically constricted lumen, like thicker donuts with smaller holes.

The mathematics of biophysic stresses that are presented herein show that, once initiated, unfavorable stresses and impaired cardiovascular function are likely to progressively worsen throughout life. This is consistent with the growing severity of the disease phases: artery thickening and damage to artery linings; cholesterol lipid infiltration; arteriosclerosis; calcification recomposition; coronary artery inflammation; and end-stage plaque fragmentation and "popcorn" rupture that produce strokes and heart attacks. The nonlinear elastic stress relationship suggests that the late-stage disease phase is likely to accelerate greatly and extend within the circulation in a matter of a relatively few years of life. Clinical evidence of this is that later-stage heart disease stresses would be and apparently are directly related to reduced cardiac stroke volumes of left ventricular hypertrophy or "LVH", which has been strongly linked to both heart attacks and high rates of post-surgery neuropsychiatric brain dysfunction morbidity, e.g., up to 70% of bypass procedures and 53% of general surgery patients, of which over half are permanent impairments. See S. Newman, *Incidence and nature of neuropsychological morbidity following cardiac surgery*. Perfusion 4:93–100 (1989). Also see T Monk, MD, *Cerebral $O_2$ Decrease Linked to Post-Op Cognitive Dysfunction*, Anesthesiology News (April 2001). Also see M. Newman, MD, *Longitudinal Assessment of Neurocognitive Function After Coronary-Artery Bypass Surgery*. NE J Medicine 344:6 (2001). This is probably related to thickened brain arterioles; although blood flow is normally constant in the brain, research has shown that brain flow decreases at two-thirds the rate of the large cardiac output reductions that occur in ambulatory individuals with LVH congestive heart failure. Reduced blood flow, and its related excessive stresses, may also explain the apparent relationship between high blood pressure and impaired memory and intellectual function later in life. See L. J. Launer, et al. *The association between midlife BP and late-life cognitive function*. JAMA.274:1846–51 (1995). Thus, the measurement of patient biophysical cardiovascular stress, relation to the late-stage acceleration phase, can be an important part of cardiovascular disease management.

Biophysic cardiovascular stress can also be the central aspect of several types of drug reactions. Specifically, drugs that alter the contractility of the heart and arterioles or cardiac rhythm in patients can accelerate cardiovascular stresses, the disease progression and its adverse incidents. These include psychotropic (e.g., Ritalin and Prozac), diet (Pondimin) and blood pressure lowering (Poisicor, Isradipine and Cardula) drugs. For example, in a major study, Isradipine nearly doubled heart attacks and strokes. See Borhani et al. "*Results of Multicenter Isradipine Diuretic Atherosclerosis (MIDAS) Study*" JAMA 276:10 (1996); Associated Press release "i Roche pulls Posicor from world market" (Jun. 9, 1998); and Dow Jones Newswire "*Pfizer Faces Lawsuit over alleged risks of hypertension drug*" (May 31, 2000). Moreover, the costs of this are great, as evidenced by the $12 billion that had to be set aside for claims related to rapid and extensive heart valve disease caused by the Fen-Phen diet pill. See American Home Products press release; WSJournal (Jan. 25, 2001).

Another matter is the need for measurement practicality for more effective preventive care for a broad patient population such as is now being monitored by blood pressure and pulse oximeter devices. Cardiovascular measurement is limited by patient risk and costs of measurement; excluding imaging systems, the measurement of blood flow and continuous blood pressure monitoring has been invasive; requiring the use of tubing in the heart, esophageal channel and/or vital arteries; moreover this is limited to a short time period because of infection spread, adverse patient reactions, and artery inadequacy, as well as clotting and micro bubbles that cause significant inaccuracy. Furthermore, noninvasive blood pressure devices are also inefficient and costly; they do not provide continuous surveillance; they are not tolerated by patients because repetitive cuff pressurizations causes trauma and circulatory anomalies, they use flawed empirical methods that causes significant inaccuracy when artery elasticity and blood flow are abnormal, and cuffs are a major source of cross contamination of staphylococci infection and other sepsis in hospitals. To overcome these measurement obstacles, an easily and lightly applied noninvasive patient sensor is needed that can provide (a) comfort; (b) continuous beat-by-beat surveillance; (c) greater measurement reliability; and (d) measure and monitor blood flow and other vital parameters; and (e) to optionally provide for reducing hospital cross-contamination and sepsis by requiring care providers to dispose of patient sensors after a programmed time of use and to use sensors on only one patient.

Summarizing, blood pressure, even when measured accurately, is an ineffective indication of hospital patient safety or disease condition. Flow and perfusion monitoring should be a standard of surgery and critical care, especially for patients with cardiovascular disease. Biophysical stress and cardiac hemodynamic profiles would be a more specific characterization of coronary artery inflammation, propensity for heart attacks and for preventing and managing the progression of cardiovascular disease.

A vast array of devices/systems/methods for characterizing and/or monitoring cardiovascular parameters appear in the prior art. Nevertheless, none of these provides a practical and economical solution to the monitoring needs of the medical community. For example, U.S. Pat. No. 5,876,347, METHOD FOR VASCULAR IMPEDANCE MEASUREMENT, to Chesey et al. purports to compute stroke volume as a linear function of ejection time, body surface area, age and heart rate. See '347 patent, column 5, lines 12–20. However, this linear model is, at best, a crude approximation of reality—and the '347 inventors essentially admit as much. See '347 patent, column 5, lines 27–30 (claiming an "accuracy" of +/−25% in 90% of patients).

U.S. Pat. No. 6,117,087, METHOD AND APPARATUS FOR NONINVASIVE ASSESSMENT OF A SUBJECT'S CARDIOVASCULAR SYSTEM, to Kamm et al. describes a technique for estimating cardiovascular model parameters by comparing model-predicted results with measured data.

U.S. Pat. No. 5,730,138, METHOD AND APPARATUS FOR DIAGNOSING AND MONITORING THE CIRCULATION OF BLOOD, to Wei-Kung discloses a system which computes the spectral frequency components of real-time BP waveforms and analyzes the various spectral components, using principles of Chinese medicine, to ascertain the health of various organs. See, e.g., '138 patent, column 3, line 33–34 ("[t]he harmonic for the liver is known to be the first harmonic of the heartbeat") and lines 37–38 ("[t]he harmonic for the kidney is known to be the second harmonic of the heartbeat"). The '138 patent does not teach or suggest the computation of any physically meaningful cardiovascular parameters; nor does it teach any means or method for performing such computation.

U.S. Pat. No. 5,103,828, SYSTEM FOR THERAPEUTIC MANAGEMENT OF HEMODYNAMIC STATE OF PATIENT, to Bohumir suggests that stroke volume can be calculated as a multiplicative function of equivalent thoracic length (cubed), ventricular ejection time and peak ejection velocity, divided by thoracic fluid bioimpedance, with equivalent thoracic length derived from the patient's height and weight. See '828 patent, column 15. Here, too, the model is not based on physical reality. Indeed, the '828 patent even states: "The only absolutely accurate blood flow measurement method . . . is a calibrated cylinder to collect blood and a stopwatch." ('828 patent, column 4, lines 54–59.)

U.S. Pat. No. 4,205,688, METHOD AND APPARATUS FOR DEVELOPING AND MEASURING PULSED BLOOD FLOW, to Hauser et al. provides a combined electromagnetic/occlusive-cuff apparatus which purports to measure arterial blood flow in a limb. The '688 method/apparatus makes no attempt to model, estimate or quantify the physical parameters that control blood flow (e.g., radius, elasticity, etc.) in arteries.

U.S. Pat. No. 4,240,294, FLOW METER, to Grände et al. discloses an in-line type of flow meter adapted for use in kidney dialysis and heart/lung machines. Such device is neither useful for, nor adaptable to, non invasive applications.

U.S. Pat. No. 5,241,963, METHOD FOR DETECTING THE ONSET AND RELATIVE DEGREE OF ATHEROSCLEROSIS IN HUMANS, to Shankar provides a non invasive method/apparatus for determining peak "arterial compliance," defined as the ratio of arterial volume change, $\Delta V$, to change of pulse pressure (i.e., systolic less diastolic), $\Delta P$. The '963 patent does not suggest any use of such "arterial compliance" for continuous monitoring of blood flow, or show any scientific relevance or relationship of this empirical index to scientific measures of artery elasticity or flow resistance.

U.S. Pat. No. 5,755,229, PULSE WAVE ANALYSIS DEVICE, to Amano et al. discloses a method/apparatus for using fast Fourier transform ("FFT") analysis of signals from a finger-mounted pressure cuff. Like the previously-cited '138 patent, the '229 patent does not measure any physically meaningful cardiovascular parameters. (See, e.g., '229 patent, column 1, lines 24–29, where "According to this form of pulse diagnosis, a disease can be diagnosed accurately only when the practicing 'sage' feels the patient's pulse. It might be extremely useful if the same diagnosis could be performed by a machine.").

U.S. Pat. No. 4,651,747, WAVEFORM INFORMATION OBTAINING TECHNIQUES ASSOCIATED WITH AN INDIVIDUAL'S BLOOD PRESSURE; U.S. Pat. No. 4,712,563, METHOD OF AND APPARATUS FOR DETERMINING THE DIASTOLIC AND SYSTOLIC BLOOD PRESSURE OF A PATIENT; U.S. Pat. Nos. 4,664,126, 4,699,151, 4,697,596 and 4,699,152, TECHNIQUES FOR OBTAINING INFORMATION ASSOCIATED WITH AN INDIVIDUAL'S BLOOD PRESSURE INCLUDING SPECIFICALLY A STAT MODE TECHNIQUE; U.S. Pat. No. 4,564,020, METHOD AND APPARATUS FOR OBTAINING AN INDIVIDUAL'S SYSTOLIC BLOOD PRESSURE; and U.S. Pat. No. 4,154,238, APPARATUS AND PROCESS USING SECOND DERIVATIVE OF OSCILLOMETRIC WAVEFORM FOR PRODUCING SPHYGMOMETRIC INFORMATION, all to Link, disclose various methods/apparatus for using pressure cuff waveform data to obtain and/or track systolic and diastolic blood pressure. None of these Link patents teach or suggest any method for computing or estimating blood flow, even though blood flow is a principal determinant of the noninvasive physiologic measures that are sensed for computing estimates of blood pressure in present blood pressure measurement devices.

U.S. Pat. No. 5,301,675, APPARATUS FOR MEASURING BLOOD FLOW VELOCITY AND BLOOD FLOW VOLUME IN AORTAS, to Tomita et al. discloses a technique, using multiple cuffs, to estimate the propagation velocity of the pulsatile wavefront along the brachial artery and to use this velocity information to estimate flow rate in the aorta. The '675 technique does not attempt to model or compute the physical parameters that actually govern arterial blood flow, but instead, relies on an assumption that: "when a cuff is put around an upper arm and a pressure thereof . . . is retained at systolic pressure SP, a velocity at which a pulse wave clears the pressing cuff is approximate to a blood flow velocity VH in the high pressure period . . . of the aorta." ('675 patent, col. 10, lines 21–26.) U.S. Pat. No. 5,423,324, APPARATUS FOR DETECTING AND DISPLAYING BLOOD CIRCULATORY INFORMATION, to Tomita teaches use of low-pressure monitoring cuff, secured around the upper arm, to provide an approximate real-time aortic pressure waveform.

U.S. Pat. No. 5,289,823, NONINVASIVE AORTIC BLOOD FLOW SENSOR AND METHOD FOR NONINVASIVELY MEASURING AORTIC BLOOD FLOW, to Eckerle, teaches an approach for estimating aortic blood flow by modeling a "2-cm section of the aorta, together with the two subclavian arteries," as a "capillary- (or orifice-) type flowmeter." ('823 patent, col. 2, lines 26–29.) Using this "flowmeter" analogy, blood pressure signals from arteries in the left and right arms are combined to provide an estimate of aortic flow. The '675 patent does not teach or suggest any method for measuring flow at the site(s) where the actual blood pressure signal is being measured.

U.S. Pat. No. 3,920,004, DEVICE AND METHOD FOR NONINVASIVE MEASUREMENT OF BLOOD PRESSURE, RESISTANCE INERTANCE, COMPLIANCE, IMPEDANCE, BLOOD FLOW RATE, KINETIC ENERGY, FLOW VELOCITY AND PULSE VELOCITY OF A SEGMENT IN MAN, to Nakayama discloses a system using distinct pressure and volume sensors, both positioned along the same artery. The '004 patent does not teach or suggest any method for computing a real-time flow waveform, nor any frequency domain cardiovascular or hemodynamic parameters.

U.S. Pat. No. 4,243,648, METHOD AND APPARATUS FOR MEASURING BLOOD PRESSURE AND PULSE RATE, to Trimmer et al. discloses a device utilizing two spaced-apart arterial pressure transducers to capture various aspects (e.g., rise time, transit time) of the real-time pulse pressure signals, which aspects are used to compute systolic/diastolic pressure and pulse rate.

U.S. Pat. No. 3,095,872, BLOOD PRESSURE MEASUREMENT, to Tolles teaches a method for measuring blood pressure by impressing a substantially-higher-than-heart rate signal upon an artery and detecting phase changes in said signal as it travels along the artery.

U.S. Pat. No. 3,104,661, SYSTEM FOR CONTINUOUS BLOOD PRESSURE DETERMINATION, to Halpern discloses a blood pressure measurement device having an inflatable cuff and separate pressure transducer.

U.S. Pat. No. 4,649,928, NOISE-IMMUNE BLOOD PRESSURE MEASUREMENT TECHNIQUE AND SYSTEM, to Samaras et al. teaches a device having separate occlusion and sensing cuffs, and a method for detecting blood pressure in noisy environments without having to detect individual heart pulses.

U.S. Pat. No. 4,858,616, BLOOD PRESSURE MEASUREMENT SYSTEM FOR FILTERING LOW-FREQUENCY, HIGH-AMPLITUDE NOISE, to Samaras et al. provides an apparatus similar to the '928 Samaras et al. patent, but with an additional capability to "recognize slow, large noise signals" created by patient movement and "filter out these slow, large noise signals." ('616 patent, col. 2, lines 43–44 and 46–47.)

U.S. Pat. No. 5,152,296, DUAL-FINGER VITAL SIGNS MONITOR to Simons discloses a device with "a pair of finger cuffs that each include an, electrocardiograph electrode, a first radiation source and detector pair for blood pressure measurement, and a second radiation source and detector pair for blood oxygenation measurement." ('296 patent, col. 2, lines 10–14.)

U.S. Pat. No. 5,050,613, METHOD AND APPARATUS FOR VASCULAR TESTING, to Newman et al. discloses a system which includes a plurality of pressure transducer(s) and/or cuff(s), positioned at various sites (e.g., upper arm, thigh, ankle) on the patient. Signals from the various transducer(s) are compared/evaluated to detect cardiovascular abnormalities, such as arterial blockages.

U.S. Pat. No. 4,729,382, METHOD AND APPARATUS FOR UTOMATICALLY DETERMINING PULSE RATE AND DIASTOLIC AND SYSTOLIC BLOOD RESSURE, to Schaffer et al. discloses an automatic blood pressure measuring device that includes inflatable occlusion and sensing bladders, each surrounded by a rigid tube.

U.S. Pat. No. 5,099,852, METHOD FOR DETERMINING THE ARTERIAL BLOOD PRESSURE IN A NONINVASIVE MANNER, to Meister et al. teaches a method for using two, spaced-apart ultrasonic transducers to monitor arterial diameter at two locations along an artery and, from these measurements, compute propagation velocity, pulse rate, compliance and pressures. U.S. Pat. No. 5,152,297, METHOD AND APPARATUS FOR ESTABLISHING THE PRESSURE-DIAMETER RELATIONSHIP OF AN ARTERY BY NONINVASIVE MEASURES, to Meister et al. utilizes a similar approach.

U.S. Pat. No.5,101,828, METHODS AND APPARATUS FOR NONINVASIVE MONITORING OF DYNAMIC CARDIAC PERFORMANCE, to Welkowitz et al. discloses a system that computes a frequency-domain transfer function between femoral and carotid pulse pressure signals and, using an electrical circuit-based model, derives aortic blood flow. This '828 patent does not teach or suggest any method for using the frequency-domain pulse pressure signals to compute arterial blood flow beneath the pressure sensor(s).

U.S. Pat. No. 5,048,533, METHOD AND APPARATUS FOR A NONINVASIVE EXAMINATION OF BLOOD CIRCULATION IN A LIVING ORGANISM, to Muz discloses a method in which two inflatable cuffs, each mounted around a different artery, are used to derive a real-time blood pressure signal.

U.S. Pat. No. 5,626,141, BLOOD PRESSURE MEASUREMENT APPARATUS AND ASSOCIATED METHOD, to Takeda describes a cuff-based device for measuring the velocity and acceleration of an underlying arterial wall.

U.S. Pat. No. 5,724,980, PULSE DIAGNOSIS METER, to Nakamura et al. discloses a device in which pulse signals from sensors on right-hand and left-hand fingers, are compared to detect abnormal differences in blood pressure between right and left sides of the body.

U.S. Pat. No. 5,743,857, BLOOD PRESSURE MONITOR APPARATUS, to Shinoda et al. discloses a device which monitors a phase difference between electrocardiographic signals, obtained from two different parts of the body, as a means for determining when to initiate a blood pressure measurement—thus avoiding unnecessary cuff inflations.

U.S. Pat. No. 5,724,981, PERIPHERAL ARTERIAL MONITORING INSTRUMENTS to Apple discloses a device for measuring arterial volume and compliance using an oscillometric approach, but with an improved cuff, capable of quantifying the amount of air expelled therefrom during the step-by-step deflation cycle. The '981 patent does not teach, or suggest, any technique for computing arterial wall lumen size or thickness.

U.S. Pat. No. 4,718,428, METHOD FOR DETERMINING DIASTOLIC ARTERIAL BLOOD PRESSURE IN A SUBJECT; U.S. Pat. No. 4,718,427, METHOD FOR DETERMINING SYSTOLIC ARTERIAL BLOOD PRESSURE IN A SUBJECT; U.S. Pat. No. 4,718,426, METHOD FOR DETERMINING DIASTOLIC ARTERIAL BLOOD PRESSURE IN A SUBJECT; and U.S. Pat. No. 4,669,485, APPARATUS AND METHOD FOR CONTINUOUS NON-INVASIVE CARDIOVASCULAR MONITORING, all to Russell, disclose indirectly related prior-art approaches by the present inventor.

While the aforementioned patents teach a variety of useful system components—e.g., computerized sampling systems, FFT processors, cuff inflation/deflation apparatus, a volume-quantified pressure cuff, waveform displays, etc.—and each of said patents is HEREBY INCORPORATED BY REFERENCE for its teaching of elements/components useful in connection with the present invention, none of these patents disclose, or even remotely suggest, a practical, economical, accurate and non invasive method for monitoring blood flow.

Accordingly, there exists a long-felt, but unsatisfied, need for a reliable, economical and noninvasive technique for measuring arterial blood flow. There also exists a long-felt, but unsatisfied, need for a technique capable of providing such measurements on a continuous and/or real-time basis. There still further exists a long-felt, but unsatisfied, need for improved critical care and surgical monitoring techniques that incorporate continuous and/or real-time flow-related data. Finally, there exists a long-felt, but unsatisfied, need for improved techniques for diagnosing, monitoring, managing and/or treating patients with cardiovascular conditions and/or patients who are taking potentially vasoactive drugs or drug combinations. The present invention addresses these, as well as other, needs.

SUMMARY OF THE INVENTION

The invention is for measuring cardiac output, limb blood flow, perfusion, blood pressure, artery elasticity, and cardiovascular deterioration and disease, including performing these measurements on a continuous heart beat-by-beat basis, for humans and animals. Unlike empirical methods of other noninvasive blood pressure concepts, the invention is grounded on scientifically appropriate hemodynamic principles that studies have validated as accurate, and is practical for wide clinical use. Devices constructed in accordance with the invention can be comfortably employed for numerous applications, including hospital monitoring, physician's office cardiovascular disease management and drug therapy monitoring, home monitoring and athletic applications.

The invention may be implemented in a variety of single or multi-sensor embodiments, such as: invasive pressure cannula sensor systems; noninvasive pressure transducer arrays and piezo or other strain sensing materials that are placed against the skin above arteries; "upstream" pulsing-sensors (that apply single or multi-frequency vibrations that are measured "downstream" from the first placement location); other types of plethysmographic sensors; sonic/ultrasonic/Doppler sensors; MRI blood spin magnetizer/sensors; oxygen sensors; and electrocardiographic sensors, etc.

In one of its most practical configurations, one innovation of the invention is to use only a noninvasive blood pressure cuff for sensing, applied on a patient's limb over a conduit artery in the manner currently practiced and shown in FIG. 1a. An advantage of the invention is that it preferably applies only low contact cuff pressure (10–25 mmHg, depending on the subject). This can be used after a brief calibrating occlusive cuff determination (OCD) cycle, a similar process as that of present intermittent automatic blood pressure devices used in hospital critical care. A non-obvious reason for the low pressure cuff, beside comfort, is to avoid flow turbulence and blood flow measurement distortion that occurs with a constricted artery.

Alternate configurations of this innovation can include extra sensors attached to the cuff so as to contact the skin of a limb for additional sensing of artery activity, and which may enable applying variants of inventive blood pressure and blood flow measurement methodologies. Such extra sensors are shown in an approximate configuration in FIG. 1b as Sensors M, M1, M2, M3, P, and D; these can make use of Piezo polyvinyldifloride (PVDF) with field effect transistor operational amplifier, single or array pressure transducer or other strain gauge sensing.

An alternate configuration of this innovation consists of a blood pressure cuff with Sensor M which is used to determine the cuff type, air volume and the looseness of the cuff wrap when on the limb. Generally speaking, this is achieved by comparing the Sensor M signal with the pneumatic signal from within the cuff, where both signals are the individual physiologic heart beat pulsatile waveforms and a near-DC filtered value, and selecting a value from a reference table based on the results of such comparison.

Another configuration of this innovation is to compare signals M1, M2, and M3 with each other as a means of assessing where the center of the cuff bladder is placed in relation to the artery being measured. For instance, when M1 signal is less than M3 signal, the system will be able to approximate that the cuff is placed between M2 and M3. Moreover, by comparing M1, M2, M3 and M signals, engineering reference table values or computations can enhance certain cuff "normalization" computations relative to the pneumatic signal.

A second innovation of the invention is a cuff normalization process for correcting measurement imprecision of common blood pressure cuffs. This reduces error of measuring a physiologic signal that is caused by variations in cuff size, wrap and temperature. This is in part achieved by using concurrently measured inflation cuff air volume and cuff pressure values to select reference values from predetermined inflation table data so as to determine certain cuff sensing parameters, e.g., the effective artery-cuff contact length (see FIG. 2 process 504). An alternative technique of this innovation employs extra sensors (see FIG. 1b) as part of this determination.

A third innovation of the invention relates to non invasive measurement of artery radius and wall thickness. This is performed with the formula of circumferential (tangential) or hoop artery wall stress $\tau_z$, $$\tau_i = \frac{r_i^2 P_i - r_o^2 P_o}{r_o^2 - r_i^2} - \frac{(P_i - P_o) \cdot r_i^2 r_o^2}{r^2 \cdot (r_o^2 - r_i^2)}$$

which depends on internal and external pressures ($P_i$ and $P_o$, respectively), and internal and external radius ($r_i$ and $r_o$, respectively). This relationship was published in L. H. Peterson, "*Vessel wall strain relationships*" from E. O. Attinger's *Pulsatile Blood Flow*, McGraw-Hill (1964). Novel derivations of this relationship enable determining relative wall thickness and radius at an occlusive cuff pressure during the OCD calibration, where such measure applies only after the calibration OCD when the external artery wall loading is removed, a reason for using a low pressure limb sensing device.

This process, depicted in FIG. 22, includes determining F cuff pressure, at which flow pulsatility commences, and C cuff deflation pressure at the peak of each pulsatile waveform and $r_p$ peak pulsatile displacement waveform amplitudes when the artery wall has zero wall stress at a peak $r_p$ value. This occurs when the artery wall first resists the expansion of $r_p$ during the cuff deflation that preferably is done at a linear rate of 3–12 per second, depending on heart rate (but can also be approximated for data measured for cuff pressure step downs that are used with some noninvasive blood pressure systems). At higher deflating cuff pressures (but below the F cuff pressure), the peak waveform amplitudes increase linearly, because the encircling cuff pressure is the sole determining variable, and mathematically the wall stress is negative at the peak displacements. As a preferred application, the above $\tau_z$ relationship is manipulated so as to define zero-stress relative wall thicknesses at the innermost and outermost wall of the artery, $\gamma_{z_i}$ and $\gamma_{z_o}$, respectively, as zero-stress functions of $[F-C]_{z_i}$ and $[F-C]_{z_o}$ shown below:

$$[F - C]_{z_i} = F - \frac{F}{2}[1 + (1 - \gamma_{z_i})^2]$$

and $$[F - C]_{z_o} = F \cdot \left[1 - \frac{2 \cdot (1 - \gamma_{z_o})^2}{1 + (1 - \gamma_{z_o})^2}\right]$$

which can then also be expressed as the average of these two zero-stress values in the form of the expression $[F-C]_z$ below:

$$[F - C]_z = F \cdot \left[1 - \left[\frac{(1 - \gamma_{z_o})^2}{1 + (1 - \gamma_{z_o})^2} + \frac{1 + (1 - \gamma_{z_i})^2}{4}\right]\right]$$

For avoiding computational complexity, the $[F-C]_z$ relationships have been plotted for all possible values, and negligible error has been shown to exist with an approximative relative wall thickness $\gamma_n$ function $$\gamma_n = \gamma_{PopAvg} + 0.01/\text{mmHg} \cdot [22.9 - (F-C)]$$

where $\gamma_{PopAvg}$ may be set to be approximately 0.115 based on physiologic studies or other sources of information, which is applied in process 513, FIG. 3.

The radius measurement also involves the $\tau_z$ relationship, with $\tau_z=0$ and with the substitution of $r_i=r_o \cdot (1-\gamma)$ whereby inner and outer wall relative wall thickness expressions, $\gamma_{z_i}$ and $\gamma_{z_o}$ are created.

$$\gamma_{z_i} = 1 - \sqrt{\frac{2C - F}{F}} \text{ and } \gamma_{z_o} = 1 - \sqrt{\frac{C}{2F - C}}$$

Also interjected is a wall mass relationship that geometrically reapportions any artery wall mass around smaller and larger inner lumen radii. This is based on artery tissue deformation being isovolumetric, isotropic, longitudinally constrained, and incompressible in the range of physiological stresses involved. See T. E. Carew, al. *Compressibility of the Arterial Wall*. Circulation Res. 23:61–68 (1968) and M. A. Biot, *Mechanics of incremental deformation*. J. Wiley, p56, 72, 82–95, (1965). Cross sectional wall area remains constant, as defined by $$\pi \cdot [R_n^2 - (R_n \cdot (1-\gamma_n))^2] = \pi \cdot [r_p^2 - (r_p - h_p)^2]$$

at any $r_p$ displaced radius (with wall thickness $h_p$) relative to that of the artery's normal uncompressed radius $R_n$ at which $\gamma_n = h_n/R_n$. By combining the wall thickness solution of this at $r_p$ radius, or $\gamma_p = h_{p/Rp} = 1 - \sqrt{1 - \gamma_n(2-\gamma_n) \cdot R_n^2/r_p^2}$ with $\gamma_{z_i}$ and $\gamma_{z_o}$ expressions from above, the unoccluded radius expressions are:

$$R_{n_i} = r_p \sqrt{\frac{2(F - C)}{\gamma_n(2 - \gamma_n) \cdot F}} \text{ and } R_{n_o} = r_p \sqrt{\frac{2 \cdot (F - C)}{\gamma_n(2 - \gamma_n)(2F - C)}}$$

or: $R_n = r_{p_z} \sqrt{\frac{4 \cdot (F - C)}{\gamma_n(2 - \gamma_n)(3F - C)}}$ where artery radius $R_n$ is the simple mathematical average of the inner and outer wall artery radii, $R_{n_i}$ n and $R_{n_o}$, a practical expression that lacks significant error, as applied in process 514, FIG. 3.

Also, for radius determination, the artery pulsatile $r_p$ radial displacement must be related to the arterial volumetric displacement amplitude (vda) measured by the cuff sensor. This can be established mathematically at the C cuff pressure when wall stress is nonexistent, whereby arterial vda is solely related to its lumen expansion capacity and the cuff decompression rate. For this, it must be recognized that each pulsatile vda is an expansion from zero (at complete lumen closure between pulsations where $r_p$ equals $h_p$ wall thickness), and with the physical geometric volume of a cylindrical lumen having "effective" internal radius $r_i$ and half the length of the cuff-artery contact, $L_c$, which can be expressed: vda=$L_c \pi r_i^2/2 = L_c \pi r_p^2 (1-\gamma_p)^2/2$ which enables defining $$r_p = \frac{1}{1 - \gamma_p} \sqrt{\frac{2 \cdot vda}{L_c \pi}}$$

With correspondence that exists between radial and volumetric displacement, e.g., because of no arterial elasticity effect at the zero-stress cuff pressure, this can be simplified to $r_p = \sqrt{vda/A_z}$ and applied as shown in FIG. 23 and process 514.

A fourth innovation of the invention, facilitated by the aforementioned artery measurements and cuff normalization processes, provides the first known practical measurement of Young's incremental elasticity modulus (ratio of biophysic stress to strain), $E_y$ below $$E_y = \frac{\text{stress}}{\text{strain}} = \frac{P \cdot \frac{R_i}{h}}{\Delta/R_n} = \frac{P \cdot R_n}{\Delta}\left[\frac{1-\gamma}{\gamma}\right]$$

$E_y$ is a measure of stiffness; greater values indicate stiffer vessel walls. Without the inventive technology, this could only be measured for excised animal specimens. Unlike other indices of arterial compliance that are generally impractical for clinical use, this measure is significant because it is mathematically and physically relevant to blood flow and cardiovascular disease. $E_y$ is a "composite" pulsatile elasticity measure, representing the average pulsatile stiffness-recoil effect for the waveform pulse, i.e., while the blood pressure rises from resting diastolic to peak systolic. This is also referred to as "static" elasticity because it represents relatively slow changing physical phenomenon (e.g., it excludes, higher frequency hemodynamic waveform phenomena). To compute elasticity reliably, it is necessary to measure radius, wall thickness and radial displacement, such as in the inventive system. Empirical approximations of stiffness of diagnostic devices (e.g., developed by Hypertension Diagnostics Inc, Pulse Metric, and Vital Insite, Inc.) lack reliability in part by not measuring radius and wall thickness, because normal physiologic variations produce significant variation in measured elasticity.

A fifth innovation of the invention is a full-range elasticity calibration, to minimize or eliminate the need for recalibrations during continuous monitoring, which would otherwise be needed when substantial radius changes occur, as in circulatory shock or with vasoactive drug therapy. This first involves applying a modified Young's elasticity curve $E_{inc}$ that is optionally "tailored" more exactly to the patient data.

$$E_{inc} = \frac{P_{cal}}{\Delta_{cal}} \cdot R_n \cdot \frac{2(1-\sigma^2)R_{n_i}^2}{(R_n^2 - R_{n_i}^2)} \text{ or } |E_{inc}|_{\text{for }\sigma=1/2} = E_y \cdot \left[\frac{3}{2}\frac{(1-\gamma_n)}{(2-\gamma_n)}\right]$$

Research data (for dog femoral arteries with attributes similar to the human brachial, as applies to slow static measurements) supports using a curvilinear approximation that would be consistent with the above research-validated Poisson cuboidal strain deformation from D. H. Bergel in *Static elastic properties of the artery wall*. J Physiology 156:445–69 (1961).

Bergel's version of Young's modulus, however, is inadequate for full-range elasticity monitoring. Young's elasticity, being a tangential strain modulus, becomes inaccurate for larger changes in radius $R_a$ relative to calibration radius $R_n$ because of distortion due to wall thickness change. The invention overcomes this with an application that reflects that wall mass is incompressible (for the range of human physiology). See T. E. Carew, et al. *Compressibility of the Arterial Wall*. Circulation Research, 23:61–68 (1968). With wall tissue volume constant, redistributed wall mass thicknesses $h_a$ can be computed for any artery size with the relationship:

$$\pi \cdot [R_n^2 - (R_n \cdot (1-\gamma_n))^2] = \pi \cdot [R_a^2 - (R_a - h_a)^2]$$

yielding new wall thickness $\gamma_a$:

γ_a=1−mt;epmrl;√1−γinfbeginitalnenditalreset(beginbold2−γendboldinfbeginitalnenditalreset) ·italRmedinfbeginitalnenditalresetsup2resetital/ Rmedinfbeginitalaenditalresetsup2resetrlxmx For practical calibration computation, the above Bergel $E_{inc}$ and wall thickness relationships are combined, to create a full-range, wall thickness-compensated $E_{inc'}$ relationship between elasticity and radius:

$$E_{inc'} = \left[\frac{e^{80 \cdot (R_a - .225)} + 34.286 \cdot R_a - 3.3}{\frac{3}{2} \cdot \left[\frac{1-\gamma_{n'}}{2-\gamma_{n'}}\right]\left[\frac{1-\gamma_{n'}}{\gamma_{n'}}\right]}\right]\left[\frac{1-\gamma}{\gamma}\right]\left[\frac{1-\gamma}{2-\gamma}\right]$$

or, using a practical curve fit approximation of this:

$$E_{inc'} = e^{50.7 \cdot (R_a - 0.2145)} + 0.65$$

The curve-fit version is combined with pressure-elasticity relationships, shown in FIG. 25, that apply Bergel's data. This produces the full-range pressure-radius referencing relationships of FIG. 26. Shift factors are built-in to facilitate iterative computerized calibration curve placement in phase-II when radius monitoring starts. Also, a "final curve tilt" based on the patient's upper and lower range displacement-elasticity differences is an optional part of this phase.

A sixth innovation of the invention is concurrent "multi-variate" sensing, another continuous noninvasive monitoring requirement for avoiding recalibration for changes in elasticity and flow. For example, this is for tracking the reduced pulsatility that usually occurs when radius and elasticity increases (or vice versa), a phenomena that FIG. 26 illustrates. Hemodynamic relationships, disclosed later herein, indicate that such continuous noninvasive monitoring requires, both conceptually and practically, the concurrent sensing of at least two independent physiologic values, and an appropriate computational basis for a third variable. This is because hemodynamics involves three independent dynamic phenomena (pressure, flow and elasticity); with two independent degrees of physiologic measurement, the third independent parameter is computed with a physiologic relationship that is described below.

Without measuring blood flow but still providing reasonable level of reliability for blood pressure monitoring, continuous heart beat-by-beat multivariate sensing enables: (i) quantifying the physical artery pulsatile volumetric displacement amplitude (vda) waveform signal from the cuff signal; (ii) converting the vda into a radial displacement signal; and (iii) measuring radial waveform contours and amplitudes independently of average artery radius and arterial pressure. This involves applying the aforementioned OCD calibrating measures of the cuff, blood pressure, artery radius and artery wall thickness, so as to: (a) determine vda by tracking and fixing cuff air volume and pressure so as to apply the Boyle's application in FIG. 4 (processes 701–703) and FIG. 7 (processes 801–802); (b) track radius $R_{a_i}$ as a simple Boyle's function of the $R_n$ and $\gamma_n$ calibration values (processes 704 and 803); (c) compute radial pulsatility $\Delta$, which is a simple function of vda, radius and cuff-artery length (processes 705 and 804); and (d) compute wall thickness $\gamma_{a_i}$, shown in FIG. 10 process 901.

The seventh innovation of the invention is continuous noninvasive monitoring of the blood pressure waveform contour, which is preferably based on the aforementioned cuff normalization processes, multivariate sensing processes, elasticity measures, and radial displacement conversion ratios that correct for effects of elasticity changes. Research indicates physiologic blood pressure and radial arterial displacement contours are near exact replicas. (Such contour assessments were made without externally compressing the artery, which is not possible with most noninvasive waveform display devices.) See B. S. Gow, et al. *Measurement of viscoelastic properties of arteries in the living dog*. Circ Res. 23:111–22 (1968). However, in the peripheral conduit arteries, such as at the upper limb, abnormal cardiovascular activity or condition, which incident from the heart or emanate as reflectance from the ending arterioles, can and do substantially alter elasticity and radius at the monitoring site. This is preferably implemented with separate lower and upper range pressure displacement scales based respectively on lower and upper range pressure-displacement equations, which compensate for non linearity shown in FIGS. 26 and 27, and are recomputed for each heart beat using current elasticity and radial displacement measures, as described in processes 805–810.

An eighth innovation of the invention is a Newtonian-based blood flow and hemodynamics measurement system with two independent methods of sensing, for more effective patient monitoring and disease management. Provided are invented hemodynamic derivations and methods of applying measures of blood pressure, artery elasticity and blood flow to implement this system. Part of the system is based on the works of several predecessor scientists that started with K. Witzig's 1914 dissertation, *"Uber erzwungene Wellenbewegungen zäher inkompressibler Flüissigkkeiten in elastischen Röhren"*, Bern: Wyss. More important is the related work of J. R. Womersley, who, in the 1950's, published articles describing the mathematics of blood flow. See Womersley's *"Method of Calculating Velocity, Flow and Viscous Drag in Arteries When Pressure Gradient is Known"*, J. Phys. 127: 553–63 (1955).

McDonald, applying Womersley's Poiseuille-based pulsatile flow derivations to pressure waveform gradient measurements in a 1973 study, proved this wall-blood mass interaction technology. (See D. A. McDonald et al., *"Cardiac Output Derived from Time Derivative and Phase Velocities of Aortic Pressure Wave"*, Med Biol Engr, Nov 1973 6:678–90.) McDonald's study tested Womersley's theory by invasively measuring pressure gradient data in dogs, with extreme interventions on the heart (atrial pacing, vagal stimulation and volumetric changes), as well as with powerful peripheral artery vasoactive drug agents, whereby the Womersley-computed flow waveforms and values were compared to simultaneously measured values using invasive electromagnetic flow waveforms and the Fick method. This produced uniquely exceptional clinical flow accuracy, a 0.97 correlation with respect to benchmark data. It confirmed Womersley's mathematical relationships, which take into consideration pressure wave reflectance by computing and applying harmonic phase velocities, a phenomena that has caused unreliability with other blood pressure related systems. It also supported McDonald's contention of this approach's non-susceptibility to "unpredictable changes in wall elasticity . . . due to the catecholamines." Moreover, these results silenced pre-clinical concerns regarding artery elasticity flow energy losses; nearly all of such loss apparently translated into measured changes in the wavefront pressure gradient.

Despite the blood flow accuracy of the McDonald study, the method lacked practicality; it involved positioning a difficult-to-maintain catheter with two independent pressure waveform sensing sites only a few cm apart in the ascending aorta, a system that likely would be kept precise only by scientists and has never been practical for clinical use. The study also involved surgery to measure the external diameter of the aorta, to estimate inner lumen size. No one is known to have created any practical application; any noninvasive implementation of the Womersley/McDonald approach would require measuring or reliably estimating artery bore and pressure gradient, without constricting the artery, which the present invention achieves.

For one sensing mode employed in the invention, elasticity measurement of the invention enables deriving the pressure gradient for applying the Womersley blood flow equations. (In this mode it can be unnecessary to use the P and D Sensors of FIG. 1b.) This overcomes a limitation of past research which did not fully reflect pulsatile artery elasticity effects. Indeed, without knowing artery radius, pulsatile strain and thickness, elasticity still has not been measured in living humans, and non invasive approximations are inaccurate and impractical for clinical use. Moreover, frequency-dependent artery elasticity values, which have been measured in animal research studies, were unsuccessful in reflecting properties typical of other visco-elastic materials. The inventive system includes a method for overcoming these limitations with a flow-based elasticity-pressure relationship and solutioning process that are central to measuring the pressure gradient and other processes of FIGS. 10–18. Simulations using this method indicate that previous elasticity measures were understated at higher frequencies, because simultaneous blood flow effects were not considered. With this flow-based elasticity method, only the single air sensing bladder of a common blood pressure cuff is required (shown in FIG. 1a).

An alternative sensing method of the invention includes two additional cuff sensors, sensor-P and sensor-D, which are positioned, respectively, at proximal and distal artery positions relative to the heart, as shown in FIG. 1b. This alternate, dual blood pressure waveform measurement was similar to the method employed by McDonald in his clinical validation of the Womersley methodology. The processes for this sensing method are in FIGS. 18a and 18b.

Considering the hemodynamics in more detail, the Witzig-Womersley approach applies Newtonian principles to relate flow and pressure. It shows that compensation for flow-mass and artery elasticity is required for fully reliable noninvasive blood pressure measurement. Flow through the arterial system is determined by artery bore, blood viscosity, inertia, artery wall mass constraint, and elasticity (stiffness) energy losses, with about 90% of the variable portion being controlled by auto regulated and wall-thickened constriction at or near the system end point, which generally are arterioles and capillary sphincters that protect the fragile capillary-cellular biologic exchange systems of the body. Elasticity is principally a function of (i) the magnitude of blood mass (e.g., lumen diameter) and its accelerations and decelerations (such velocity changes being dependent on measurement-site lumen size), and (ii) wall distensibility (structure and its muscle tension) and thickness. Pulsatile blood pressure is produced by the frequency-related blood mass interactions with the artery wall. Hemodynamic computations are required because important aspects cannot be approximated using spatial (time-domain) relationships alone.

Womersley hemodynamics hold that blood flow is propelled by a pressure gradient phenomena; arterial blood is momentarily pulsed forward a short distance by the front of the pressure waveform that propagates from the heart many times faster than the flow. Thus, increased propagation velocity would stretch the pressure wave, spreading the pressure change over a longer artery length of blood, to reduce the pressure gradient and flow. This effect would apply to he pressure gradient, dp/dz, the pressure difference in a short artery length. It is defined by the pressure waveform and propagation phase velocity "$\ddot{C}$", with the double-dot notation reflecting applicability in the harmonic domain.

$$\frac{dp}{dz} = -\frac{1}{\ddot{C}}\frac{dP}{dt}$$

Womersley's gradient-flow relationship expands Poiseuille steady-state flow fluidics for the effect of pulsatility using complex Bessel function differential equation solutions to apply Newtonian-based Navier-Stokes equations of motion that add the effects of shear stresses (fluidic friction) of viscous fluids to Euler's equations of motion. This produces intra-arterial velocity profiles of pulsatile oscillatory flows that reflect the effects of blood viscosity, artery lumen size, heart rate inertia; artery wall mass and restrained longitudinal wall movements.

Defined possibly for the first time by Womersley in his 1957 treatise, "*Mathematical analysis of arterial circulation in a state of oscillatory motion*", (Wright Air Development Center Report WADC-TR56-614) is a strain-velocity flow relationship, $$\Delta/R = \dot{V}/\ddot{C}$$

This expression reflects the interaction of blood flow forces (blood mass and its pulsatile velocities) and artery condition (recoil dynamics). It expresses pulsatile strain to be the ratio of blood flow velocity [V] to pressure wave propagation velocity. (Strain is artery radial displacement [$\Delta$] relative to radius, the flow dynamic of greater blood accelerating into, than leaving, any short artery segment.) The relationship shows that displacement and flow decrease with increased propagation velocity (and artery stiffness). Yet this is not simple because the interactions are "dynamic", i.e., frequency-related. Complex solutions are required because arterial waveforms are the sum of the heart-propagated incident waveform and reflected waveforms from the end of the artery tree; this can produce significant variation in harmonic phase velocities, which requires computing individual harmonic component values instead of relying on composite time-domain waveform values.

Womersley's relationship is a part of the invented non-invasive hemodynamics. By measuring $\Delta$ (waveform displacement), R (radius) and $E_y$, for one sensing mode (without using Sensor-P and Sensor-D) the invention computes: (i) "$\ddot{C}$" phase velocities; (ii) phase-corrected pressure gradient waveform; and (iii) the Womersley flow velocity waveforms. To implement, however, required creating a flow-based elasticity relationship, $E_{yf}$, which is described below; this was created by using the $\dot{c}_o$ propagation velocity relationship and a process that solves the incremental viscous-elastic flow-pressure phase velocity, $\Delta \ddot{C}$, for which Womersley's system cannot compensate without the aforementioned parameter values.

$$\Delta \ddot{C} = \ddot{C}/\dot{c}_o$$

where $$\dot{c}'_o = \sqrt{\frac{E_y \cdot \gamma \cdot (2-\gamma)}{3\rho}}$$

The $\dot{c}_o$ propagation velocity relationship (FIG. 29*e*) is well proven, initially by Newton's defining of the velocity of sound in air, as well as with physiologic measurements by several hemodynamic researchers. Specifically, retarded oscillating energy movement in the transverse direction, caused by the relatively greater stiffness recoil of the fluidic medium, is converted into greater longitudinal velocity. Separately, $\Delta \ddot{C}$ reflects blood-wall viscosity effects, and the faster pressure rise relative to blood flow in stiffer arteries.

An invented flow-based elasticity is the first known functional relationship of blood flow, blood pressure and artery elasticity.

$$\ddot{E}_{yf} = \left[\frac{\dot{P}}{\dot{V} \cdot \Delta \ddot{C}}\right]^2 \cdot w$$

Its second-order ratio of pulse pressure to flow velocity, is the dynamic part, whereas [w] encompasses slow changing artery measurement values. Because of phase velocity differences and wave reflectances, $\ddot{E}_{yf}$ cannot be computed with a simple, process. For each heart beat, three FFTs are preferably computed; the first and last FFT are used to derive preliminary and final flow waveforms based on Womersley and pressure gradient waveforms. The second FFT is used to add the effects of harmonic phase velocity to the initial estimated pressure gradient waveform, to derive the final flow waveform. A harmonic solutioning process is used.

It is believed Womersley oscillatory flow relationships, inclusive of average wall mass recoil and longitudinal constraint effects, may not reflect intrinsic cardiovascular stiffness variants as related to aging of structure. Although radial displacement is determinate with the non invasive sensing method of the invention, practical means are needed to reflect longitudinal visco-elastic retardation of flow. This is achieved with a harmonic solutioning process that is performed after each FFT flow waveform derivation, an innovation of the invention.

The harmonic solutioning takes into account that, along with propagating faster with increased elastic modulus, the pressure pulse supervenes more rapidly relative to the pulsatile flow. In addition to the phase velocity effects of inertia, wall-blood viscosity and elastic recoil that Womersley's factors enable computing, the harmonic solutioning determines the blood flow retardation caused by wall recoil stiffnesses and which can be observed in the flow waveform and blood pressure waveform contours. Logically, flow would be expected to occur before pressure, because time transpires before artery recoil reaches maximum. However, testing of the invention shows that it is possible for flow to lag pressure, a reflection phenomena that has also been observed in high flow impedance circumstances by hemodynamic researchers. This can occur because a pressure wave is the sum of incident and reflected pressure wave components from the heart and furthermost arteriole periphery, respectively.

The harmonic solutioning process employs flow-based elasticity computations to determine the viscous, frequency-related effects of blood flow versus artery stiffness. $\ddot{E}_{yf}$ values are based on FFT-computed flow and pressure component sample values at each harmonic frequency, at which it computes and "sifts" through possible solutions until the process identifies the only phasic latency at which flow-based elasticity, pressure and flow correspond in compliance with physical laws. A final harmonic solutioning cycle enables computing phase velocities and accurate FFT-derived pressure gradient and flow velocity waveforms.

This flow-based elasticity aspect of the invention is illustrated in FIG. 29, and is applied generally in processes 901–933, although its execution requires processes of FIGS. 1–9. FIG. 29a summarizes the McDonald/Womersley flow system; examples of a pressure gradient waveform are in FIG. 29b and a corresponding flow waveform in FIG. 29c. The aforementioned Womersley strain-velocity relationship is in FIG. 29d. In an approximative nature, made possible because the inventive system measures arterial pulsatile strain and elasticity modulus and thereby estimates C on a first-pass basis, the system can apply an inventive derivation that is based on Womersley flow mathematics and an inventive harmonic solutioning of the first-known relationship between blood flow, blood pressure and elasticity.

The detailed flow-based elasticity relationship, illustrated in FIG. 29f and FIG. 29h, discloses the relative importance of radius and harmonic elastic stiffness, the principal determinate of blood flow. This partially illustrates, for example, the importance of stiffnesses as the determinant of blood flow at higher blood pressures where radius cannot change appreciably. Yet, this does not reveal the role of the individual $\ddot{E}_{yf}$ frequency component in retarding flow and damaging cardiovascular vessel tissue, which emphasizes the importance of flow waveforms and $\ddot{E}_{yf}$ harmonic values shown in FIGS. 30 and 31.

Additional blood flow measurement computations are applied to increment the positive forward flow of each flow waveform, by the average negative value of the waveform, which is a diastolic retrograde-flow reversal component that was proven to be beneficial in the clinical study of the Womersley method. See McDonald's *Cardiac output derived from time derivative and phase velocities of pressure waves*. Med. Biol Engr. (1973).

A ninth innovation of the invention is a second flow measurement sensing mode, an alternative to flow-based elasticity and its harmonic solutioning for deriving the pressure gradient waveform. This method uses the blood pressure monitoring capabilities of the system, including waveforms sensed through the air pressure of the cuff, to scale calibrate two pressure waveforms sensed a specific distance apart by Sensor-P and Sensor-D on the cuff. This enables measuring harmonic phase directly, rather than relying on harmonic elasticity values. Phase velocities are computed from $$c' = \frac{\omega \cdot \Delta z}{\Delta \varphi}$$

whereby the phase differences $\Delta \varphi$ of the FFT-computed harmonics of the pressure waveform that is measured simultaneously at two points located a fixed distance apart, $\Delta z$, along the artery with sensor-P and sensor-D, with $\omega$ being $2\pi f$ of the heart rate, and performed with processes 958–960 of FIG. 18b, whereupon flow is computed by process 961.

Redundancy monitoring reliability is provided by simultaneously measuring blood flow using both of the aforementioned sensing modes. Also, elasticity can be checked by measuring group propagation velocity between Sensor-P and Sensor-D and using the $\acute{c}_o$ expression (FIG. 29e) to solve Young's elasticity modulus. Differences that develop in these cross-checking "shadow monitoring" processes are bases for system recalibrations in process 1108 of FIG. 20.

The tenth innovation of the inventive system is the application of an alternative pulsatile flow monitoring method that lacks any relationship to Womersley. This method is empirical, although its flow measurements depend on radius and propagation velocity (elasticity), as well as pressure waveform contours that resolve and reveal heart beat-by-beat hemodynamic flow variability, which is needed because the duration of forward flow, the positive contour area, can vary between 10% and 30% of the cardiac heart beat cycle. This approximative method computes flow with the algorithm $$Q_i = \frac{\approx 2R^2}{\acute{c}_o} \cdot Psa_i \cdot \left[1 + \frac{T_s}{T_d}\right]$$

Where Psa is a systolic pressure area portion of a blood pressure waveform (FIG. 33) and other terms are specified in process 1106. It is attributed to H. R. Warner, et. al., *Quantification of beat-by-beat changes in stroke volume from a the aortic pulse contour in man*. J. Appl. Physiol. 5:495. (1953). Prior research applying this correlated with stimulated changes in cardiac output (r=0.97) except for with vasoactive drugs (r=0.7 to 0.77). See N. T. Kouchoukos, et. al., *Estimation of stroke volume in the dog by a pulse contour method*. Circulation Research 26:611–23 (1970). Part of the disparate performance would be because $\acute{c}_o$ (elasticity) and radius were not measured for individual subjects. Another reason would be that the cardiac output stroke volume waveform contour is the average of two types of flow, the stable low resistance flow to the brain and heart that is approximately 30–40% of cardiac output and the 60%–70% of flow that is higher controllable resistance flow that effectively is a "safety reserve" that usually prevents flow being impaired to the brain and heart. Thus, although the cardiac output Psa waveform estimator was not highly specific to vasoactive drug interventions of the Kouchoukos study (e.g., norepinephrine, isoproterenol and Aramine/metaramino were some of the agents that altered peripheral flow resistance and Psa waveform contours), the application of the Psa method at the upper arm reflects peripheral resistance effects more directly, and in conjunction with the Womersley method, may serve to provide enhanced critical care monitoring certainty.

This method is preferably applied as a concurrent "shadow monitoring" method described in process 1106 of FIG. 20. Along with other redundant cross-checked parameters (such as by using the aforementioned Sensor-P and Sensor-D mode), the invented system, which initially calibration-measures patient cardiovascular values, can be made to automatically recalibrate, either (i) when two flow methods disagree, or (ii) based on significant contour changes that indicate elasticity change, whereby radius, elasticity, $\acute{c}_o$ and other parameters can be re-measured as often as is necessary for fully reliable monitoring.

An eleventh innovation of the invention is the measurement of biophysic cardiovascular vessel wall stress. Stresses are tangential circumferential hoop forces that can overdevelop and later damage the tension and ring smooth muscle-elastin structural linkages, respectively, of the conduit artery and arteriole walls. Physiologic simulation data like that shown in FIGS. 30 and 31 suggest that the invented system measures the true extent by which pulsatile harmonic stiffnesses increase with frequency, which challenges McDonald's "unlike any known viscous material" commentary regarding Bergel research that showed limited artery stiffening at higher frequencies. Thus, stress measurement with the inventive system is consistent with the general rule that McDonald promulgated, that "orthodox visco-elastic substance [stiffnesses] rise rapidly with frequency". (See D. A. McDonald's *Blood Flow in Arteries*, pages 268–69). To wit, the simulations suggest that the prior research erred in higher frequency measurements by not properly considering the effects of flow that the inventive system is the first to have performed.

Pursuant to this part of the invention, harmonic stresses are computed by dividing harmonic $E_{yf_H}$ elasticity values by harmonic $\ddot{\Delta}_H/R$ strain values, which are generally most relevant for harmonic frequencies of two to eight times the heart rate. This is performed with process 935 of FIG. 18. Computations using human physiologic parameters show that higher frequency $E_{yf_H}$ values can increase to exceed the limits of cardiovascular structure with stiffer pressure responses, as FIG. 31 indicates. Simulations show excesses worsen greatly with high or spurious heart rates, where harmonic flows are diminished relative to the artery's pressure response. Testing indicates that excessive stiffnesses may occur because of pulsatile flow reductions and timing effects, such as with arrhythmia, LVH disease and increased peripheral resistance, and are an underlying cause of structural alteration and damage. Moreover, and as the possible precursor to the above, prolonged high heart rate stresses of infancy may stimulate greater arteriole wall muscle development and thickness, which, in later life, can cause deterioration of cardiovascular structure and end-stage incidents of heart attacks and strokes.

The twelfth innovation of the invention is a method for improving upon present oscillometric blood pressure measurement accuracy with use of hemodynamics. Without the flow waveform and its relationship to the pressure waveform, non invasive systolic blood pressure accuracy of conventional occlusive cuff determination (OCD) measurement devices can be erroneous by up to approximately 35 mmHg systolic, which can be critical, especially in surgery of patients with cardiovascular disease. These devices ignore error-causing effects of frequency-related timing differences between the instants of peak flow displacement and peak pressure and elasticity stiffness. Variation of flow-pressure phase occurs because of pressure wave reflectances of high systemic resistance, like that which is caused by vasoconstrictive drugs in surgery. Advantageously, the invention applies its frequency-domain hemodynamic phase information to adjust and eliminate this error in processes 925–927 and 929 of FIG. 17.

A thirteenth innovation of the invention is the practical measurement of high flow-state cardiovascular activity. Without this, accuracy of any known noninvasive blood pressure measurement method has depended on measuring only when subjects are completely at rest, which, of no small significance, is unrepresentative of conditions that cause most heart attacks and strokes. Otherwise, exaggerated blood pressure error originates from the artery constriction that a pressurized cuff causes, whereat kinetic flow energy is converted to extra "stagnation" pressure. This is illustrated in FIG. 28. With resting flow this error is only a few mmHg, whereas flow non linearities greatly increase the systolic measurement erroneously by 20–50 mmHg, such as after walking down stairs or a few minutes of exercise or physiologic stress testing. This error also involves conditions that elevate flow like septic shock and anemia, and can be cause of false "white coat hypertension". By measuring blood flow, the invention also includes means of correcting blood pressure stagnation error in process 928–9 of FIG. 17.

The fourteenth innovation is continuous non invasive monitoring of cardiac stroke volume, the body's beat-by-beat blood flow, which, when multiplied by heart rate, is the cardiac output. This is by application of the flow continuity principle, which serves as a solutioning criteria for using the McDonald/Womersley flow technology. By first measuring limb radius, elasticity and limb flow, the flow measurement technology can also be applied, for the same cardiac cycle, upstream at the ascending aorta. This is the main heart output vessel that flows directly at the subclavian artery and to the preferred upper limb monitoring site, the left brachial artery, which is a direct unobstructed path to the heart that is invariably free of disease. The flow continuity principle, described in FIG. 32, is an artery tree mean flow accountability relationship; it is applied to estimate aorta radius based on the relationship of mean flow velocity and a physiologic branching index at the upper limb monitoring site (but which could be modified to apply for other body monitoring sites, such as at the ankle or wrist). The inventive method, illustrated in FIG. 19, consists of first approximating and then successively iteratively re-computing each prior approximated aorta radius, aorta pressure gradient data, Womersley α-parameters, stroke volume (SV) flow waveform and mean flow. This is performed for an individual heart beat until the principle of flow continuity is satisfied, typically requiring between two and six iterations.

A fifteenth innovation of the invention is the practical measurement of blood oxygen perfusion, preferably computed as the product of blood flow and oxygen content or saturation (process 1031 of FIG. 19*a*), where flow is preferably measured using one of the methods described herein (or by other method) and oxygen content is measured with any common noninvasive pulse oximeter or by chemical analysis of venous blood.

A sixteenth innovation of the invention is a pulse oximeter Oxygen Perfusion Latency ("OPL") for warning physicians of the latency of the pulse oximeter measurements. OPL is related to the transport delay time of the oximeter-measured blood oxygen content, which varies in relation to blood flow that is often reduced and can shutdown entirely in surgery. It is the approximate time required for the movement of oxygenated blood from the lungs until the blood reaches the pulse oximeter measurement site at the finger. Exemplary OPL computations in processes 1032–1036 of FIG. 19*a* estimate OPL values by determining the previous beat-by-beat blood flow rates back to the estimated point in time at which the blood exited the lungs or heart, and this is based on geometric parameters of (i) average male adult artery length, which can be optionally factored for user input designations of body size (female, child or infant) for a more exact arterial length of blood transport and (ii) artery bore measurement data.

A seventeenth innovation of the invention is the recording of patient information in a memory device imbedded in or attached to the physiologic sensor (see FIG. 1*a*) for various purposes such as requiring proper replacement of sensors to reduce sepsis and invoicing a user customer for use of sensors or a monitor system. This also is for preventing excessive use of a sensor that has limited physical durability, e.g., a disposable sensor, so that the monitor system can alert the user of a requirement to replace the sensor before sensor system performance might be impaired. Also, after its use, such memory-containing sensor might be given to discharged or physician-examined patients so that this information can be used with another monitor system for follow-up home monitoring. Such memory device can be, but is not limited to being, a low voltage CMOS EEPROM that is accessed with and recorded into by digital signals from the microprocessor of the monitor. Information included can be a sensor type, size and manufacture serial number identifier, patient identification, duration of patient monitoring use, selected patient measurement data and any quality problems.

In a preferred implementation of the invention, three Fast Fourier Transforms (FFTs) are computed for each heart beat; flow waveform FFTs are computed before and after visco-elasticity phase effects are determined by the normalization process which involves FFT-computing the pressure waveform to create a phase-adjusted pressure gradient waveform. During the process, nominal calibration elasticity values (derived from a time-domain method) are modified for the flow-pressure phase variation determined by normalization. Also, independent velocity contour methods provide for pressure "shadow monitoring" (whereby system recalibrations can automatically be effected). The invention can process and display flow velocity and limb pressure waveforms, elasticities, flow resistances, and inner wall flow shear and harmonic circumferential stresses that vary significantly in relation to contour, rate, pressure and stroke/pulse volume. The invention can be advantageously employed, without restriction, for most applications of hospital monitoring, office diagnostic screening, and elevated flow-state (e.g., physicians' physiologic stress testing) uses.

The invention preferably comprises three basic phases—calibration, time—domain monitoring, and frequency-domain monitoring—each of which involve numerous novel aspects. Calibration Phase-I occlusive cuff determination (OCD) processes determine arterial blood pressure and radius. Spatial, time-domain (Td) calibration processes determine radial displacement values at low monitoring cuff pressure, whereby elasticity moduli can be computed for flow relationships and blood pressure monitoring. Frequency domain (Fd) processes initiate blood flow monitoring, calibrate a pressure gradient sampling interval to assure equivalence between Td elasticity and Fd flow-based elasticity parameters, and recalibrate (OCD) systolic blood pressure for effects of classic OCD blood pressure errors that are caused by elevated flow velocity and abnormal flow-pressure phase velocity that occur in critical care measurement conditions. The total calibration takes about 40 seconds, including the Phase-I OCD and Phase-II measurement at the low monitoring cuff pressure.

With limb artery radius and wall thickness determined, all elasticity modulus variables can be determined, whereby a full-range elasticity-compensated pressure and radius calibration relationship provides for continuous Td pressure monitoring at the limb artery site. A calibrated acp signal facilitates monitoring of radius and computation of pulsatile radial distension from the volumetric attributes of a cyclic vda signal associated with each beat. Time-domain pressures are, thus, continuously determined by the elasticity-compensated cal relationship and slower changing artery radius, as well as by the pulsatile vda signal, where this measurement process can also be modified by frequency-domain visco-elastic phase effects that determine flow-retarded peak elasticity and blood flow waveforms.

Frequency-domain processes determine limb artery elastic moduli at each harmonic for which the process is computed, pursuant to the causal flow determinants and artery responses, with pressure being the effect of limb flow, elastic modulus and systemic resistance. Beat-by-beat, sample-level Fd processes determine flow and artery visco-elastic effects that cannot be measured with Td methods, thereby correcting Td-based pressure monitoring accuracy for the effect of visco-elasticity. Fd methods compute harmonic elasticities with substantial independence, thus permitting extended pressure monitoring without recalibration.

With this general background, it is appropriate to now consider specific aspects of the invention, as claimed herein. Accordingly, generally speaking, and without intending to be limiting, one aspect of the invention relates to a method of continuous non invasive, hemodynamic monitoring, comprising: receiving a radius and pulsatile signal related to pressure and its pulsations in a patient's artery; and processing the signal, at least in part in the frequency domain, to obtain pressure and flow waveforms, as well as a composite phase lag between peaks in the pressure and flow waveforms. Processing is performed on a beat-by-beat basis and involves FFT computation of a plurality of harmonic pressure components related to the received pressure signal, preferably at least the first three. Processing may further involve computation of a pressure gradient along the longitudinal axis of the artery, as well as the harmonic components of the computed pressure gradient. These harmonic components may be used to estimate flow velocity, on a harmonic-by-harmonic basis. Processing may also involve computing an estimate of the phase lag between the pressure and flow waveforms, which may be ascertained by: computing, for each harmonic of interest, a plurality of harmonic, flow-based elasticity values, using a plurality of assumed phase shifts; and identifying, for each harmonic of interest, the minimum phase shift which causes the corresponding harmonic components of the pressure and flow-based elasticity waveforms to peak at the same time. Processing may further involve computing a corrected flow velocity waveform, for each harmonic of interest, by adjusting the harmonic components of an initially-computed flow velocity waveform to incorporate the previously-computed minimum phase shift(s).

Again, generally speaking, and without intending to be limiting, another aspect of the invention relates to a method of estimating blood flow velocity, using a noninvasive pressure cuff, comprising: receiving a pulsatile, pressure-related and flow-related signal from the pressure cuff; and computing, for each heartbeat cycle and each harmonic of interest, a first-pass estimate of harmonic phase velocity. Computing the first-pass estimate of harmonic phase velocity, for each harmonic of interest, may involve: computing a first-pass group propagation velocity, the first-pass group propagation velocity being independent of harmonic frequency; and, for each harmonic of interest, adjusting the first-pass group propagation velocity, using harmonic-dependent factors, to produce the first-pass estimate of harmonic phase velocity. The harmonic-dependent factor(s) are preferably non-linear function(s) of, at least, harmonic frequency-dependent, arterial radius-dependent and elasticity-dependent variables, and may include a Womersley modulus and phase factor, computed for each harmonic of interest.

Again, generally speaking, and without intending to be limiting, another aspect of the invention relates to a method of estimating blood flow velocity, using a non invasive pressure cuff, comprising: receiving a pulsatile, pressure-related and flow-related signal from the pressure cuff; computing, at least in part from the pressure-related and flow-related signal, a pressure gradient-related waveform, for each heartbeat cycle; computing harmonic component(s) of the pressure gradient-related signal, for each harmonic of interest; and computing a first-pass estimate of blood flow, for each harmonic of interest, from, at least in part, the computed harmonic component(s). Computing the pressure gradient-related waveform preferably includes computing differences between successive samples of the pressure-related signal; and computing harmonic component(s) of the pressure gradient-related waveform preferably involves an FFT process. Computing a first-pass estimate of blood flow may include computing a plurality of non-linear factors dependent, at least in part, on harmonic frequency, arterial radius and arterial elasticity. Such factors may include, at least, a Womersley modulus and Womersley phase factor, computed for each harmonic of interest.

Again, generally speaking, and without intending to be limiting, another aspect of the invention relates to a method for non invasively determining the longitudinal pressure gradient in a patient's artery, comprising: sampling a pressure-related signal obtained from an externally-mounted pressure-sensitive device; and computing the pressure gradient as a function, at least in part, of the difference between successive samples of the pressure-related signal. The externally-mounted, pressure-sensitive device is preferably an inflatable cuff, wrapped around a limb of the patient and inflated to a monitoring pressure of approximately 10–25 mmHg. The externally-mounted, pressure-sensitive device may also be a plethysmograph. Computing the pressure gradient may further include: computing an estimated propagation velocity from, at least in part, estimates of arterial wall thickness and elasticity; and scaling the successive sample differences in inverse proportion to the estimated propagation velocity and/or in proportion to the sampling rate.

Again, generally speaking, and without intending to be limiting, another aspect of the invention relates to a method for computing blood flow in a patient's artery, from a sequence of cuff pressure samples, comprising: computing, for at least the first three harmonics of the patient's heart rate, a first-pass harmonic phase velocity for each of the harmonic frequencies; computing, from the sequence of cuff pressure samples, a first-pass pressure gradient waveform; computing, for each of the at least first three harmonics, a frequency-domain modulus and phase of the first-pass pressure gradient waveform; computing, for each of the at least first three harmonics, a first-pass harmonic flow waveform from, at least in part, the corresponding frequency-domain modulus and phase of the first-pass pressure gradient waveform; computing, for each of the at least first three harmonics, a first-pass pressure-flow phase shift; computing, for each of the at least first three harmonics, a second-pass estimate of harmonic phase velocity by correcting the corresponding first-pass harmonic phase velocity to account for the corresponding first-pass pressure-flow phase shift; computing a final-pass pressure gradient waveform from, at least in part, the second-pass harmonic phase velocities; and computing a final-pass flow velocity waveform from, at least in part, the final-pass pressure gradient waveform. Computing a first-pass harmonic phase velocity for each of the harmonic frequencies may include: computing a frequency-independent group propagation velocity; and, for each harmonic, adjusting the frequency-independent group propagation velocity, using harmonic-dependent factors, to produce the first-pass estimate of harmonic phase velocity. The harmonic-dependent factors are typically non-linearly dependent on, at least, heart rate, harmonic frequency, arterial radius and arterial elasticity, and preferably include a Womersley modulus and Womersley phase factor, computed for each harmonic of interest. Computing, for each of the at least first three harmonics, a frequency-domain modulus and phase of the first-pass pressure gradient waveform preferably involves an FFT process, but may alternatively involve a DFT (or other transform) process. Computing a first-pass pressure gradient waveform may include computing differences between successive cuff pressure samples, which differences may be scaled by a scaling factor related to the ratio of sampling rate to estimated propagation velocity. Computing the first-pass harmonic flow waveforms may involve, for each harmonic, computing a sinusoidal waveform with frequency equal to the harmonic frequency, magnitude proportional, at least in part, to the corresponding harmonic pressure gradient modulus and phase offset, at least in part, by the corresponding harmonic pressure gradient phase. Computing the first-pass harmonic flow waveforms, for each harmonic, may further involve scaling the magnitude of the corresponding sinusoidal waveform by a corresponding Womersley modulus and offsetting the phase of the corresponding sinusoidal waveform by a corresponding Womersley phase factor. Computing, for each of the at least first three harmonics, a first-pass pressure-flow phase shift may include: computing, for each harmonic, a corresponding harmonic component of the cuff pressure sample waveform; computing, for each harmonic, a plurality of incrementally phase-shifted flow-based elasticity values; and determining, for each harmonic, the first-pass pressure-flow phase shift by identifying the phase-shifted flow-based elasticity values whose peak corresponds most closely, in terms of phase, to the peak of the corresponding harmonic component of the cuff pressure sample waveform. Computing the first-pass pressure-flow phase shifts may further include interpolating, for each harmonic, between the closest matching incrementally phase-shifted flow-based elasticity waveforms to determine the pressure-flow phase shift. Correcting the corresponding first-pass harmonic phase velocity to account for the corresponding first-pass pressure-flow phase shift may include multiplying the first-pass phase velocity by factors related to the first-pass pressure-flow phase shift and the relative position of the pressure peak in the cuff pressure sample waveform. Computing a final-pass pressure gradient waveform may include, for each harmonic: computing a series of harmonic cuff pressure waveform samples; and differencing successive harmonic cuff pressure samples, and scaling the differences by a scaling factor related to the ratio of the sampling rate to the corresponding second-pass harmonic phase velocity, to determine a final-pass harmonic component of the final-pass pressure gradient waveform; then, summing the final-pass harmonic components to determine the final-pass pressure gradient waveform.

Again, generally speaking, and without intending to be limiting, another aspect of the invention relates to a method of non invasively monitoring blood pressure and flow in a patient, comprising: wrapping an inflatable cuff, having predetermined inflation characteristics, around the patient's upper arm or a leg; performing an oscillometric run by inflating the cuff to a flow-occluding pressure, then monitoring pressure pulsations over a series of successively lower inflation pressures; using the predetermined inflation characteristics to convert the monitored pressure pulsations into equivalent volumetric pulsations; determining initial-flow and zero-stress cuff inflation pressures; and determining, at least in part from the initial-flow and zero-stress cuff inflation pressures, parameters related to arterial wall thickness and radius at the zero-stress cuff pressure, and a relationship that enables computing arterial wall thickness and radius at a low cuff pressure which has the effect on the artery of being zero cuff pressure. The method may further include: adjusting the inflation pressure in the cuff to a monitoring pressure of approximately 10–25 mmHg where the computed arterial radius and wall thickness values apply; and determining elasticity at the monitoring pressure.

Again, generally speaking, and without intending to be limiting, another aspect of the invention relates to a method of continuously monitoring a plurality of hemodynamic parameters using a combination of time-domain and frequency-domain processing techniques, the method comprising: computing, on a beat-by-beat basis, at least one (but, alternatively, two, three, four, etc.) time-domain parameter(s), selected from the list of: volume displacement amplitude, average external arterial radius, radial distention, incremental elasticity, relative wall thickness, pulse pressure, pressure gradient, diastolic pressure, systolic pressure, and mean arterial pressure; wherein the at least one time-domain parameter(s) is/are computed using time-domain processing techniques; and computing, on a beat-by-beat basis, at least one (but, alternatively, two, three, four, etc.) frequency-domain parameter(s), selected from the list of: harmonic phase velocity, harmonic pressure gradient, harmonic flow velocity, harmonic flow rate, harmonic flow-based elasticity, and harmonic pressure-flow phase lag; wherein the at least one frequency-domain parameter(s) is/are computed, at least in part, using frequency-domain processing techniques.

Again, generally speaking, and without intending to be limiting, another aspect of the invention relates to a method of continuous, noninvasive patient monitoring, comprising: affixing a cuff to the upper arm or a leg of the patient; performing a system calibration; and entering a beat-by-beat monitoring cycle, which includes providing a real-time blood pressure waveform and providing a real-time blood flow waveform computed, at least in part, in the frequency domain. The monitoring cycle may further include: comparing parameters computed in the time and frequency domain to determine whether a system recalibration is needed; and, if needed, performing a system recalibration. The compared time- and frequency-domain parameters may be related to arterial elasticity. Typically, the real-time blood pressure waveform is computed in the time domain, and may be corrected, for viscous-elastic pressure-flow phase lag, through use of a frequency-domain-computed correction factor.

Again, generally speaking, and without intending to be limiting, another aspect of the invention relates to a continuous, noninvasive, hemodynamic monitoring system, comprising: a pressure transducer, affixed to a patient's upper arm or a leg, providing a signal related to pressure pulsations in a patient's artery; and a signal processor, adapted to process the signal, at least in part in the frequency domain, to obtain pressure and flow waveforms, including a composite phase lag between peaks in the pressure and flow waveforms. The signal processor preferably operates on a heartbeat-by-heartbeat basis, and computes a plurality of harmonic pressure components (preferably, at least the first three) related to the received pressure related signal. The signal processor preferably includes an FFT processor. The signal processor may also include a module programmed to compute a pressure gradient along the longitudinal axis of the artery. The signal processor may also further include a pressure gradient FFT processing module, programmed to compute a plurality of harmonic components of the computed pressure gradient. The signal processor may further include: a flow computation module, programmed to compute an estimate of flow velocity, on a harmonic-by-harmonic basis, using the harmonic components of the computed pressure gradient. The signal processor may further include: a phase lag computation module, programmed to compute an estimate of the phase lag between the pressure and flow waveforms, by: computing, for each harmonic of interest, a plurality of harmonic, flow-based elasticity waveforms, using a plurality of assumed phase shifts; and, identifying, for each harmonic of interest, the minimum phase shift which causes the corresponding harmonic components of the pressure waveforms and flow-based elasticity values to peak at the same time. The signal processor may further include a velocity correction module, programmed to correct the flow velocity waveform(s), for each harmonic of interest, by adjusting the harmonic components of the previously-computed flow velocity waveform to incorporate the previously-computed minimum phase shift(s).

Again, generally speaking, and without intending to be limiting, another aspect of the invention relates to a non invasive system for estimating blood flow velocity, comprising: a pressure cuff, providing a pulsatile, pressure-related signal and a non-pulsatile radius-related signal; and a signal processor, programmed to compute a first-pass estimate of harmonic phase velocity, for each heartbeat cycle and each harmonic of interest. The signal processor may include: a first-pass group velocity computation module, programmed to compute a first-pass group propagation velocity, independent of harmonic frequency; and a velocity-adjustment module, programmed to adjust, for each harmonic of interest, the first-pass group propagation velocity, using harmonic-dependent factors, to produce the first-pass estimate of harmonic phase velocity. The harmonic-dependent factor(s) are typically non-linear function(s) of, at least, harmonic frequency-dependent, arterial radius-dependent and elasticity-dependent variables, and preferably include a Womersley modulus and Womersley phase factor, computed for each harmonic of interest.

Again, generally speaking, and without intending to be limiting, another aspect of the invention relates to a non invasive system for estimating blood flow velocity, comprising: a pressure cuff, mounted to provide a pulsatile, pressure-related signal and a non-pulsatile radius-related signal; a pressure gradient processing module, programmed to compute, using, at least in part, the pressure-related and radius-related signal, a pressure gradient-related waveform, for each heartbeat cycle; a harmonic processing module, programmed to compute harmonic component(s) of the pressure gradient-related signal, for each harmonic of interest; and, a flow processing module, programmed to compute a first-pass estimate of blood flow, for each harmonic of interest, using, at least in part, the computed harmonic component(s). The pressure gradient processing module may compute differences between successive samples of the pressure-related signal. The harmonic processing module may include an FFT processing module. The flow processing module may employ a plurality of non-linear factors dependent, at least in part, on frequency, arterial radius and arterial elasticity. Such factors may include, at least, a Womersley modulus and Womersley phase factor, for each harmonic of interest.

Again, generally speaking, and without intending to be limiting, another aspect of the invention relates to a system for non invasively determining the longitudinal pressure gradient in a patient's artery, comprising: an externally-mounted pressure-sensitive device, providing a pressure-related signal and a radius-related signal; a sampler, connected to provide samples of the pressure-related signal; and a signal processor, programmed to compute the pressure gradient as a function, at least in part, of the difference between successive samples of the pressure-related signal. The externally-mounted, pressure-sensitive device is preferably an inflatable cuff, wrapped around a limb of the patient and inflated to a monitoring pressure of approximately 10–25 mmHg. The externally-mounted, pressure-sensitive device may be a plethysmograph. The signal processor may further include: means (of any sort whatsoever) for computing an estimated propagation velocity from, at least in part, estimates of arterial wall thickness and elasticity; and means (of any sort) for scaling the successive sample differences in inverse proportion to the estimated propagation velocity. The signal processor may further includes means (of any sort) for scaling the successive sample differences in proportion to the sampling rate.

Again, generally speaking, and without intending to be limiting, another aspect of the invention relates to A computer-based system for computing blood flow in a patient's artery, from a sequence of cuff pressure samples, comprising: a first-pass velocity processing module, programmed to compute, for at least the first three harmonics of the patient's heart rate, a first-pass harmonic phase velocity for each of the harmonic frequencies; a first-pass pressure gradient processing module, programmed to computed, from the sequence of cuff pressure samples, a first-pass pressure gradient waveform; a harmonic processing module, programmed to compute, for each of the at least first three harmonics, a frequency-domain modulus and phase of the first-pass pressure gradient waveform; a first-pass flow processing module, programmed to compute, for each of the at least first three harmonics, a first-pass harmonic flow waveform from, at least in part, the corresponding frequency-domain modulus and phase of the first-pass pressure gradient waveform; a visco-elastic shift processing module, programmed to compute, for each of the at least first three harmonics, a first-pass pressure-flow phase shift; a second-pass velocity processing module, programmed to compute, for each of the at least first three harmonics, a second-pass estimate of harmonic phase velocity by correcting the corresponding first-pass harmonic phase velocity to account for the corresponding first-pass pressure-flow phase shift; a final-pass pressure gradient processing module, programmed to compute a final-pass pressure gradient waveform from, at least in part, the second-pass harmonic phase velocities; and a final-pass flow processing module, programmed to compute final-pass flow velocity waveform from, at least in part, the final-pass pressure gradient waveform. The first-pass velocity processing module may include: means (of any sort) for computing a frequency-independent group propagation velocity; and means (of any sort) for adjusting, for each harmonic, the frequency-independent group propagation velocity, using harmonic-dependent factors, to produce the first-pass estimate of harmonic phase velocity. Such factors are typically non-linearly dependent on, at least, heart rate, harmonic frequency, arterial radius and arterial elasticity, and may include a Womersley modulus and Womersley phase factor, computed for each harmonic of interest. The harmonic processing module preferably includes an FFT, DFT, or other frequency-transform processing module. The first-pass pressure gradient processing module may include means (of any sort) for computing differences between successive cuff pressure samples. The first-pass pressure gradient processing module may further include means (of any sort) for multiplying the successive sample differences by a scaling factor related to the ratio of sampling rate to estimated propagation velocity. The first-pass flow processing module may include means (of any sort) for computing, for each harmonic, a sinusoidal waveform with frequency equal to the harmonic frequency, magnitude proportional, at least in part, to the corresponding harmonic pressure gradient modulus and phase offset, at least in part, by the corresponding harmonic pressure gradient phase. The first-pass flow processing module may further include means (of any sort) for scaling the magnitude of each sinusoidal waveform by a corresponding Womersley modulus and offsetting the phase of each sinusoidal waveform by a corresponding Womersley phase factor. The visco-elastic shift processing module may include: means (of any sort) for computing, for each harmonic, a corresponding harmonic component of the cuff pressure sample waveform; means (of any sort) for computing, for each harmonic, a plurality of incrementally phase-shifted flow-based elasticity waveforms; and means (of any sort) for determining, for each harmonic, the first-pass pressure-flow phase shift by identifying the phase-shifted flow-based elasticity value whose peak corresponds most closely, in terms of phase, to the peak of the corresponding harmonic component of the cuff pressure sample waveform. The visco-elastic shift processing module may further include means (of any sort) for interpolating, for each harmonic, between the closest matching incrementally phase-shifted flow-based elasticity waveforms to determine the pressure-flow phase shift. The second-pass velocity processing module may include means (of any sort) for multiplying the first-pass phase velocity by factors related to the first-pass pressure-flow phase shift and the relative position of the pressure peak in the cuff pressure sample waveform. The final-pass pressure gradient processing module may include: means (of any sort) for computing, for each harmonic, a series of harmonic cuff pressure waveform samples, differencing successive harmonic cuff pressure samples, and scaling the differences by a scaling factor related to the ratio of the sampling rate to the corresponding second-pass harmonic phase velocity, to determine a final-pass harmonic component of the final-pass pressure gradient waveform; and means (of any sort) for summing the final-pass harmonic components to determine the final-pass pressure gradient waveform.

Again, generally speaking, and without intending to be limiting, another aspect of the invention relates to a system for noninvasively monitoring blood pressure and flow in a patient, comprising: an inflatable cuff, having predetermined inflation characteristics, wrapped around the patient's upper arm or a leg; an oscillometric control module, programmed to inflate the cuff to a flow-occluding pressure, then monitor pressure pulsations over a series of successively lower inflation pressures; a volumetric processing module, programmed to use the predetermined inflation characteristics to convert the monitored pressure pulsations into equivalent volumetric pulsations; a vda envelope processing module, programmed to convert volumetric pulsations to radial pulsations and determine initial-flow and zero-stress cuff inflation pressures, from the volumetric and radial pulsation data; and an arterial calibration parameter processing module, programmed to determine parameters related to arterial wall thickness and radius, using, at least in part the initial-flow and zero-stress cuff inflation pressures. The system may further include: a pressure servoing module, programmed to adjust the inflation pressure in the cuff to a monitoring pressure of approximately 10–25 mmHg; and an arterial monitoring parameter processing module, programmed to determine arterial radius and elasticity at the monitoring pressure.

Again, generally speaking, and without intending to be limiting, another aspect of the invention relates to a system for continuously monitoring a plurality of hemodynamic parameters using a combination of time-domain and frequency-domain processing techniques, the system comprising: a time-domain processing module programmed to compute, on a beat-by-beat basis, at least one (but, alternatively, two, three, four, etc.) time-domain parameter(s), selected from the list of: volume displacement amplitude, average external arterial radius, radial distention, incremental elasticity, relative wall thickness, pulse pressure, pressure gradient, diastolic pressure, systolic pressure and mean arterial pressure; and a frequency-domain processing module, programmed to compute, on a beat-by-beat basis, at least one (but, alternatively, two, three, four, etc.) frequency-domain parameter(s), selected from the list of: harmonic phase velocity, harmonic pressure gradient, harmonic flow velocity, harmonic flow rate, harmonic flow-based elasticity and harmonic pressure-flow phase lag.

Again, generally speaking, and without intending to be limiting, another aspect of the invention relates to a system for continuous, non invasive patient monitoring, comprising: a cuff affixed to the upper arm or a leg of the patient; a system calibration module; and a beat-by-beat monitoring module, including: means (of any sort) for providing a real-time blood pressure waveform; and means (of any sort) for providing a real-time blood flow waveform computed, at least in part, in the frequency domain. The monitoring module may further include: means (of any sort) for comparing parameters computed in the time and frequency domain to determine whether a system recalibration is needed; and means (of any sort) for performing a system recalibration. The means for comparing may compare parameters related to arterial elasticity. The means for providing a real-time blood pressure waveform preferably operates in the time domain, and may correct for visco-elastic pressure-flow phase lag, through use of a frequency-domain-computed correction factor.

Again, generally speaking, and without intending to be limiting, another aspect of the invention relates to an article-of-manufacture, for use in connection with a computer-based method of continuous, noninvasive, hemodynamic monitoring, the article-of-manufacture comprising a computer-readable medium containing instructions which, when executed, cause the computer to: receive a signal related to pressure pulsations in a patient's artery; and process the signal, at least in part in the frequency domain, to obtain pressure and flow waveforms, including a composite phase lag between peaks in the pressure and flow waveforms.

Again, generally speaking, and without intending to be limiting, another aspect of the invention relates to an article-of-manufacture, for use in connection with a computer-based method of estimating blood flow velocity, using a noninvasive pressure cuff, the article-of-manufacture comprising a computer-readable medium containing instructions which, when executed, cause the computer to: receive a pulsatile, pressure-related signal from the pressure cuff; and compute, for each heartbeat cycle and each harmonic of interest, a first-pass estimate of harmonic phase velocity.

Again, generally speaking, and without intending to be limiting, another aspect of the invention relates to an article-of-manufacture, for use in connection with a computer-based method of estimating blood flow velocity, using a noninvasive pressure cuff, the article-of-manufacture comprising a computer-readable medium containing instructions which, when executed, cause the computer to: receive a pulsatile, pressure-related signal from the pressure cuff; compute, at least in part from the pressure-related signal, a pressure gradient-related waveform, for each heartbeat cycle; compute harmonic component(s) of the pressure gradient-related signal, for each harmonic of interest; and compute an estimate of blood flow, for each harmonic of interest, from, at least in part, the computed harmonic component(s).

Again, generally speaking, and without intending to be limiting, another aspect of the invention relates to methods, systems and articles-of-manufacture that contain or acquire measurements from a pulse oximeter that determines oxygen saturation, $O_2SAT$, for use in connection with computer-based methods of estimating blood flow velocity, blood oxygen perfusion and the perfusion latency, preferably using a non invasive pressure cuff and noninvasive infrared and red light emitting diode (LED) that is integral to a clip-on or tape-on sensor (usually a finger sensor).

Again, generally speaking, and without intending to be limiting, further aspects of the invention relate to systems, methods, apparatus or articles-of-manufacture for non invasively determining one or more oxygen perfusion parameter(s), comprising, for example, the following: utilizing a frequency-domain or shadow monitoring waveform contour process to determine flow at an externally accessible arterial site, acquiring a hemoglobin oxygen saturation measurement, and computing a product of the blood flow and the hemoglobin oxygen saturation measurement. Acquiring the oxygen saturation measurement may involve use of a noninvasive pulse oximeter that measures oxygen saturation of blood hemoglobin using an infrared and red light emitting diode sensor or another generally equivalent sensor. The determination of oxygen perfusion may also depend on other hemodynamic parameters indicative of greater or lesser than normal oxygen utilization, such as blood flow rates and respiratory variation of either or both of the cuff or the oximeter sensor, so as to enable identifying, distinguishing or quantifying greater or lesser than normal oxygen utilization as blood passes through tissue capillaries. Parameter(s) related to the transport of nutrients in or blood components may be measured by biochemical sensing system(s), and may be displayed. An oxygen perfusion latency time may be computed, by, for example: utilizing a frequency-domain or shadow monitoring waveform contour process to determine flow at an externally accessible arterial site; obtaining a noninvasive measurement of oxygen saturation at the externally accessible site; computing an internal radius and mean flow velocity of the artery; and computing a latency parameter related to the total travel time of blood flow from the heart to the externally accessible arterial site.

Again, generally speaking, and without intending to be limiting, another aspect of the invention relates to an article-of-manufacture, for use in connection with a computer-based method for noninvasively determining the longitudinal pressure gradient in a patient's artery, the article-of-manufacture comprising a computer-readable medium containing instructions which, when executed, cause the computer to: sample a pressure-related signal obtained from an externally-mounted pressure-sensitive device; and compute the pressure gradient as a function, at least in part, of the difference between successive samples of the pressure-related signal.

Again, generally speaking, and without intending to be limiting, another aspect of the invention relates to an article-of-manufacture, for use in connection with a computer-based method for computing blood flow in a patient's artery, from a sequence of cuff pressure samples, the article-of-manufacture comprising a computer-readable medium containing instructions which, when executed, cause the computer to: compute, for at least the first three harmonics of the patient's heart rate, a first-pass harmonic phase velocity for each of the harmonic frequencies; compute, from the sequence of cuff pressure samples, a first-pass pressure gradient waveform; compute, for each of the at least first three harmonics, a frequency-domain modulus and phase of the first-pass pressure gradient waveform; compute, for each of the at least first three harmonics, a first-pass harmonic flow waveform from, at least in part, the corresponding frequency-domain modulus and phase of the first-pass pressure gradient waveform; compute, for each of the at least first three harmonics, a first-pass pressure-flow phase shift; compute, for each of the at least first three harmonics, a second-pass estimate of harmonic phase velocity by correcting the corresponding first-pass harmonic phase velocity to account for the corresponding first-pass pressure-flow phase shift; compute a final-pass pressure gradient waveform from, at least in part, the second-pass harmonic phase velocities; and compute a final-pass flow velocity waveform from, at least in part, the final-pass pressure gradient waveform.

Again, generally speaking, and without intending to be limiting, a last aspect of the invention relates to an article-of-manufacture, for use in connection with a computer-based method of noninvasively monitoring blood pressure and flow in a patient, using an inflatable cuff, having predetermined inflation characteristics, wrapped around the patient's upper arm or a leg, the article-of-manufacture comprising a computer-readable medium containing instructions which, when executed, cause the computer to: perform an oscillometric run by inflating the cuff to a flow-occluding pressure, then monitoring pressure pulsations over a series of successively lower inflation pressures; use the predetermined inflation characteristics to convert the monitored pressure pulsations into equivalent volumetric pulsations; convert the volumetric pulsations to radial pulsations, determine initial-flow and zero-stress cuff inflation pressures; and determine, at least in part from the initial-flow and zero-stress cuff inflation pressures, parameters related to arterial wall thickness and radius.

Again, generally speaking, and without intending to be limiting, further aspects of the invention relate to noninvasive methods/apparatus/articles-of-manufacture for measuring physical parameters of an artery by, for example: applying an inflatable cuff around the artery; inflating the cuff to a pressure sufficient to substantially occlude blood flow through the artery; deflating the cuff to ascertain a pressure, F, at which pulsations in said cuff first become detectable; further deflating the cuff to ascertain a pressure, C, at which the rate-of-increase of pulsations in said cuff decreases with further cuff deflation; and using F and C to determine a physical parameter of the artery. Using F and C to determine a physical parameter of the artery may involve using F and C to compute a relative wall thickness of the artery, preferably, but not necessarily, using a linear function of F and C. The methods/apparatus/articles-of-manufacture may further involve (i) using said relative wall thickness to determine an internal and external radius of said artery and/or (ii) using said relative wall thickness and F and C pressures to determine a radius of the artery when the externally-applied cuff pressure is reduced such that the artery is not subjected to flow-occluding conditions and/or related hemodynamic disturbances that can cause significant measurement error. The computed radius without externally-applied cuff pressure and said relative wall thickness may be used to compute a Young's elasticity of the said artery Wall. And, as with the other aspects of the present invention, the methods/apparatus/articles-of-manufacture may be practiced (or realized) using a non-inflating band in place of the inflatable cuff.

Again, generally speaking, and not intending to be limiting, further aspects of the invention relate to methods/apparatus/articles-of-manufacture for noninvasively monitoring blood flow through an artery by, for example: placing a band or cuff around a limb of a patient; undertaking an initial calibration phase by controllably constricting and/or relaxing the band or cuff, while measuring pulsations from said artery; computing, from measurements made during said calibration phase, a plurality of arterial parameters, including parameters related to the internal radius, external radius and elasticity of the artery; adjusting the band or cuff to a reduced pressure or tension where it does not substantially constrict or deform the artery and undertaking a continuous flow monitoring phase by computing blood flow through the artery from pulsations measured with the band or cuff at said reduced pressure or tension. Undertaking an initial calibration phase may involve (i) determining a cuff pressure or band tension at which arterial occlusion occurs and/or (ii) determining a zero-stress cuff pressure or band tension. Undertaking a continuous flow monitoring phase may involve: (i) computing a plurality of harmonic phase velocities, computing a phase-corrected pressure gradient waveform, and computing a flow velocity waveform; (ii) performing at least one (and preferably two) FFT or DFT computation(s) per heartbeat; (iii) independently computing a selected parameter by both time-domain and frequency-domain methods, computing difference(s) between value(s) of said selected parameter computed by said time-domain and frequency-domain methods, and if said difference(s) indicate(s) a need to initiate a recalibration, then initiating a recalibration; and/or (iv) using a Womersley modulus and Womersley phase factor, computed or approximated for each harmonic of interest. Computing said selected parameter by a time-domain method may involve computing a ratio of systolic to diastolic duration.

Again, generally speaking, and not intending to be limiting, further aspects of the invention relate to methods/apparatus/articles-of-manufacture for computing Young's elasticity of an artery from noninvasive measurements by, for example: determining a pulse pressure-related parameter from noninvasive measurements; determining an arterial radius-related parameter from noninvasive measurements; determining an arterial wall thickness-related parameter from noninvasive measurements; determining a pulsatile radial displacement-related parameter from noninvasive measurements; and using said pulse pressure-related, arterial radius-related, arterial wall thickness-related and pulsatile radial displacement-related parameters to compute a Young's elasticity for said artery. The computation of said Young's elasticity may utilize a pressure-flow phase lag-related parameter, which may be estimated using an empirical time-domain relationship or computed through a frequency-domain process (which preferably includes a pressure-flow shift normalization process). The methods/apparatus/articles-of-manufacture may further involve: (i) using the computed Young's elasticity and the wall thickness-related parameter to compute a wall-thickness compensated incremental elasticity that is applicable for large changes in artery radius, (ii) refining said computation of wall-thickness compensated incremental elasticity using at least one empirical shift factor, and/or (iii) refining said wall-thickness compensated incremental elasticity, using at least one empirical shift factor, to be consistent with initial OCD and continuous low-pressure cuff or band calibration measurements for the patient, thereby enabling continuous noninvasive monitoring in which blood pressures and elasticity values can be determined based on changes in artery radius values or other waveform contour parameters that exists with each heartbeat.

Again, generally speaking, and not intending to be limiting, further aspects of the invention relate to methods/apparatus/articles-of-manufacture for computing blood flow in an artery by, for example: using measurements received from a controllably restrictive band or cuff to determine a plurality of calibration parameters; and using measurements received from an invasive pressure sensor, along with said plurality of calibration parameters, to compute blood flow in said artery. The plurality of calibration parameters may be computed, at least in part, from measurements taken during an OCD cycle. Using measurements received from an invasive pressure sensor, along with said plurality of calibration parameters, to compute blood flow may include: (i) computing a pressure gradient waveform; and/or (ii) performing a frequency-domain analysis of data received from said invasive pressure sensor.

Again, generally speaking, and not intending to be limiting, further aspects of the invention relate to methods/apparatus/articles-of-manufacture for continuously and non invasively determining blood pressure by, for example: determining a plurality of radius- and elasticity-related parameters through measurements taken during an OCD cycle; and continuously determining blood pressure from non-occlusive measurements and said radius- and elasticity-related parameters. Continuously determining blood pressure from non-occlusive measurements and said radius- and elasticity-related parameters may further include utilizing at least one flow-related parameter, computed at least in part in the frequency domain from said non-occlusive measurements, to account for pressure-flow phase lag effect(s). The methods/apparatus/articles-of-manufacture for continuous blood pressure determination may be used/performed at an elevated flow or non-resting state.

Again, generally speaking, and not intending to be limiting, further aspects of the invention relate to methods/apparatus/articles-of-manufacture for determining cardiac stroke volume by, for example: utilizing a frequency-domain process to determine flow at an externally accessible arterial site; and iteratively applying a flow-continuity analysis, or flow-resistance circuit concepts, to determine cardiac stroke volume. The methods/apparatus/articles-of-manufacture may further involve determining cardiac output by multiplying said determined cardiac stroke volume by a measured heart rate.

Again, generally speaking, and not intending to be limiting, further aspects of the invention relate to noninvasive methods/apparatus/articles-of-manufacture for determining cardiovascular parameters using, for example: at least one sensor that generates a pulsatile signal based on pulsations in an artery; at least one controllable flow-restrictive member that can be used to selectively limit blood flow through said artery; and wherein the methods/apparatus/articles-of-manufacture are further characterized in that they includes at least two characterizing features selected from the list of: computation of both an internal radius and an external radius of said artery; computation of an elasticity of said artery wall; beat-by-beat computation of blood flow in said artery using a frequency-domain process; beat-by-beat computation of blood pressure in said artery using at least one pressure-flow phase lag correction factor; and beat-by-beat comparison of parameters computed in the frequency and time domains to determine whether system recalibration is needed. The methods/apparatus/articles-of-manufacture may further include at least one more characterizing feature selected from the list of: computation of both an internal radius and an external radius of said artery; computation of an elasticity of said artery wall; beat-by-beat computation of blood flow in said artery using a frequency-domain process; beat-by-beat computation of blood pressure in said artery using at least one pressure-flow phase lag correction factor; and beat-by-beat comparison of parameters computed in the frequency and time domains to determine if system recalibration is needed.

Again, generally speaking, and not intending to be limiting, further aspects of the invention relate to noninvasive methods/apparatus/articles-of-manufacture for non invasively determining cardiovascular parameters by, for example: positioning at least two longitudinally separated sensors along an exterior conduit artery; performing an OCD cycle to determine at least a parameter related to the internal radius of said conduit artery; monitoring, at a low external applied pressure of approximately 10–25 mmHg, pressure pulsations received from said at least two longitudinally separated sensors; and determining, from (i) said monitored pulsations, (ii) said at least a parameter related to the internal radius and (iii) the longitudinal separation between said at least two sensors, additional cardiovascular parameter(s). The additional cardiovascular parameter(s) may include: a pulsatile propagation velocity (which may be used to determine a Young's elasticity), a pressure gradient waveform (preferably determined using, at least in part, frequency domain computations), a flow waveform, systolic pressure, diastolic pressure and/or mean pressure.

Again, generally speaking, and without intending to limit, another aspect of the invention relates to replaceable sensor assemblies for use in connection with non-invasive patient monitoring systems, such as a sensor assembly comprised of: one or more sensor(s) capable of measuring or sensing conditions at the periphery of a patient's body and generating signal(s) in response thereto; an energy pathway capable of connecting the sensor(s) to the patient monitoring system; and one or more non-volatile data storage elements capable of storing information indicative of the age, number of uses, and/or total hours of use of the replaceable sensor assembly. Such sensor assembly may be adapted for use with a non-invasive blood pressure and/or flow monitoring system, and may include at least one pressure sensor and an inflatable cuff. The energy pathway may comprise a tube capable of communicating pressure pulsations from the sensor assembly to the non-invasive monitoring system, and/or one or more conductors or fiber-optic links. The non-volatile storage elements preferably comprise an EEPROM, which is preferably updated by the patient monitoring system each time the sensor assembly is used.

Further aspects of the invention involve electronic or computer data signals produced by, or used in connection with, the systems, method and articles-of-manufacture described above, as well as alternative systems, methods, electronic/computer data signals and articles-of-manufacture comprised of alternative combinations and/or subcombinations of the inventive elements, techniques, and aspects described above and configured to compute, quantify and/or monitor aspects of cardiovascular health or condition.

BRIEF DESCRIPTION OF THE DRAWINGS

Certain aspects of the present invention are depicted in the accompanying drawings, which are intended to be considered in conjunction with the symbol definitions and description below, and which are intended to be illustrative rather than limiting, and, in which:

FIGS. 7–9 provide an exemplary flowchart of a Continuous Blood Pressure Monitoring process, in accordance with the invention;

FIGS. 10–18 display an exemplary flowchart of a Continuous Hemodynamic Monitoring process at the sensor site, in accordance with the invention;

FIGS. 18a and 18b display an exemplary flowchart of a Two-point Pressure Monitoring and Flow Monitoring processes, respectively, in accordance with the invention;

FIG. 29 components contain relationships that illustrate the flow-based elasticity, blood flow and flow impedance aspects of the invention;

| | |
|---|---|
| $\cdots_i$ | Index that indicates a process is performed, or a relationship is computed, successively for each heart beat waveform as they occur. |
| $\cdots_H$ | Index that indicates a process is performed, or a relationship is computed, for each of at least the three lowest harmonic FFT or DFT components, and preferably for at least the ten lowest of such components. |
| T | The temperate of air in the measuring cuff. |
| HR | Heart rate (in beats/minute). |
| SR | Sampling rate (in samples/second). |
| t | $t = 0, \frac{1}{SR}, \frac{2}{SR}, \ldots$ <br> Actual time, measured from the beginning of the waveform or beat cycle. Because of the sampling nature of the system, continuous variables that are measured (e.g., pressure, volume) or computed (e.g., flow velocity) as functions of time will only be valid at sampled points (e.g., where ). |
| $p_i(t)$ | Cuff pressure sample values for heart beat i. Valid only at sampled points. |
| $v_i(t)$ | Cuff volume samples for beat cycle i. Valid only at sampled points. |
| $p_{t_i}$ | Lowest ("trough") pressure sampled from the cuff during heart beat i |
| $p_{p_i}$ | Maximum ("peak") pressure sampled from the cuff during heart beat i |
| $P_i$ | Pulse pressure, for heart beat i, defined as peak systolic pressure minus trough, resting diastolic pressure. |

-continued

Figure 21:
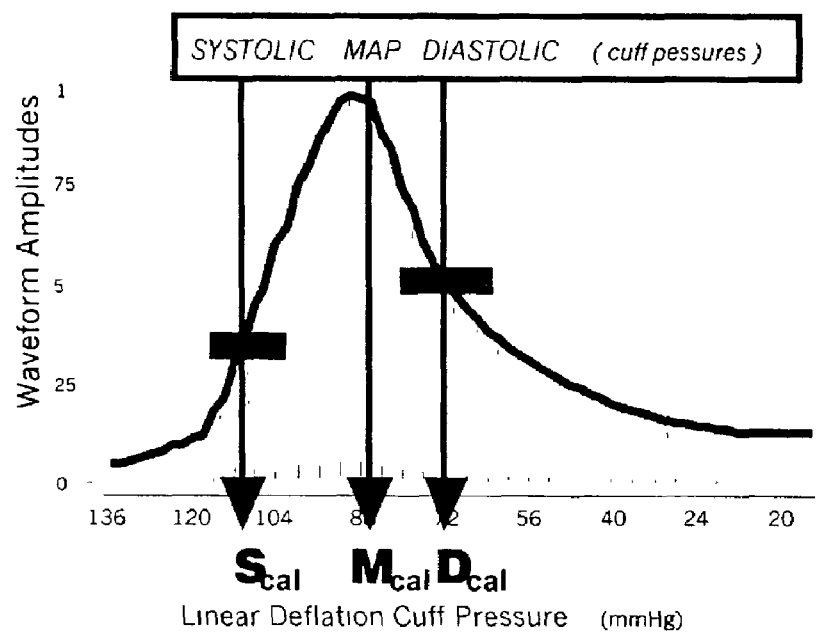
FIG. 21 contains an exemplary waveform envelope, illustrating the basis for a blood pressure estimate in the calibration process of the invention.

| | |
|---|---|
| $\overline{p}_{2\_sec_i}$ | 2-second moving average of cuff pressure samples measured during, and prior to, heart beat cycle i. |
| $\overline{A}_{cal}$ | 2-second moving average of cuff volume samples measured during, and prior to, heart beat cycle i. |
| $vda_i$ | Composite volume displacement amplitude; for heart beat i. |
| $acp_i$ | Average cuff pressure for heart beat i |
| $L_c$ | "Effective artery-cuff contact length," that enables normalizing the signal by removing cuff size and placement differences; derived from measuring pressure and air flow volumes during calibrating cuff OCD and comparing measured values with stored reference values. |
| $MAP_{cal}$ | Calibration-phase mean arterial pressure, estimated from the vda envelope using an oscillometric method depicted in FIG. 21. |
| $S_{cal}$ | Calibration-phase systolic pressure, calculated from the vda envelope. |
| $D_{cal}$ | Calibration-phase diastolic pressure, calculated from the vda envelope. |
| F | Calibration-phase initial flow pressure, calculated from the vda envelope. Represents the cuff pressure at which, during successive deflation from occlusion, flow in the artery first becomes detectable with a rapid ascent in vda values. |
| C | Calibration-phase cuff pressure; used to determine artery zero-stress cuff pressure, where the slope of the vda envelope first exhibits a decreased rate of increase as cuff pressure decreases. |
| $vda_{zs}$ | Volume displacement amplitude of the waveform at the zero-stress cuff pressure. |
| $\gamma_n$ | Calibration-phase relative wall thickness, calculated from vda envelope-derived parameters, and defined as the ratio of arterial wall thickness to external radius. |
| $R_n$ | Calibration-phase external radius. |
| $R_{a_i}$ | Average external artery radius during beat i, based on a slow two-second average cuff pressure relationship and Boyle's principle. |
| $R_{ai_i}$ | Average internal artery radius during beat cycle i; computed based on $R_{ai}$, using an artery wall-mass relationship. |
| $r_{p\_zs}$ | Peak pulsatile zero-stress radial amplitude. |
| $ACP_{cal}$ | Average cuff pressure, during a brief (e.g., six beat) calibration sequence, with the cuff at low (10–22 mmHg) monitoring pressure. |
| $CV_{cal}$ | Average cuff volume, during the same calibration sequence, also while the cuff is at monitoring pressure |
| $vda_i(t)$ | Volumetric displacement waveform for heart beat cycle i, which represents the physically displaced cuff air equivalence of the artery pulsation between the resting diastolic and peak systolic phases. |
| $\Delta_{mean_i}$ or $\overline{\Delta}_i$ | Mean radial waveform displacement for heart beat i |
| $\Delta_{peak_i}$ | Peak radial displacement for heart beat i. |
| $\Delta_{cal}$ | Average radial displacement during a relatively-short (e.g., six beat) calibration period. |
| $\Delta_{\Delta\_cal}$ | Estimated pressure-flow phase lag correction factor. (Used when no actual phase-lag estimate is available, e.g., when frequency domain processing is not enabled.) |
| $\Delta_{\phi_i}$ | Pressure-flow phase lag correction factor, for heart beat i |
| $\tau$(stress) | Biophysical stress is the circumferential force that is distributed through elements of wall material (elastin-smooth muscle and their linkages). At higher frequencies, testing indicates stresses can exceed research estimated arterial stress limits, by several orders of magnitude: |
| $\epsilon$ (strain) | Strain is relative radial artery displacement, $\Delta/R_a$. When sampled, it describes a pressure waveform contour, as confirmed in various research studies, including Womersley's work cited by McDonald. |
| $E_y$ | Young's incremental tangential elasticity modulus, a time domain version. This is a measure of the ratio of biophysical stress (force distribution in artery wall tissue) to strain (radial distension relative to radius), or $\tau/\epsilon$. This is an invalid measure for large changes in radius, without a correction for attendant wall thickness changes. This measure represents average tangential or circumferential stiffnesses of an artery vessel, |

-continued

| | |
|---|---|
| $E_{inc}$ | ignoring faster harmonic stiffnesses that the invented system show to be substantially greater. With compensation for wall-thickness changes that occur with changes in radius, this incremental elasticity modulus is effective for continuous monitoring when large blood flow changes occur. |
| $E_{y_i}$ | Young's elasticity modulus for heart beat i. |
| $E_{inc_i}$ | Corrected incremental elasticity modulus for heart beat i. |
| $O_p$ and $O_{ra}$ | Computer effected shift factors to position pressure-elasticity and pressure-radius calibration curve for continuous monitoring. |
| $P_{a_i}$ | Average pressure of heart beat i. |
| $\hat{p}_{i(t)...for M+}$ | Calibrated blood pressure waveform sample values greater than M blood pressure for heart beat i. (Valid only at sampled points.) |
| $\hat{p}_{i(t)...for M-}$ | Calibrated blood pressure waveform sample values less than M blood pressure during heart beat i. (Valid only at sampled points.) |
| $P_i$ | Pulse pressure for heart beat i. |
| $\overline{P}_{cal}$ | Average pulse pressure during a short (e.g., six beat) cal period. |
| $sp_{P_i}(t)$ and $sp_{D_i}(t)$ | Unscaled signals of $i_{th}$ pressure waveform produced by sensor-P and sensor-D |
| $sp_{P_{mn_i}}(t)$ and $sp_{D_{mn_i}}(t)$ | Mean of $i^{th}$ unscaled pressure waveform produced by sensor-P and sensor-D |
| $\hat{p}_{P_i}(t)$ | Calibrated pressure waveform signal from sensor-P, the proximal cuff sensor (FIG. 1b), for the $i^{th}$ heart beat. |
| $\hat{p}_{D_i}(t)$ | Calibrated pressure waveform signal from sensor-D, the distal cuff sensor (FIG. 1b), for the $i^{th}$ heart beat. |
| $M_{\hat{p}_{P_i}}$ and $M_{\hat{p}_{D_i}}$ | FFT modulus of the pressure waveforms $\hat{p}_{P_i}(t)$ and $\hat{p}_{D_i}(t)$. |
| $\varphi_{\hat{p}_{P_i}}$ and $\varphi_{\hat{p}_{D_i}}$ | FFT phase of the pressure waveforms $\hat{p}_{P_i}(t)$ and $\hat{p}_{D_i}(t)$. |
| $\Delta t_i$ | Time of $i^{th}$ waveform peak travel between sensor-P and sensor-D. |
| $c_{o_i}^x$ | Group propagation velocity of $i^{th}$ waveform between sensor-P and sensor-D. |
| $P_{o_i}^x$ | Pulse pressure of $i^{th}$ waveform attributable to $c_{o_i}^x$ artery elasticity, radius and displacement between sensor-P and sensor-D |
| $\lfloor \Delta\varphi_{\hat{p}_{P_i}} \rfloor_H$ | Phase difference of $i^{th}$ waveform between sensor-P and sensor-D. |
| $\lfloor c'_{\hat{p}_{P_i}} \rfloor_H$ | Harmonic phase velocity of $i^{th}$ waveform using two-point method. |
| $\nabla \hat{p}_{P_i}(t)$ | Pressure gradient waveform at sensor-D using two-point method. |
| $\hat{Q}_{P_i}(t)$ | Flow waveform of $i^{th}$ beat derived by two-point Womersley method |
| $[\ ]_H$ | Notation meaning: "evaluated for harmonic H." |
| $\sum_H$ | Notation meaning: "summed over all evaluated harmonics." |
| $f_H$ | Frequency of harmonic H. |
| $\alpha$ | Womersley kinematic parameter, with $\alpha_H$ applying for harmonic H. |
| $\mu$ | Viscosity of blood |
| $\rho$ | Density of blood. |
| $\sigma$ | Poisson's Ratio of transverse to longitudinal strain, is the extent that a material becomes narrow when it is stretched in length. |

-continued

| | |
|---|---|
| $M'_{10}$ | Womersley modulus, and its designation for harmonic number H. |
| $[M'_{10}]_H$ | $M'_{10}$ and $e'_{10}$ below are pre-computed Bessel moduli and phase function parameters for that describe inertia, capacitance, wall conditions and other factors that define the flow waveform. |
| $e'_{10}$ $[e'_{10}]_H$ | Womersley phase and its designation for harmonic component H. |
| $E_{yf_i}$ | First-pass, composite, flow-based elasticity, for heart beat i. |
| $\lfloor E_{yf_i}(t) \rfloor_H$ | Harmonic component of first-pass, flow-based elasticity waveform, for heart beat i. Only valid at sampled points; $t = 0, \frac{1}{SR}, \frac{2}{SR}, \ldots$ |
| $\hat{E}_{yf_i}$ | Final-pass, composite, flow-based elasticity, for heart beat i. |
| $\lfloor \hat{E}_{yf_i}(t) \rfloor_H$ | Harmonic component flow-based elasticity samples (e.g., for) of final-pass, solution, for heart beat i ... $t = 0, \frac{1}{SR}, \frac{2}{SR}, \ldots$ |
| $\langle E_{yf} \rangle_3$ | Moving average of last three computed values of composite, flow-based elasticity. |
| $c'_{o_i}$ | Group propagation velocity estimate for $i^{th}$ waveform. (Includes effects of blood viscosity and wall thickness, but not viscous wall pressure-flow phase lag.) |
| $\lfloor C_{1_i} \rfloor_H$ | First-pass estimate of a harmonic component phase velocity for heart beat waveform i. |
| $[\Delta C \alpha_i]_H$ | First-pass estimate of part of composite waveform phase velocity, for beat cycle i. Applies Womersley blood-wall resistance to $c'_o$. |
| $\nabla p_i(t)$ | First-pass estimate of pressure-gradient waveforms. |
| $\nabla \hat{p}_i(t)$ | Final-pass pressure-gradient waveform for heart beat i. |
| $\lfloor M_{\nabla p_i} \rfloor_H$ | FFT modulus, for harmonic component H, of the first-pass pressure gradient waveform i. |
| $\lfloor M_{\nabla \hat{p}_i} \rfloor_H$ | FFT modulus, for harmonic component H, of the final-pass pressure gradient waveform i. |
| $\lfloor \phi_{\nabla p_i} \rfloor_H$ | FFT phase, for harmonic component H, of the first-pass pressure gradient waveform i. |
| $\lfloor M_{\hat{p}_i} \rfloor_H$ | FFT modulus, for harmonic component H of the blood pressure waveform i. |
| $\lfloor \phi_{\hat{p}_i} \rfloor_H$ | FFT phase, for harmonic component H, of the blood pressure waveform i. |
| $Z_{cal}$ | Pressure gradient measurement length; single point method. |
| $\Delta z$ | Pressure gradient length between sensor-P and sensor-D using two-point method. |
| $[V_i(t)]_H$ | First-pass estimate of flow velocity waveform i. |
| $\hat{V}_i(t)$ | Pressure-flow phase-lag corrected flow velocity waveform i. |
| $\lfloor \hat{V}_i(t) \rfloor_H$ | Harmonic component of pressure-flow phase-lag corrected flow velocity waveform i. |
| $t_{V_{i\_max}}$ | Time (from beginning of waveform) of peak first-pass flow sample, during beat cycle i. |
| $t_{\hat{V}_{i\_max}}$ | Time (from beginning of waveform) of peak final-pass flow sample. |
| $t_{\hat{p}_{i\_max}}$ | Time (from beginning of waveform) of peak pressure sample. |
| $[\ ]_{\rightarrow X}$ | Notation meaning: "waveform phase shifted by X radians." |
| $\Delta C \alpha_i$ | Composite first-pass Womersley propagation velocity correction. |
| $\lfloor \phi_{N_i} \rfloor_H$ | First-pass viscous artery harmonic pressure-flow phase lag for heart beat i. |
| $\lfloor \hat{\phi}_{N_i} \rfloor_H$ | Final viscous artery harmonic pressure-flow phase lag for heart beat i. |

| | |
|---|---|
| $[C_{2_i}]_H$ | Phase-compensated propagation velocity of harmonic component H, for heart beat i. |
| $[\hat{p}_i(t)]_H$ | Harmonic component (H) of the blood pressure waveform i. |
| $HO_i$ | Hemoglobin oxygen volumetric content |
| $OP_i$ | Oxygen perfusion, the ml of oxygen transported in blood |
| $O_2SAT_i$ | Hemoglobin oxygen saturation % measured by pulse oximeter |
| $OPL_i$ | Oxygen Perfusion Latency time for blood to reach the pulse oximeter measurement site from the approximate time of blood oxygenation in the patient lungs. |

DESCRIPTION OF THE PREFERRED EMBODIMENT

Figure 1:
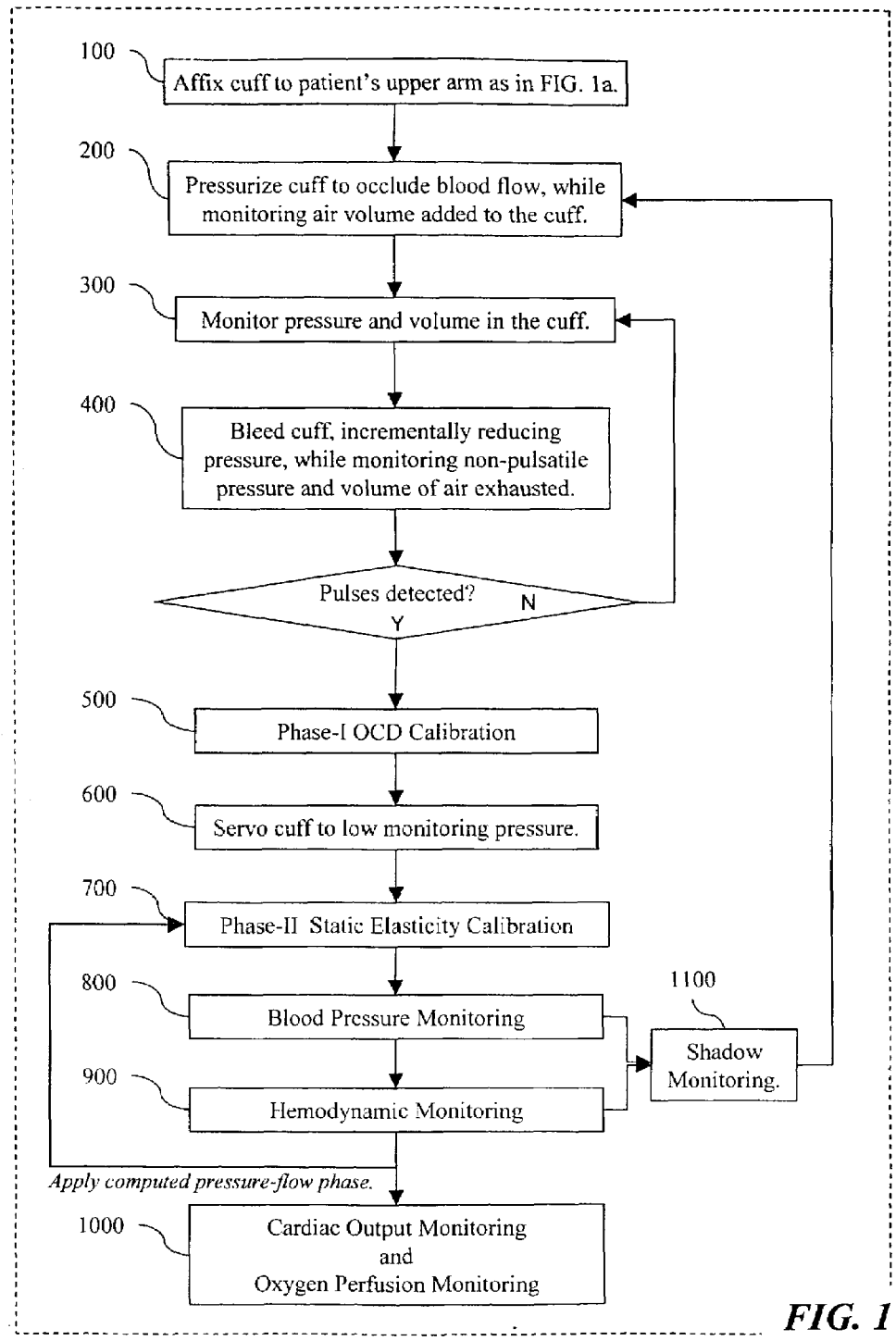
FIG. 1 contains an exemplary flowchart of an overall flow-monitoring system, in accordance with the invention.
Figure 1A:
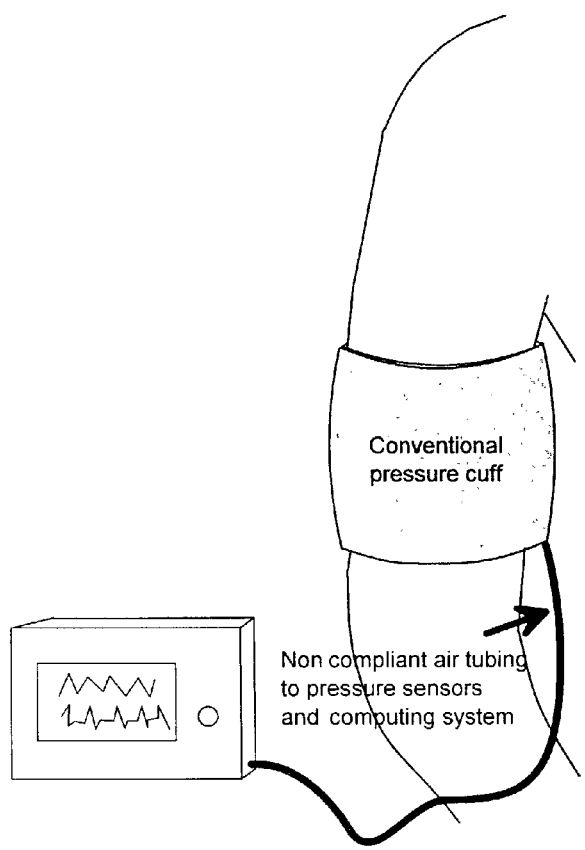
FIG. 1a describes the placement of a sensor cuff
Figure 1B:
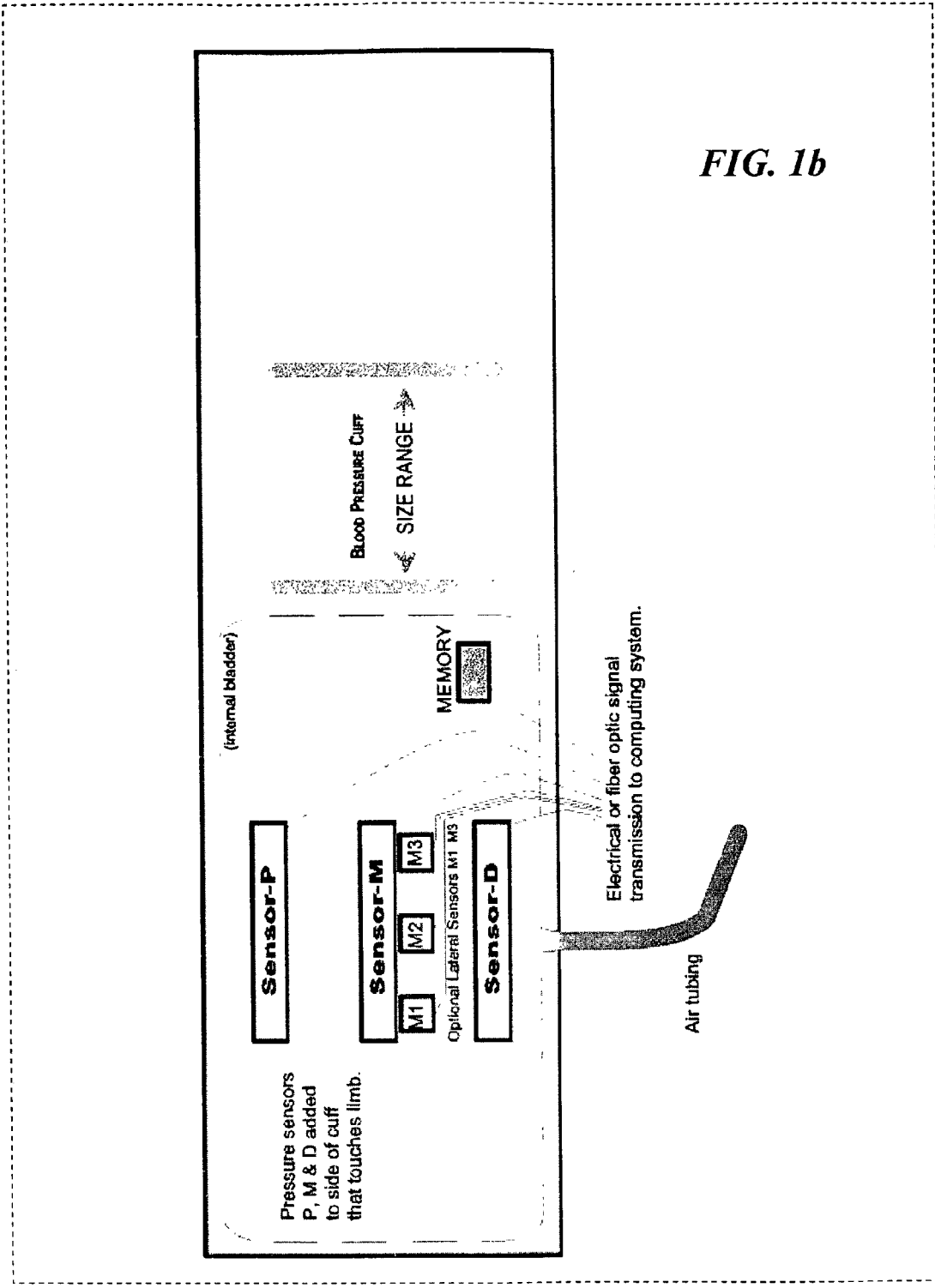
FIG. 1b describes the sensor configurations of a sensor cuff

Referring initially to FIG. 1, which depicts the overall operational flow of an illustrative embodiment of the invention, the process begins by affixing 100 a pressure cuff (or other pressure-sensing device) to a patient's upper arm as described in FIG. 1a and FIG. 1b. The cuff is then inflated 200 to a pressure sufficient to occlude flow in the patient's brachial artery. During this inflation process, volume and pressure of air (or other gas) in the cuff is monitored 200. The volume air in the cuff is then slowly reduced 400 until the point at which pressure pulsations in the cuff become detectable.

Following this initialization phase, the system preferably performs a Phase I (or OCD) calibration 500, servos 600 the cuff to a reduced monitoring pressure, performs a Phase II static elasticity calibration 700, and initiates continuous blood pressure 800, hemodynamic 900 and cardiac output 1000 monitoring activities. The system may further perform shadow monitoring 1100 using predominantly independent methods; if a need for recalibration is detected, the system repeats one or more the above-noted initiation and/or calibration activities.

Figure 2:
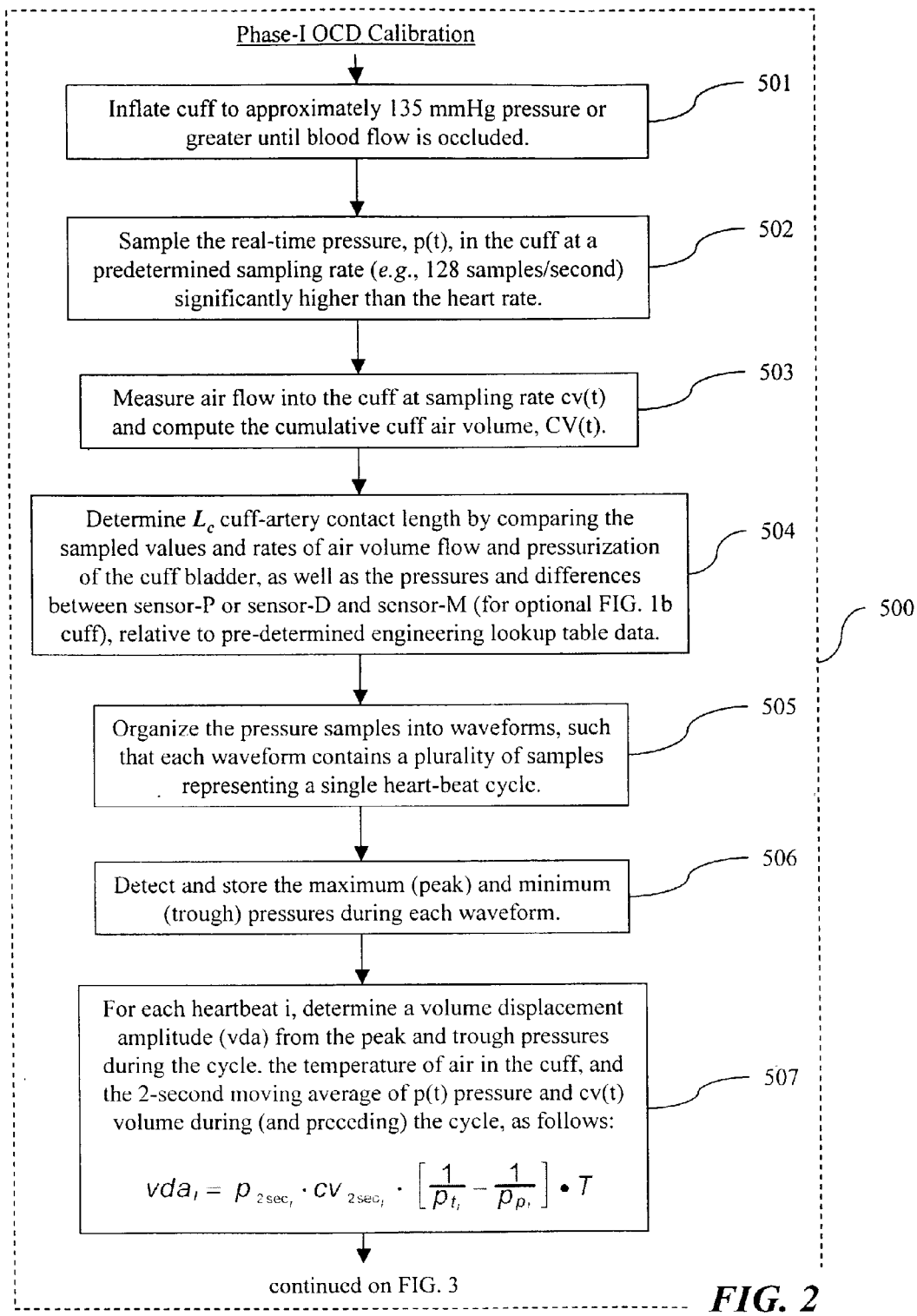
FIGS. 2–3 provide an exemplary flowchart of a Phase-I OCD Calibration process, in accordance with the invention.

Reference is now made to FIG. 2, which shows, in flowchart form, portions of an exemplary Phase-I calibration process 500. The depicted process begins by initially inflating 501 the cuff sufficiently to occlude blood flow in the underlying artery, and initiating real-time sampling 502 of cuff pressure pulsations at a rate sufficient to capture a reasonable amount of waveform detail. Such sampling preferably further includes real-time measurement (or computation) 503 of the rate of air flow into the cuff, and/or the cumulative volume of air in the cuff. This data is used 504 to ascertain an effective cuff-artery contact length, by comparing the sampled data with previously stored reference data.

Sampling continues over a plurality of heartbeats, and the sampled data is organized 505 into successive waveforms, each of which represents a single beat. For each of these waveforms, peak and trough pressures 506, as well as a volume displacement amplitude ("vda") 507, are determined.

Figure 3:
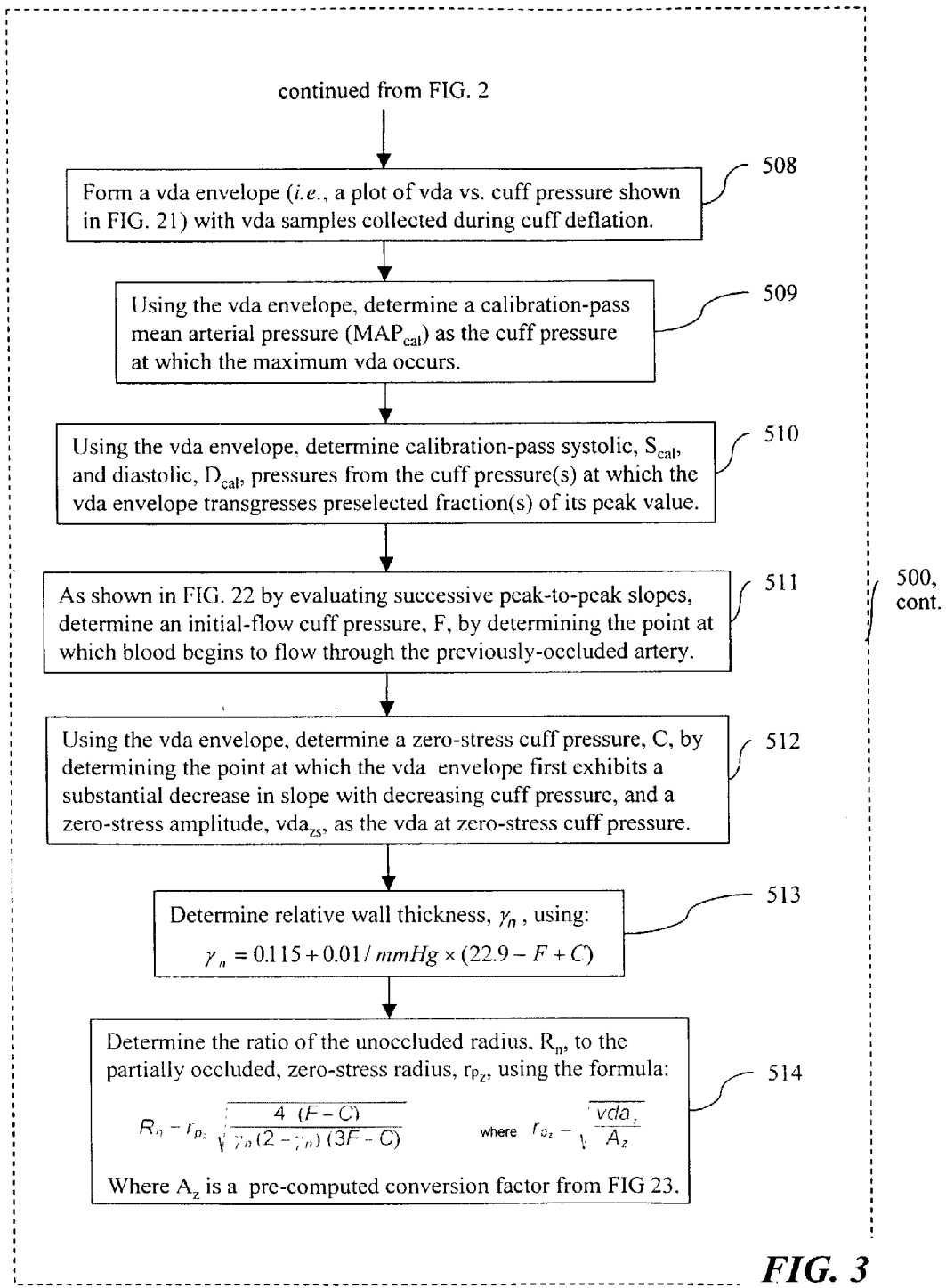
Figure 22:
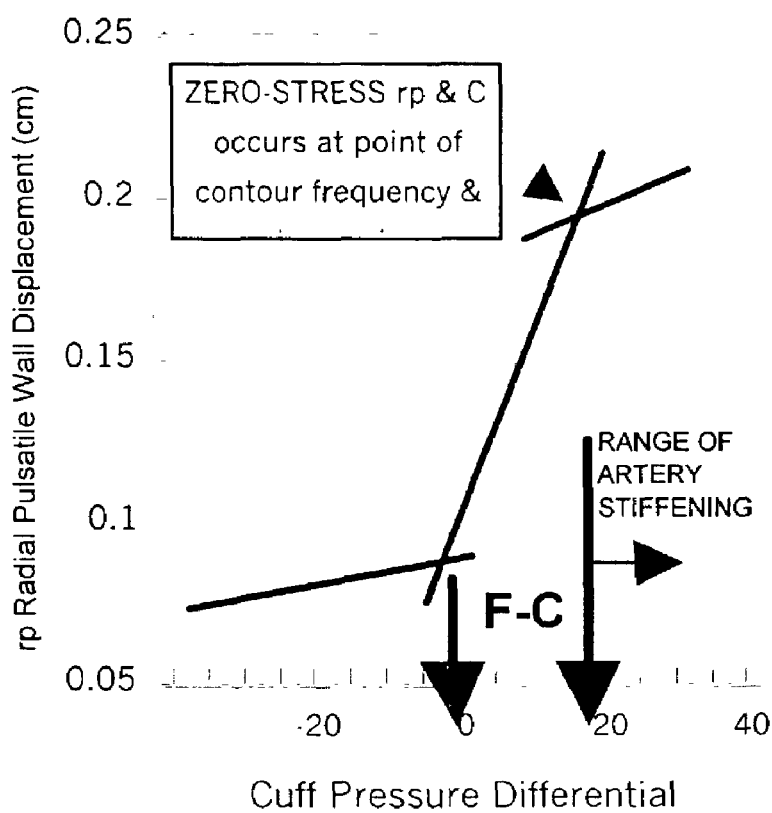
FIG. 22 contains an exemplary radial displacement envelope to illustrate how artery radius and wall thickness are determined in connection with the invention.
Figure 23:
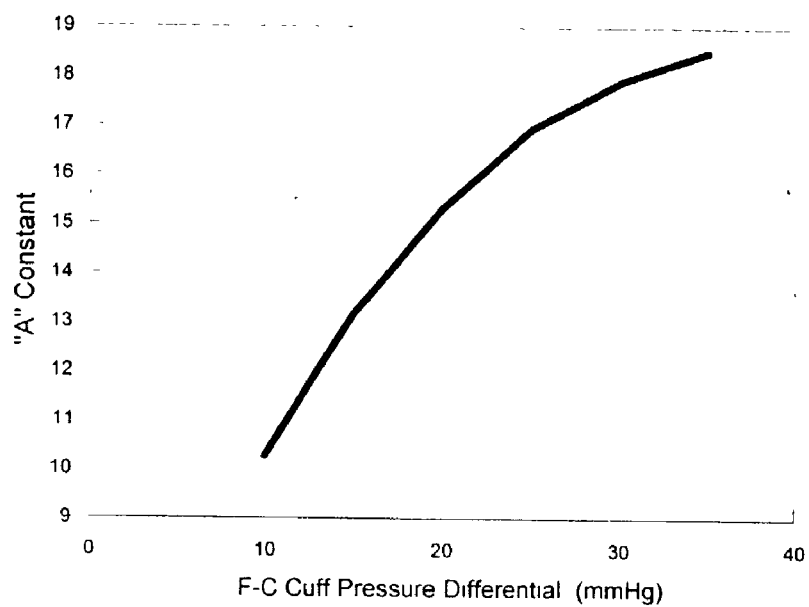
FIG. 23 contains an exemplary conversion factor graph that can be used for converting from volumetric to radial signal values in connection with the invention.
Figure 24:
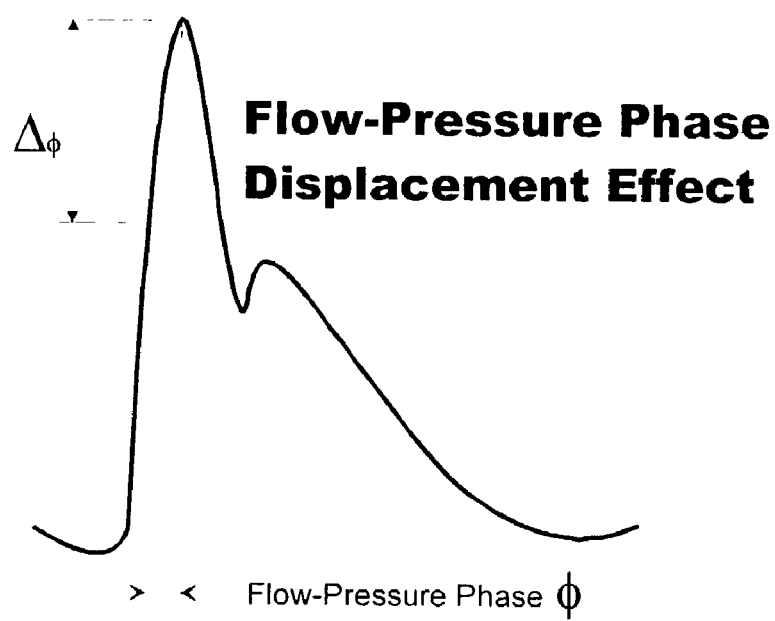
FIG. 24 contains an exemplary pressure displacement waveform, graphically illustrating the determination of radial displacement differential related to flow-pressure phase.

Referring now to FIG. 3, which shows a continuation of exemplary process 500, sampling and vda computations continue, while the cuff undergoes successive incremental deflations, to obtain an overall 508 vda envelope. (An exemplary vda envelope appears in FIG. 21.) This vda envelope is used to derive initial estimates of mean arterial pressure 509, as well as systolic and diastolic pressures 510. Further, initial flow cuff pressure 511 and zero-stress cuff pressure 512 parameters are determined. See FIG. 22. These calibration parameters are, in turn, used to compute 513 relative artery wall thickness and 514 unoccluded external artery radius, thus concluding the exemplary Phase-I calibration process.

Figure 4:
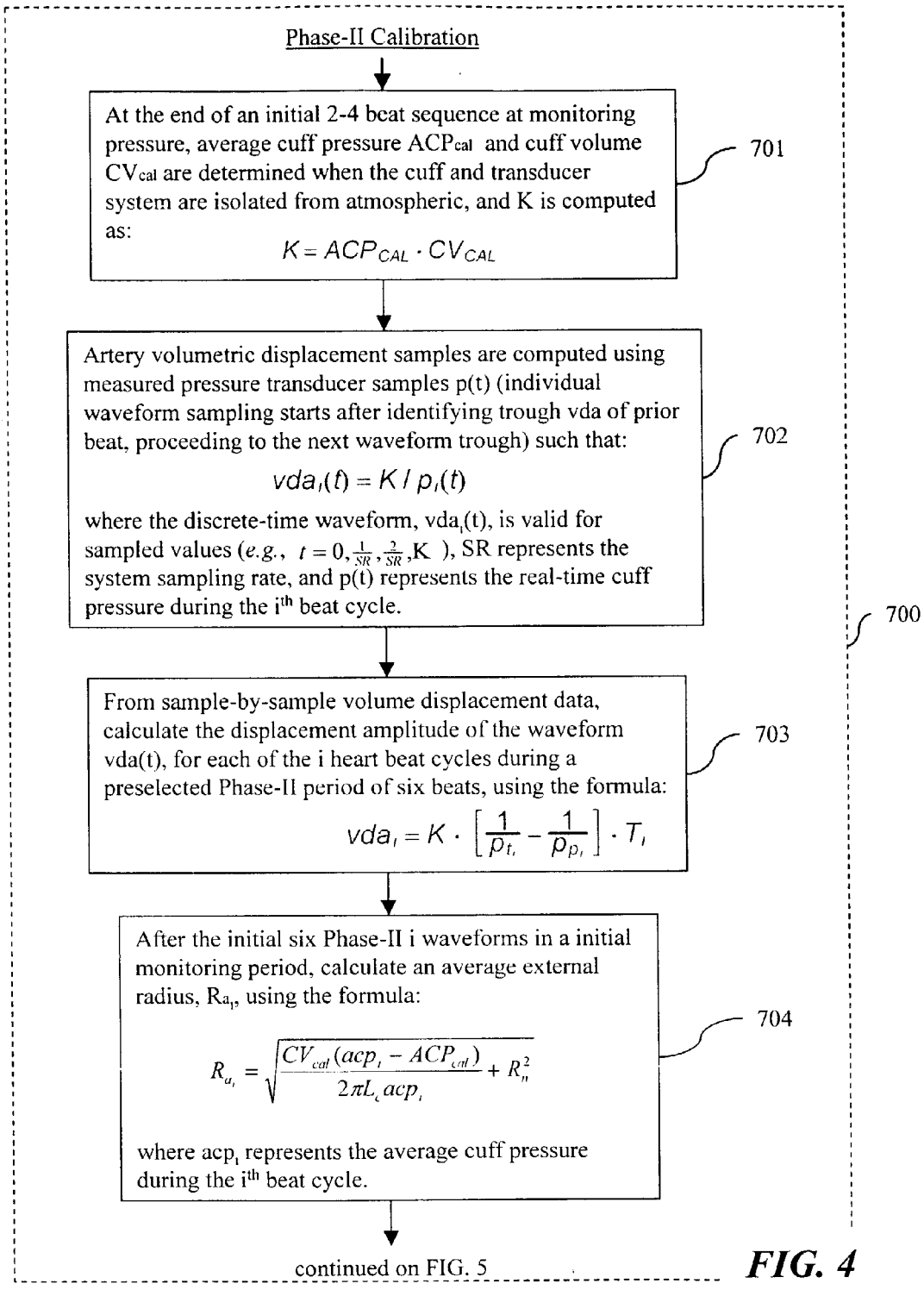
FIGS. 4–6 contain an exemplary flowchart of a Phase-II Static Elasticity Calibration process, in accordance with the invention.

Referring now to FIG. 4, which shows aspects of an exemplary Phase-II calibration process, exemplary process 700 begins by determining 701 a pressure-volume constant K that applies to the cuff sensing system until a recalibration is started or the patient monitoring is ended. The determined K is then used to construct a sample-by-sample vda waveform 702 and a vda amplitude 703 for each beat during the Phase-II process. After several beats (preferably about six), external radius computation 704 is initiated.

Figure 5:
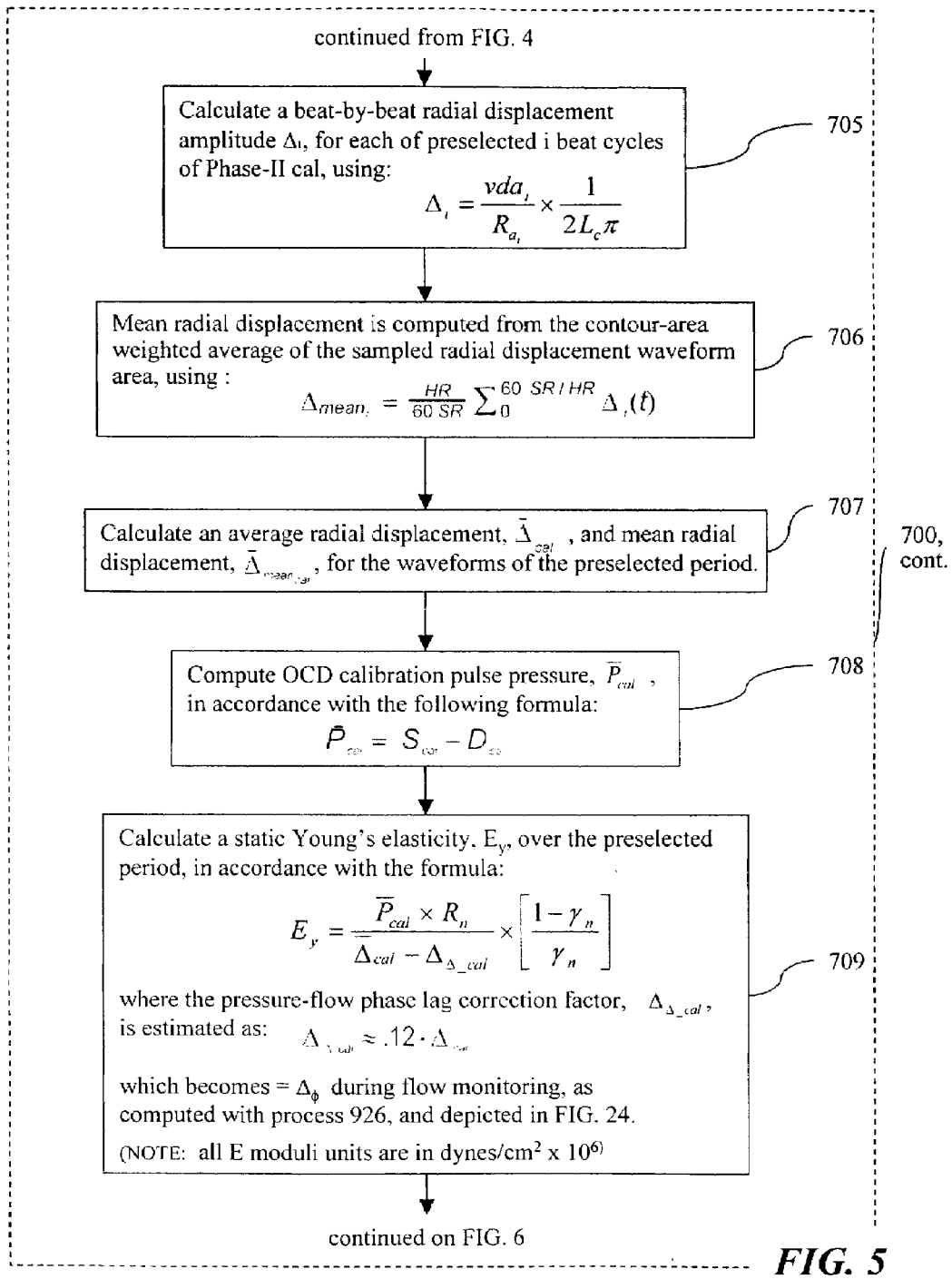
Figure 6:
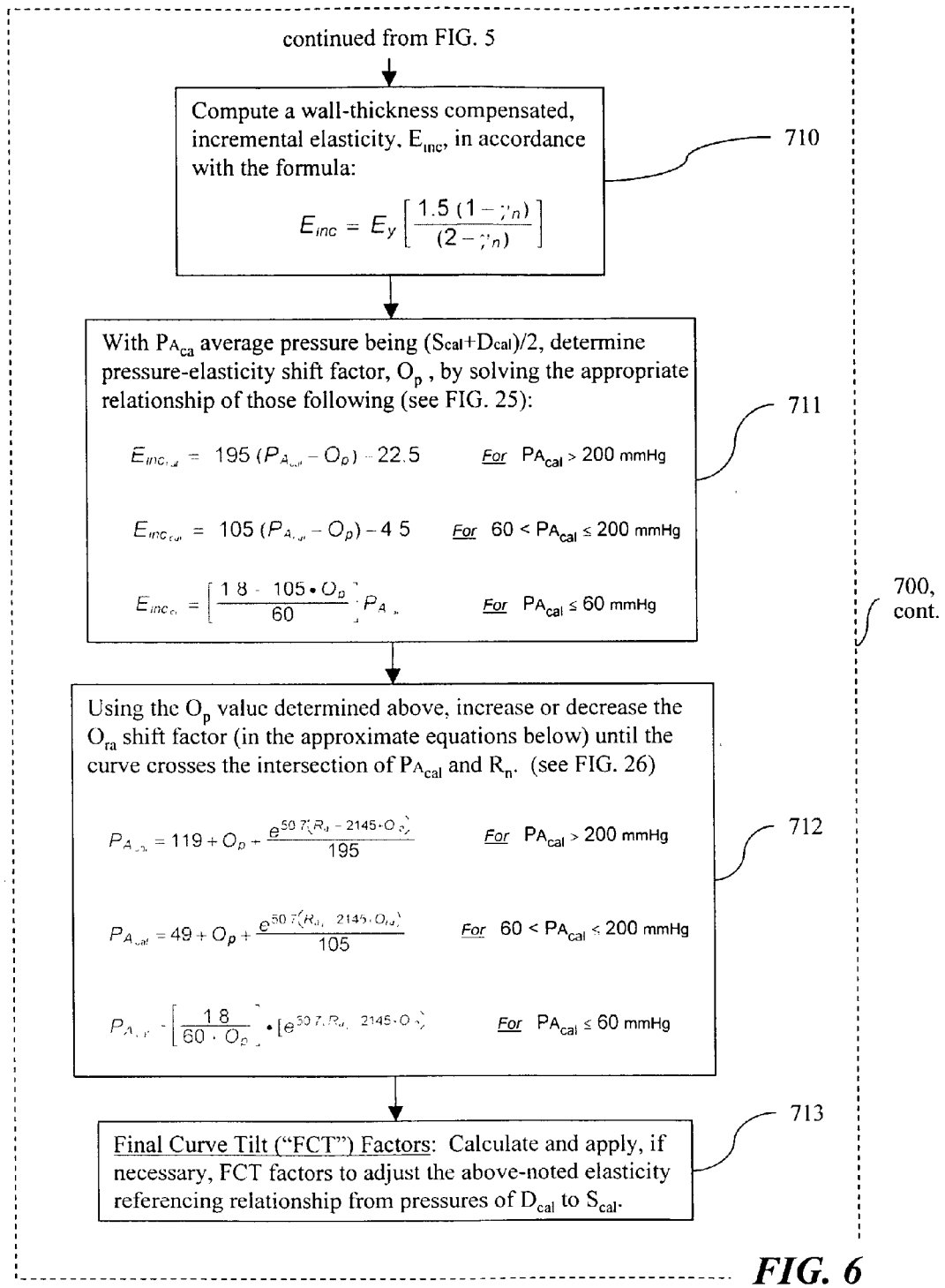
Figure 25:
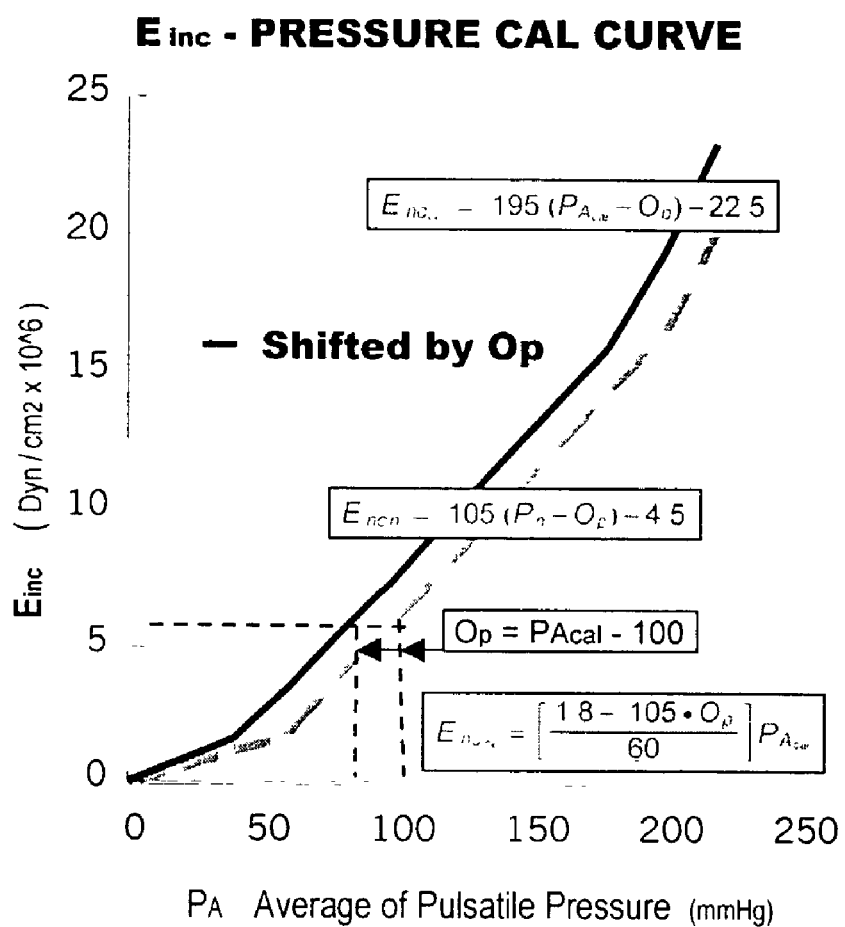
FIG. 25 provides an exemplary illustration of pressure-elasticity referencing, in accordance with the invention.
Figure 26:
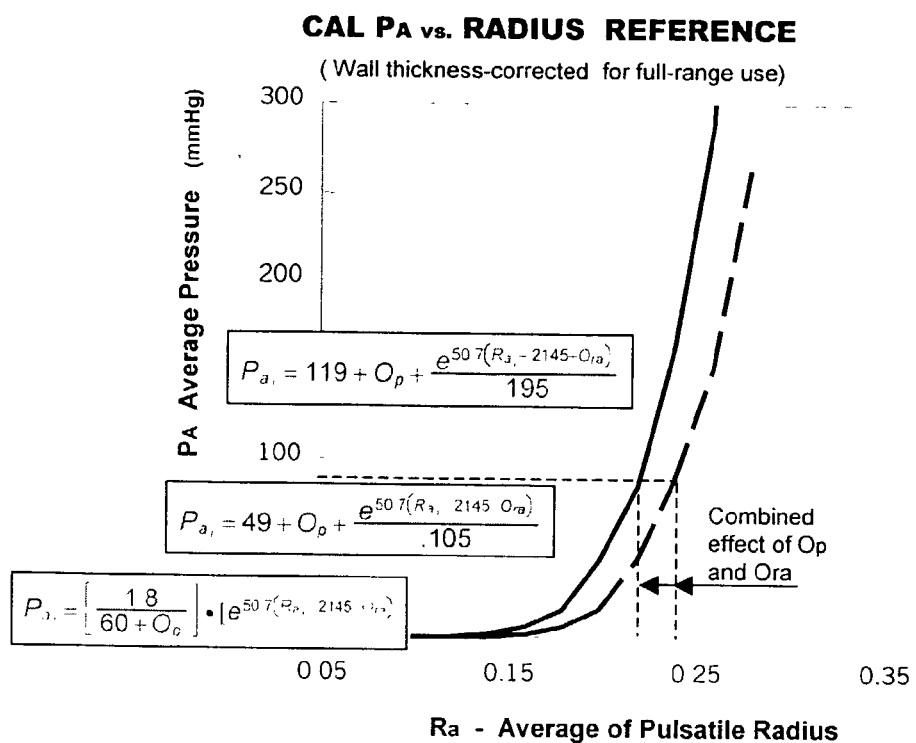
FIG. 26 provides an exemplary illustration of pressure-radius referencing, in accordance with the invention.

Continuing now to FIGS. 5–6, which show a continuation of exemplary process 700, external radius and vda amplitude values are used to determine 705 radial displacement amplitude. Mean radial displacement 706 is calculated using a preselected number of Phase-II heartbeats. Calibration pulse pressure 708 is determined from systolic and diastolic pressures. Young's elasticity 708 and, on FIG. 6, its wall-thickness compensated version 710 are then determined. Calibration pressure-elasticity shift factor is determined in 711, whereby the pressure-elasticity curve 711 is shifted into place as demonstrated in FIG. 25, and calibration radius-average pressure shift factor 712 is determined, whereby the calibration pressure-radius reference curve 712 is shifted into position, as demonstrated in FIG. 26. To the extent that curve 712 does not fit (intersect) the upper and lower pressure 510 and displacement 706 values, final curve tilt factors 713 can optionally be computed to adjust the contour of referencing curve 711, which ends exemplary process 700.

Figure 7:
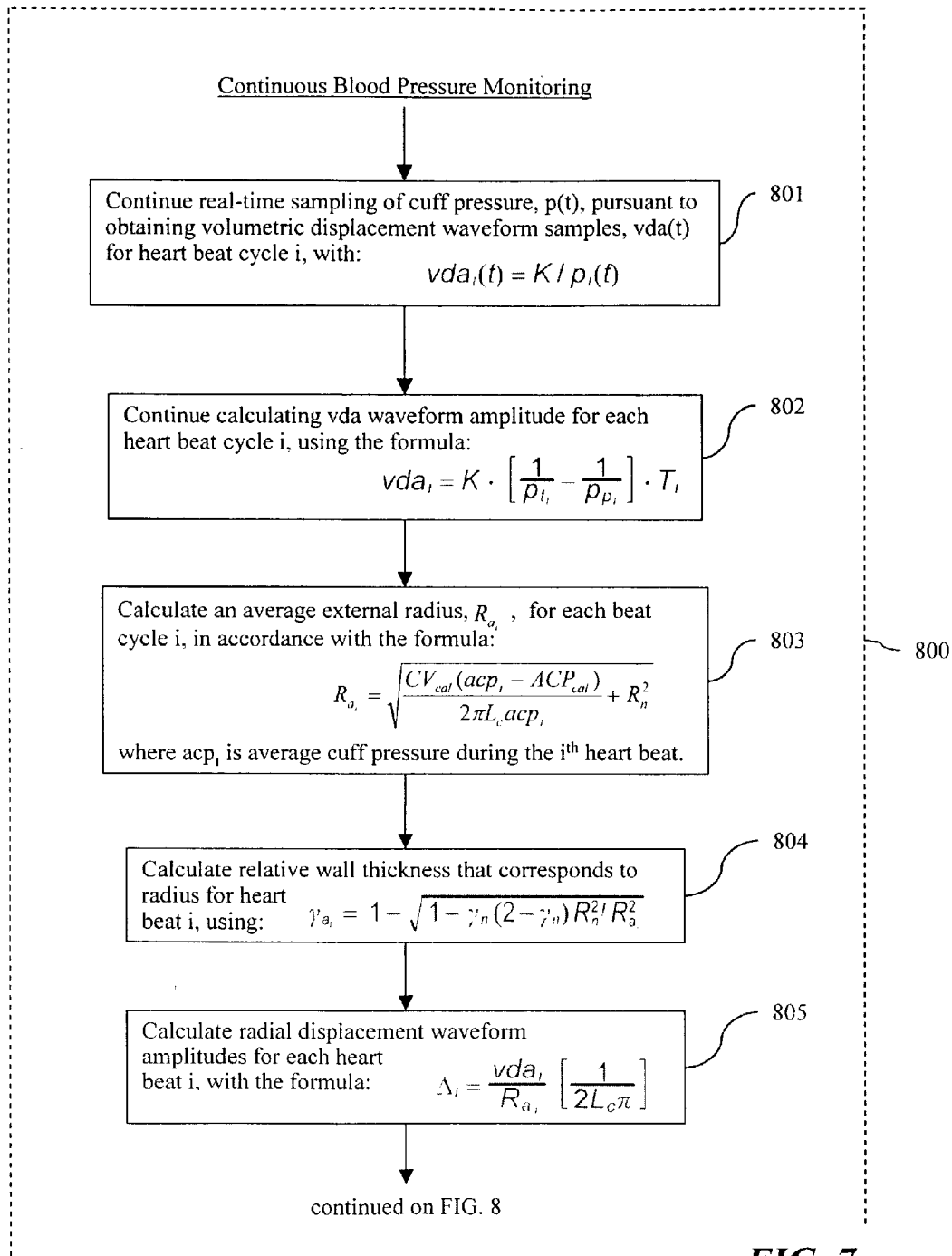
Figure 8:
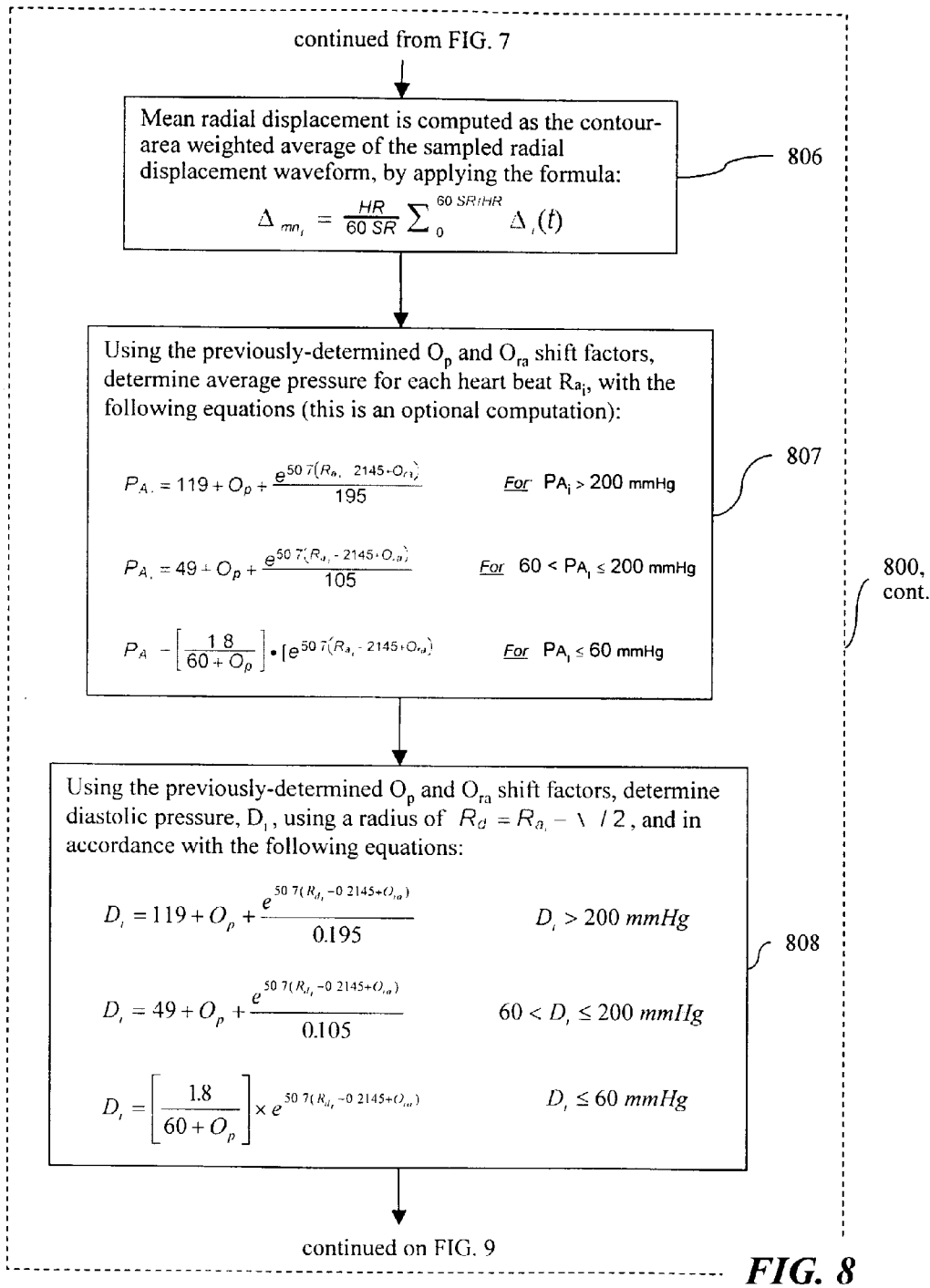
Figure 27:
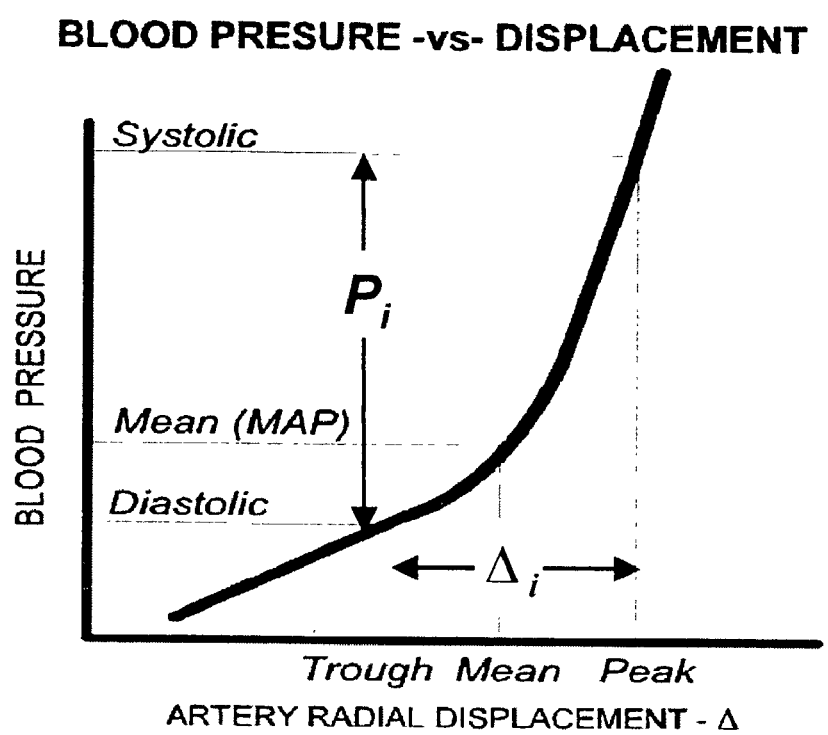
FIG. 27 contains a plot of illustrative blood pressure and radial displacement values.
Figure 28:
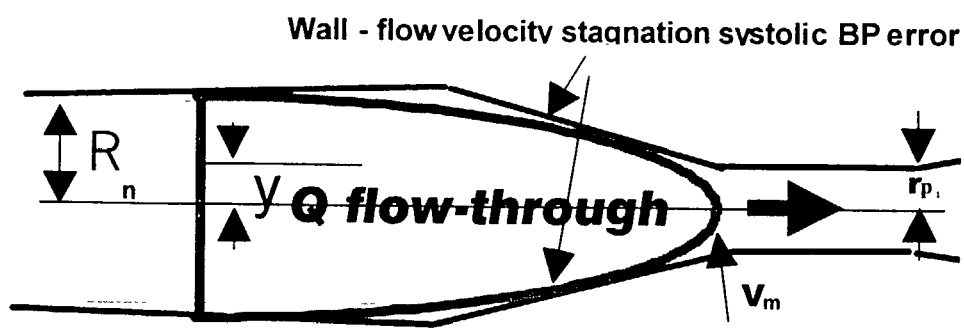
FIG. 28 contains an exemplary graphical artery cut-away to illustrate the effect and computation of elevated flow kinetic energy pressure artifact.

Referring now to FIGS. 7–9, exemplary continuous blood pressure monitoring process 800 begins with continued, real-time determination of vda waveforms 801, from which vda amplitudes 802 are computed for each heartbeat. Process 800 continues with calculation of average external radius 803, radial displacement amplitude 804 and mean radial displacement 805. From these, average blood pressure 807 is optionally determined, and, diastolic 807, systolic 808, and mean pressures 809 are determined. Finally, a pressure sample waveform is created 810 from corresponding displacement samples and three-beat running averages 811 are computed for display. (See also FIG. 27.)

Figure 10:
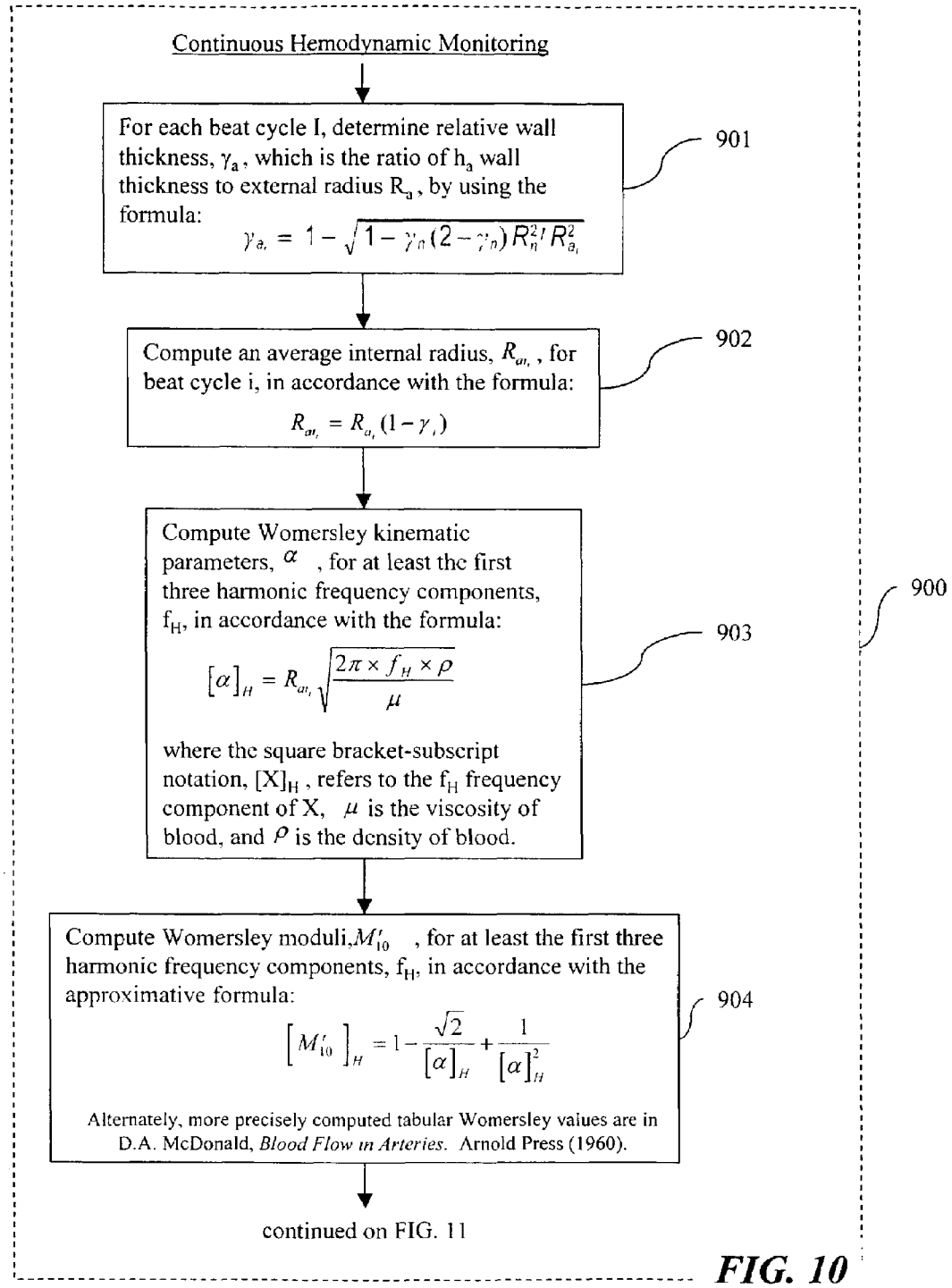
Figure 12:
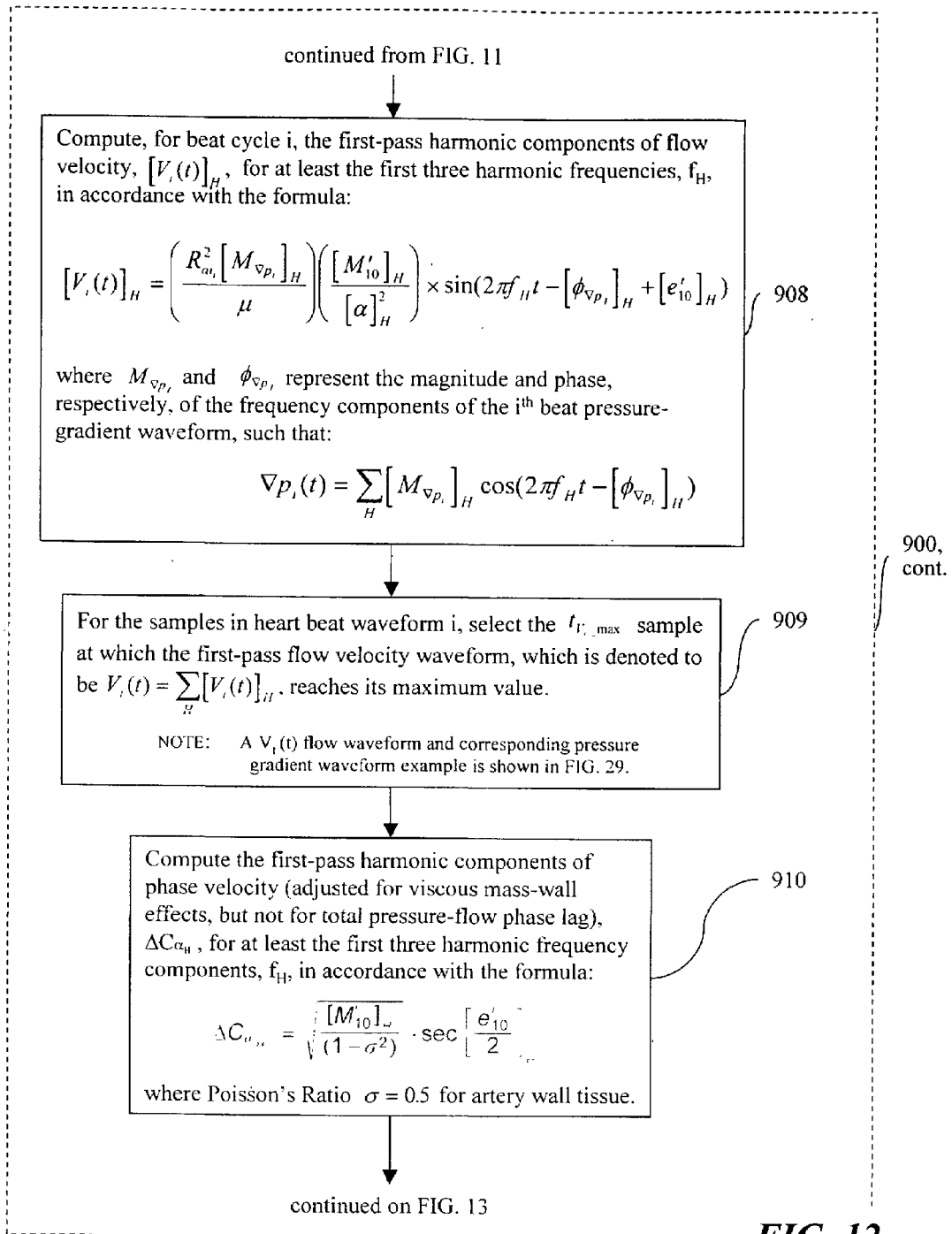

Referring now to FIGS. 10–18, which depict an exemplary continuous hemodynamic monitoring process, exemplary process 900 begins on FIG. 10 by computing relative wall thickness 901 (using average radius 803) and average internal radius 902. Womersley kinematic parameters 903, moduli 904, and phase factor 905 (on FIG. 11) are computed. Group propagation velocity 906 is then computed. FIG. 12 depicts the computation of first-pass pressure gradient waveform 907 and flow velocity waveform 908, the determination of the peak velocity sample 909 of the velocity waveform, and Womersley wall-mass constraint effect 910 is computed for each frequency of interest.

FIG. 13 includes the determination of incremental viscous pressure-flow phase with normalization process 911, and the determination of the peak pulse pressure sample 912 and computed FFT pressure components 913 of the blood pressure waveform 810.

Figure 14:
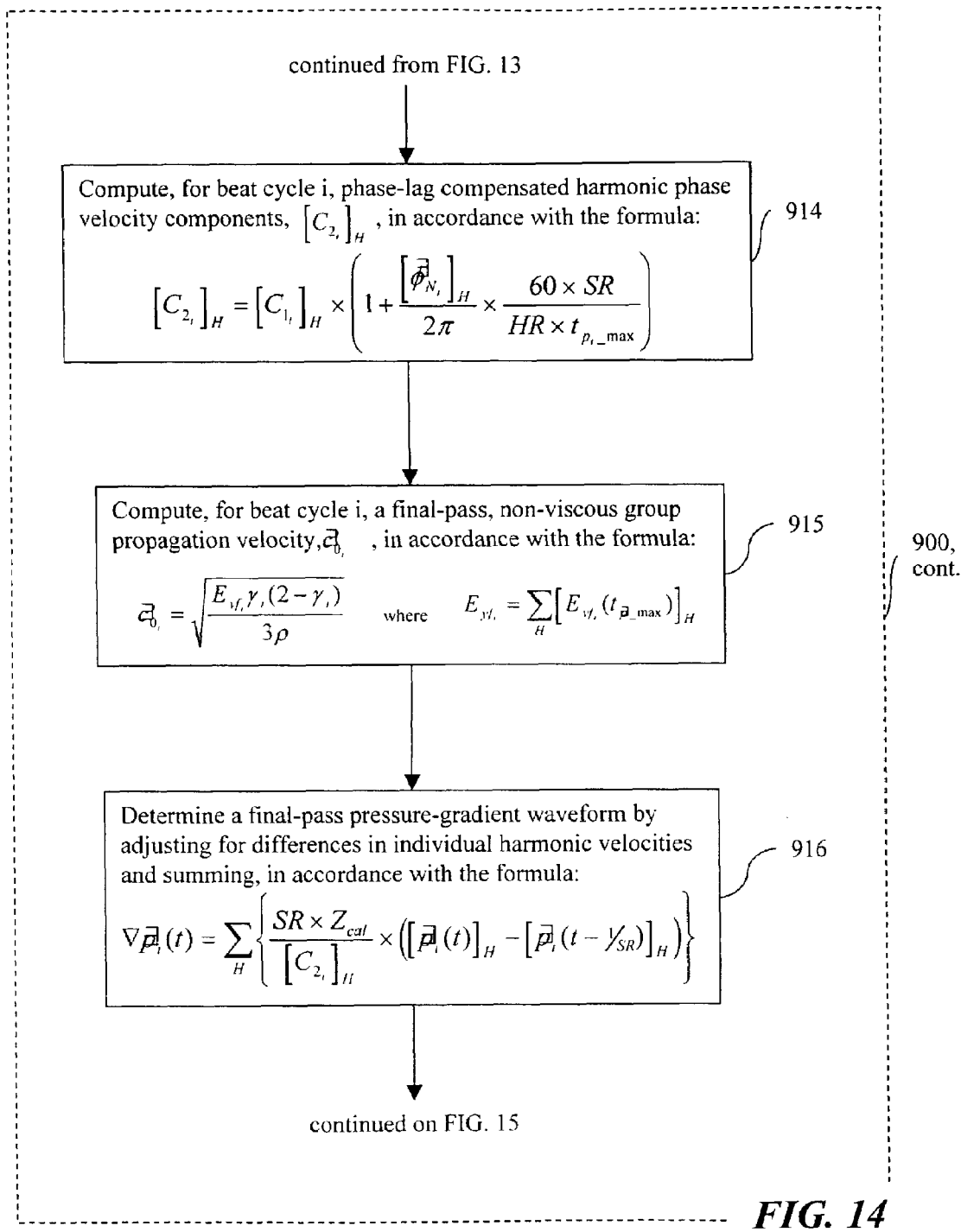

FIG. 14 exemplifies the translation of the normalization phase into phase velocity 914, a group propagation velocity recomputation 915 that adds the effect of the flow-based elasticity harmonic value 911 for the current beat, and a final-pass pressure gradient waveform 916 that is reconstituted from individual pressure harmonics 913 and corresponding harmonic phase velocities 914. FIG. 15 is the final pass FFT harmonic flow velocity waveform component computation 918 (based on gradient waveform 917), and a determination of the composite flow waveform and its normalization-adjusted peak sample identification 919.

Figure 17:
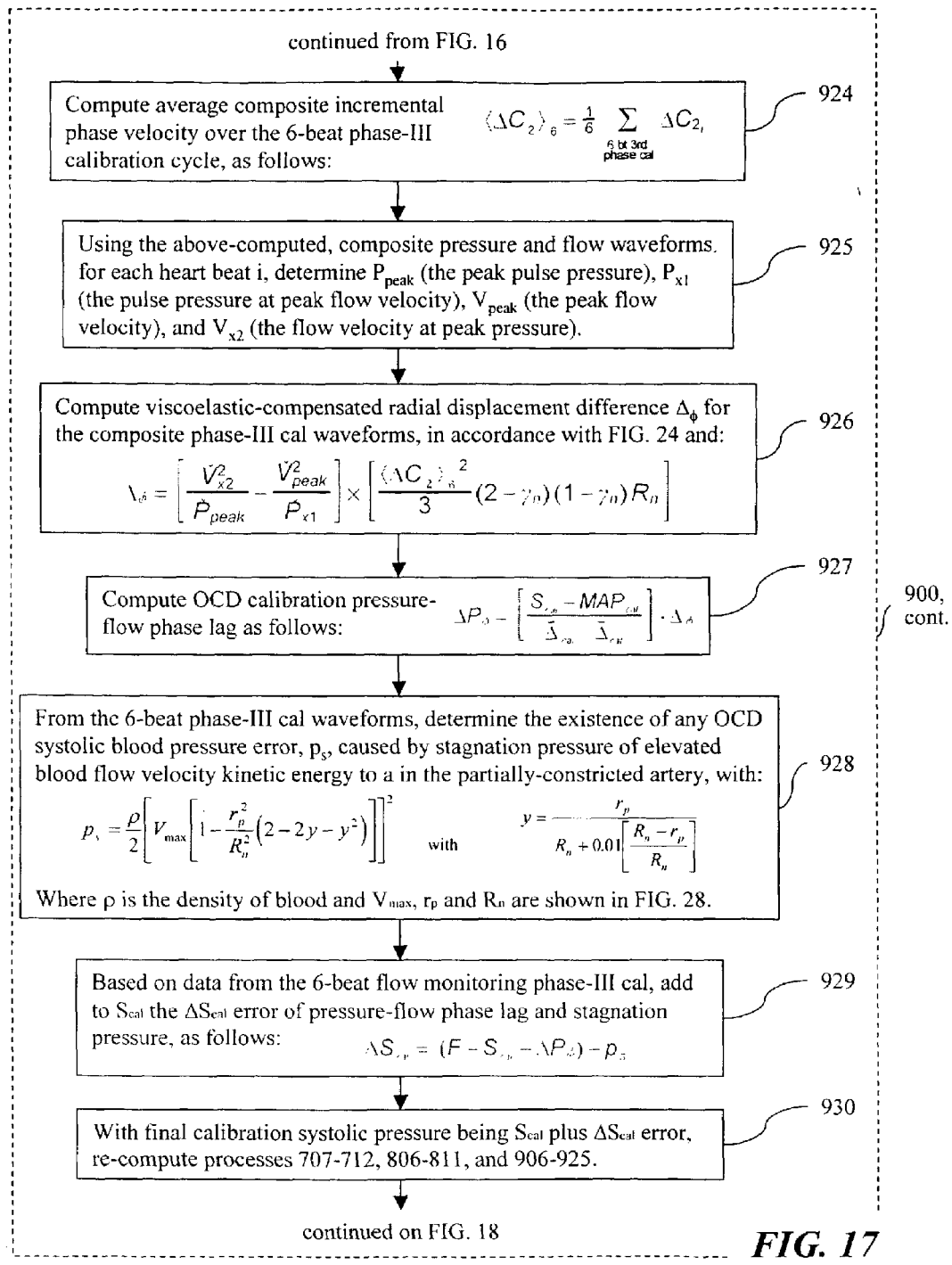

FIG. 16 illustrates the determination of final-pass incremental viscous pressure-flow phase with normalization process 920, which should be not significantly different from 911, and weighted final-pass composite flow-based elasticity 922, which should be not substantially different than 709. Also, mean flow velocity 921 is computed from the flow waveform samples. Still further, for a six-beat phase-III calibration phase, average pressure and flow waveforms 923 and composite phase velocity 924 on FIG. 17 are computed so that pressure and flow velocity peak counterparts 925 and flow-pressure radial displacement difference 926 can be determined for use in 709. Alternately, process 926 can be computed individually on six waveforms, with an average computed thereof, and on an ongoing beat-by-beat basis after calibration, for use by 709. Also on FIG. 17, pulse pressure effect 927 of radial displacement 926, elevated flow velocity stagnation pressure error 928 and total OCD systolic calibration correction 929 are determined, whereupon a recomputation of calibration processes 930 is performed.

Figure 18:
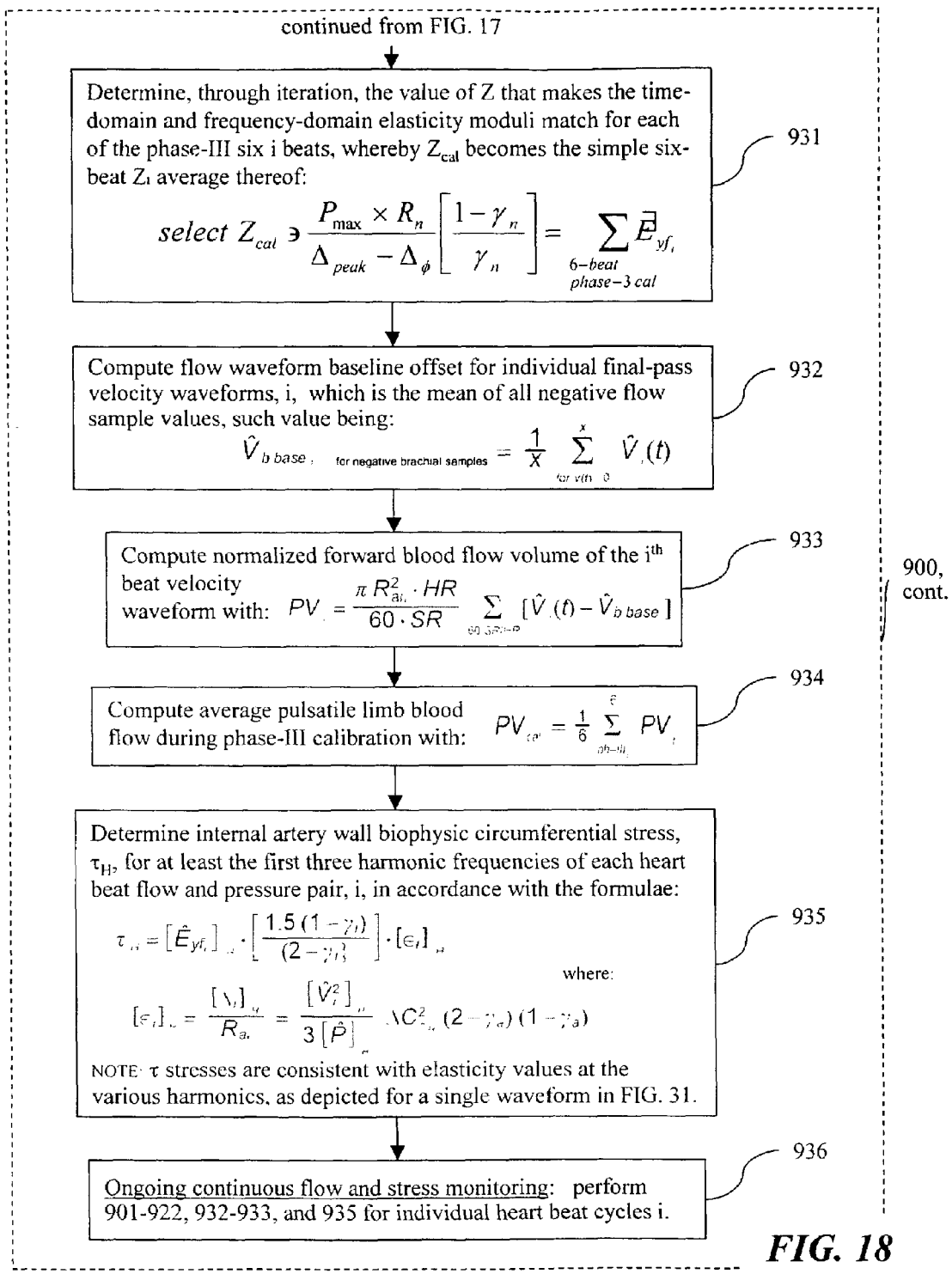

FIG. 18 encompasses an optional calibration computation of pressure gradient sample length 931, monitoring of blood flow velocity waveforms 936, and determination of baseline flow waveform values 933 and 934 and harmonic biophysic cardiovascular stress values 935.

Figure 18A:
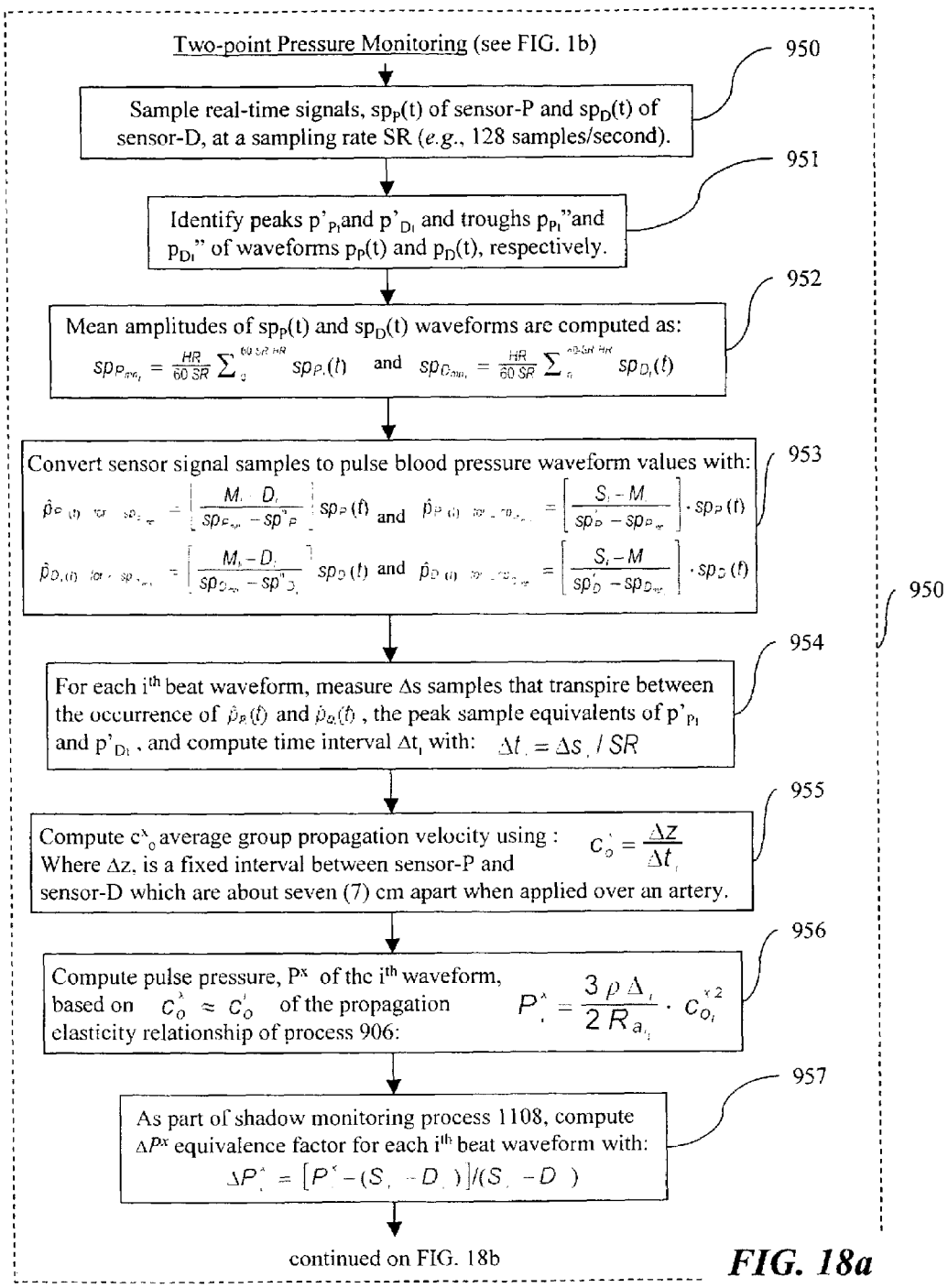

FIG. 18a's Two-Point Pressure Monitoring is the process by which sensor-P and sensor-D waveform samples are converted to separate pressure waveforms to measure group propagation velocity, whereby the propagation-elasticity relationship enables computing a second pulse pressure for the same heart beat cycle. This provides a largely independent parameter for Shadow Monitoring (see below) to compare with the single-point pulse pressure values that are computed in process 807 and 808.

Referring now to FIG. 18b, which shows a continuation of exemplary process 950, Two-point Flow Monitoring FFT processing of sensor-P and sensor-D pressure waveforms enables determining individual harmonic phase shifts and velocities, whereupon a second, largely independent pressure gradient and FFT flow waveform are also derived. This simultaneous flow processing is also performed for reliability assessment by a Shadow Monitoring function.

Figure 19:
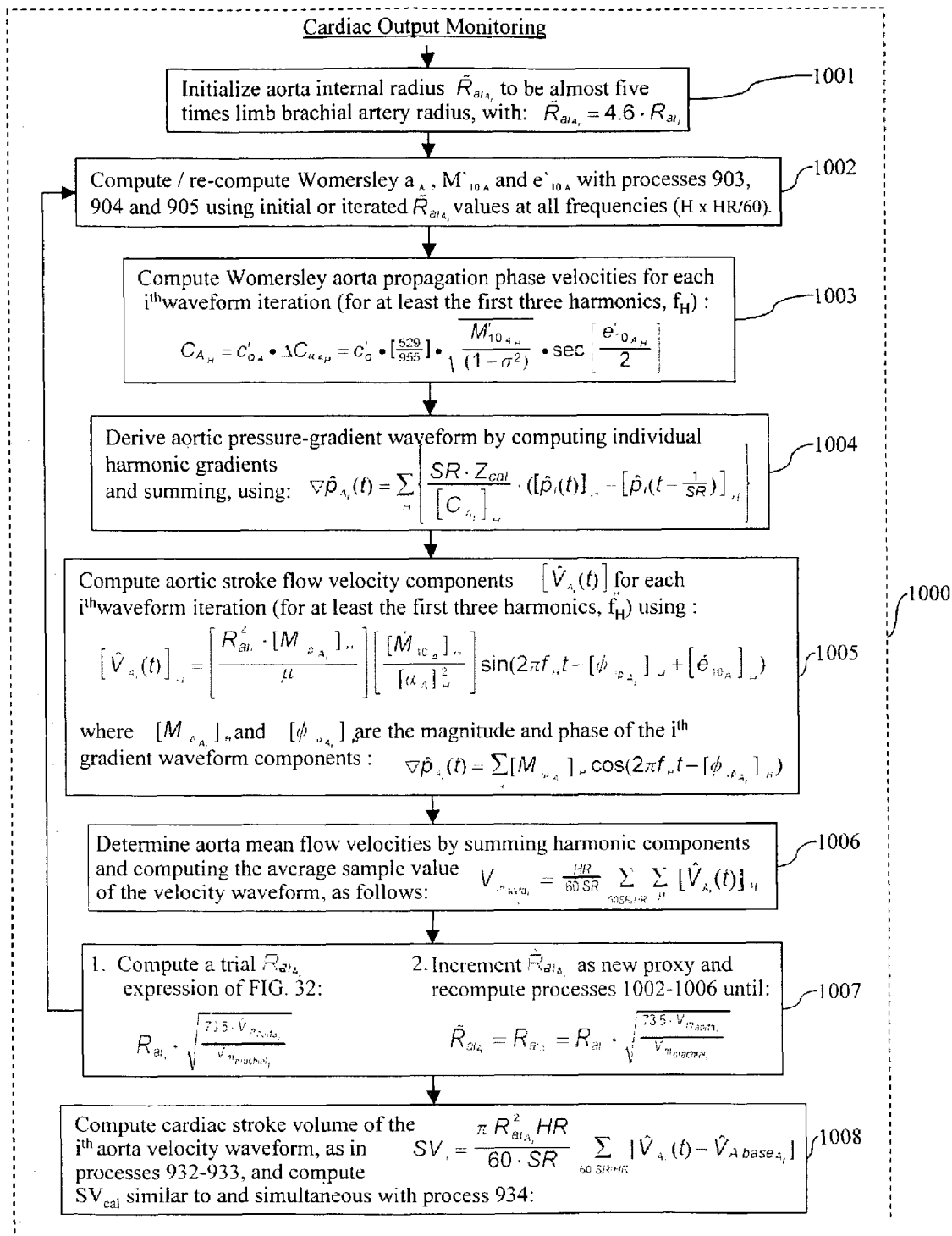
FIG. 19 displays an exemplary flowchart of a Cardiac Output Monitoring process, in accordance with the invention.

FIG. 19 exemplifies a Cardiac Output Monitoring process 1000 by the Flow Continuity Method, which begins with computing a trial aorta radius 1001 whereby process 1002 Womersley kinematic, modulus and phase parameters can be computed, such that propagation phase velocities 1003, aortic pressure gradient 1004, flow velocity harmonic components 1005 and flow velocity waveform and mean flow velocity 1006 can be computed. Process 1007 mean flow continuity test computes a mean flow velocity proxy radius value that is then assigned to be a new trial aorta radius value so that processes 1002–1006 can be completed again, and whereby 1007 is also continued, whereby processes 1002–1007 are repeated as many times as are necessary until the trial and proxy aorta radii values are close to being equal. Flow continuity is valid when trial and proxy aorta radii values are substantially equal, whereupon cardiac stroke volume of that heart beat is computed in process 1008.

Figure 19A:
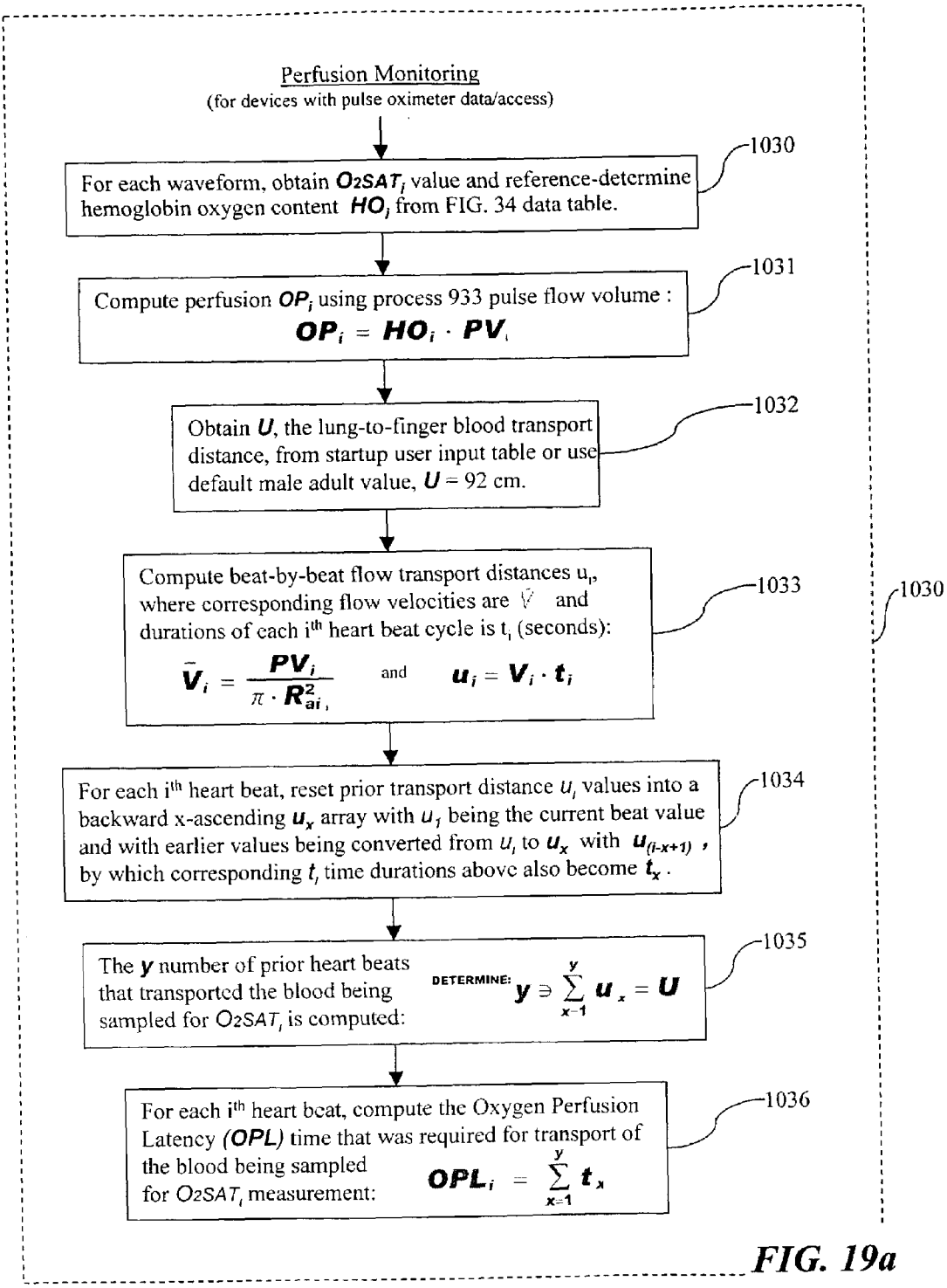
FIG. 19a displays an exemplary flowchart of Oxygen Perfusion and Oxygen Perfusion Latency Monitoring, in accordance with the invention.

FIG. 19a exemplifies perfusion monitoring, a process by which the hemoglobin oxygen saturation content measurements of (a) a noninvasive pulse oximeter, internal or external to the inventive system, with an infrared and red light emitting diode or equivalent sensor applied to the same patient, preferably on the same limb as the sensor that measures blood flow, or (b) a venous oximeter, is transferred to or input into the inventive blood flow system in step 1030, such that the product of said oxygen content and blood flow can be computed in process 1031. It also exemplifies process 1036 computing of perfusion latency of blood transport after oxygenation but before it is measured by oximeter, based on computing the arterial mean blood flow velocities and the transport distance associated with the preceding heart beat blood flows in processes 1032–1035.

Figure 20:
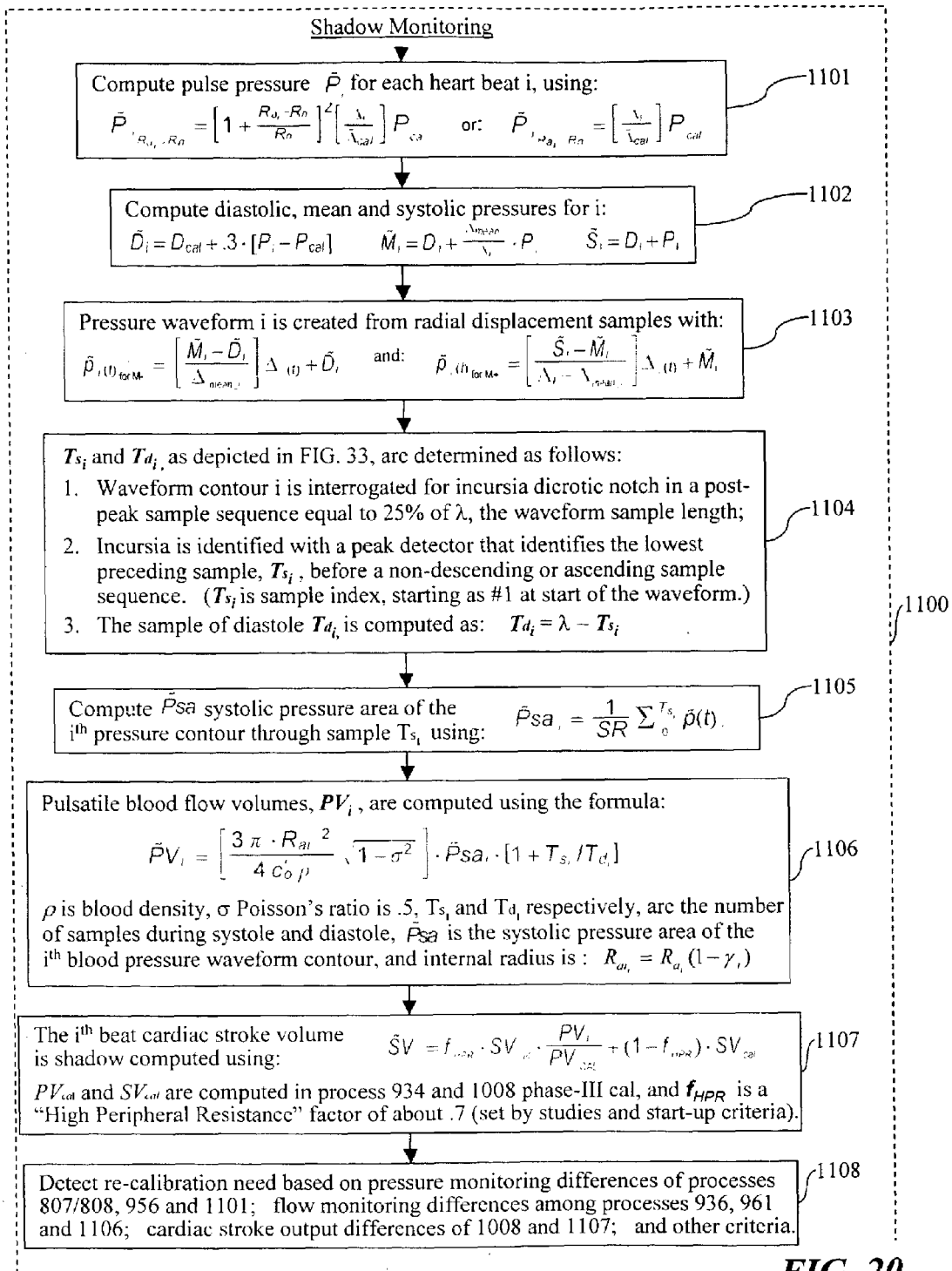
FIG. 20 displays an exemplary flowchart of a Shadow Recal Monitoring process, in accordance with the invention.
Figure 30A:
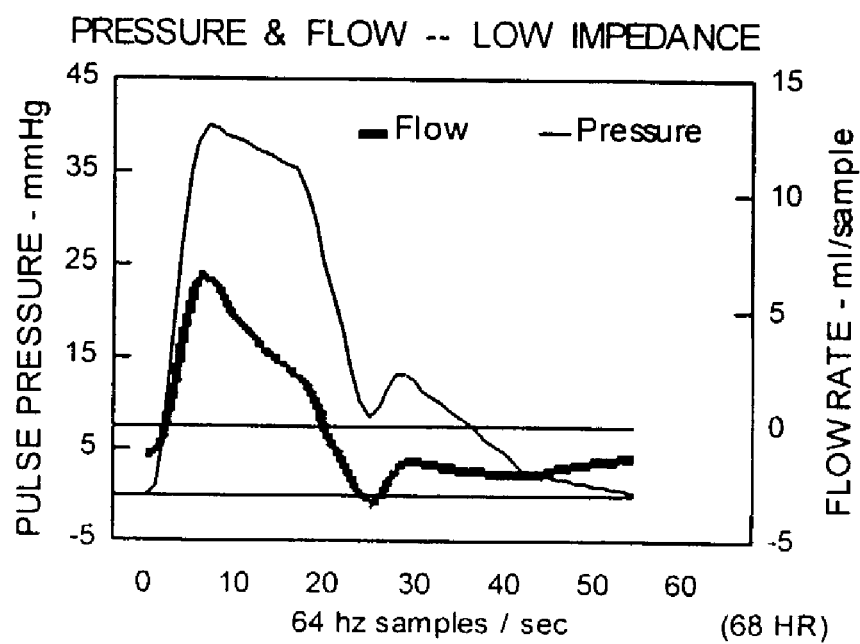
FIGS. 30a through 30d contain plots of flow, pressure and harmonic flow components, for exemplary "low" and "high" impedance examples.
Figure 30B:
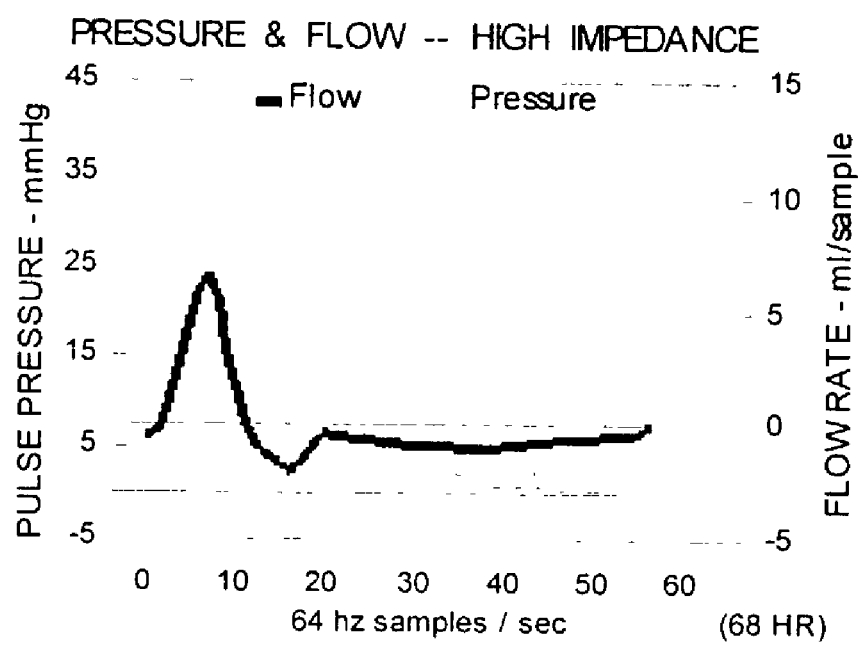
Figure 30C:
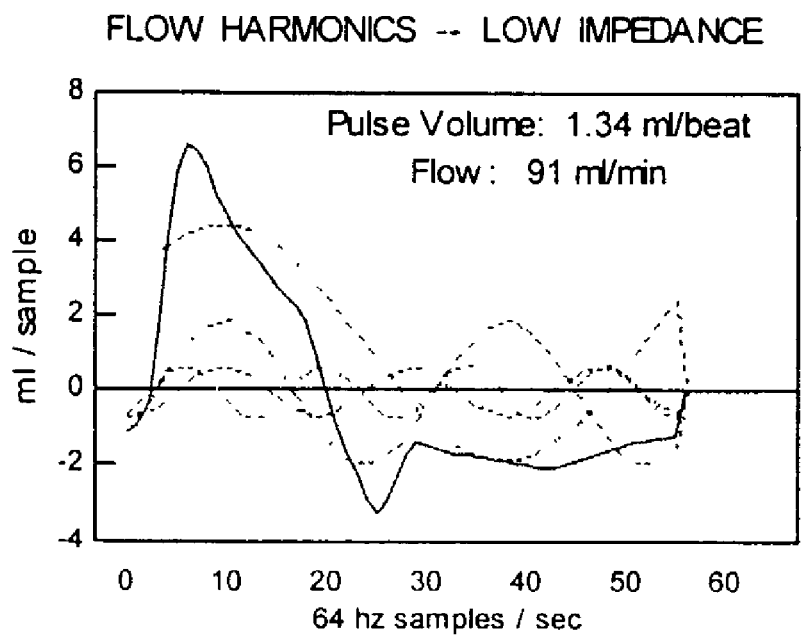
Figure 30D:
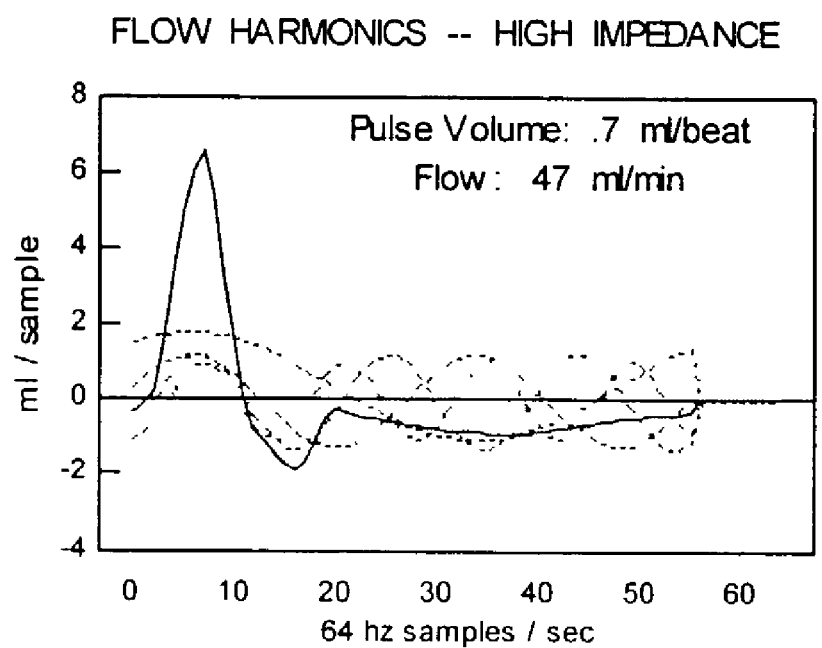
Figure 31:
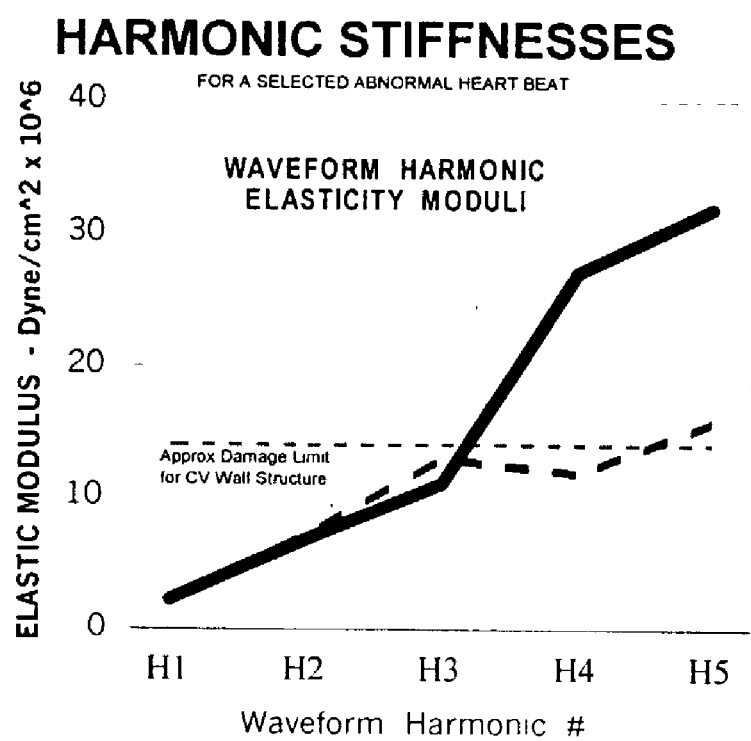
FIG. 31 contains an exemplary graphical illustration of higher frequency elasticity moduli, before and after the determination of viscous flow-pressure phase-shift.
Figure 32:
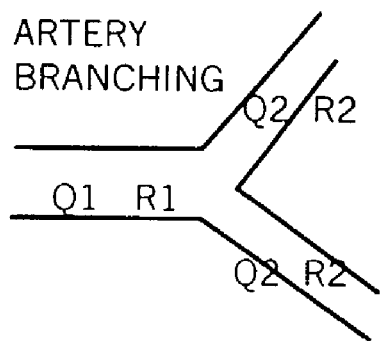
FIG. 32 contains an exemplary conduit flow branching diagram to illustrate the exemplary flow continuity concept.
Figure 33:
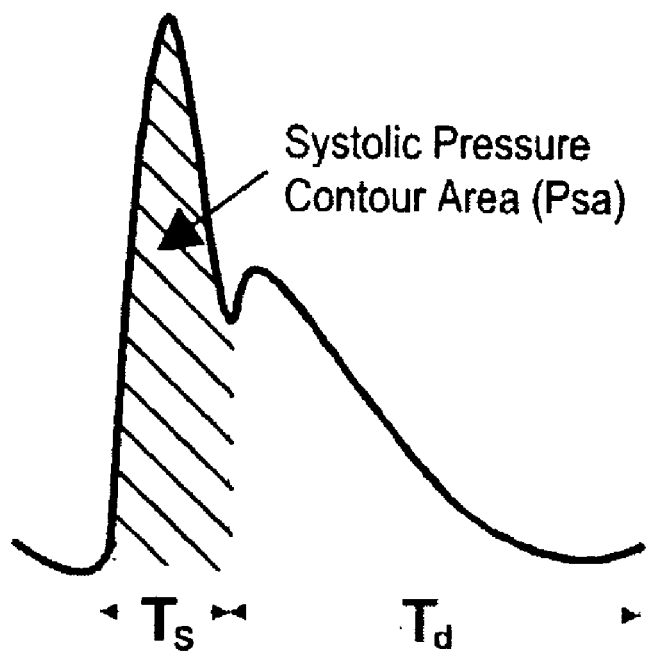
FIG. 33 contains an exemplary pressure waveform, graphically illustrating the shadow monitoring computation of the water-hammer blood flow method.
Figure 34:
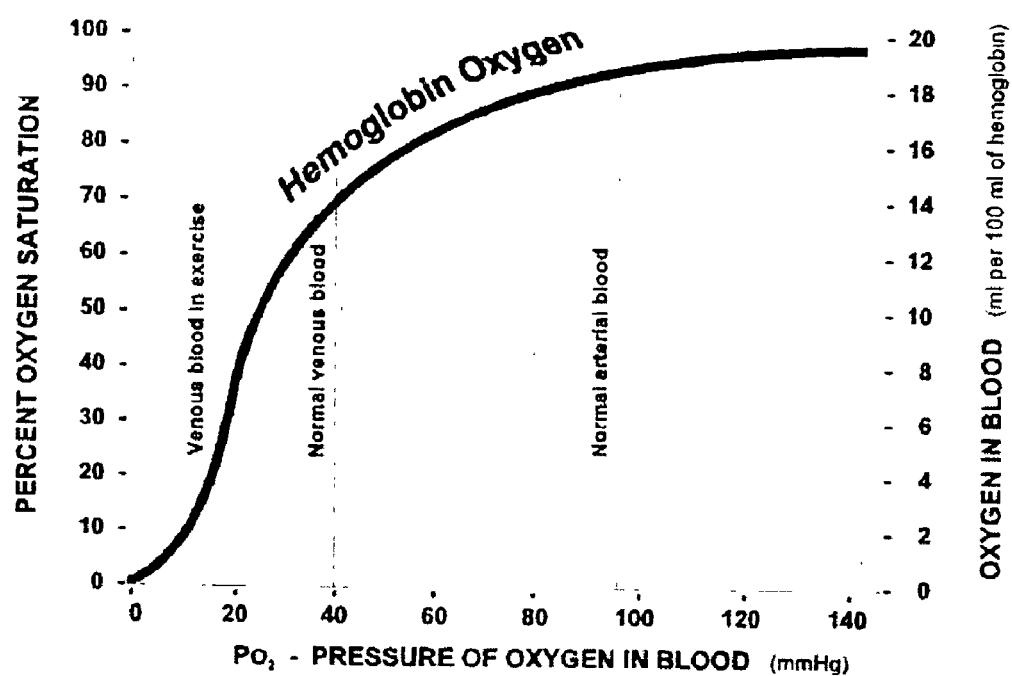
FIG. 34 contains an exemplary graphical reference for converting from pulse oximeter percent saturation to volume of hemoglobin oxygen concentration Symbols that appear in the drawings are defined as follows.

Referring now to FIG. 20, exemplary Shadow Monitoring process 1100, a process for determining need for recalibration for enhanced patient monitoring reliability, pulse other blood pressures are computed in 1101 through 1103. Also, pressure waveforms (see FIGS. 30a, 30b and 33 for examples) are processed to determine systolic and diastolic portions 1104 and systolic pressure contour area 1105, illustrated in FIG. 33. With this and other previously-computed flow parameters, pulsatile blood flow volume 1106 is estimated on a continuous beat-by-beat basis. Cardiac output stroke volume changes 1107 are also shadow monitored on a beat-by-beat estimation basis, based on changes in high resistance blood flows 934 (relative to a phase-III calibration baseline 6-beat average value). Trending differences among blood pressure and flow parameters are continuously computed and various predetermined physiologic criteria are applied in process 1108, as a basis for initiating recalibrations.

While the present invention has been described by illustrative reference to various features and aspects thereof, those skilled in the art will appreciate that no particular aspect or feature of the invention should be considered "essential"—unless expressly set forth in the claims that follow. Those skilled in the art will further appreciate that the claims below, most of which call (at least in part) for some sort of computer implementation, execution and/or realization, should be construed broadly to include, cover and/or refer to any sort of programmable device(s) whatsoever, including, but not limited to PCs, CPUs, minicomputers, servers, mainframe computers, PDAs, embedded controllers, intelligent terminals, distributed or network-based computers, and computers based on unconventional architectures (e.g., neural networks, data-flow machines, massively parallel machines). Therefore, the invention should not be limited to, or defined by, the specific apparatus, methods, and articles-of-manufacture described herein, but rather by the appended claims, which are intended to be construed in accordance with well-settled principles of claim construction, including, but not limited to, the following:

Limitations should not be read from the specification or drawings into the claims (e.g., if the claim calls for a "chair," and the specification and drawings show a rocking chair, the claim term "chair" should not be limited to a rocking chair, but rather should be construed to cover any type of "chair").

The words "comprising," "including," and "having" are always open-ended, irrespective of whether they appear as the primary transitional phrase of a claim, or as a transitional phrase within an element or sub-element of the claim (e.g., the claim "a widget comprising: A; B; and C" would be infringed by a device containing 2A's, B; and 3C's; also, the claim "a gizmo comprising: A; B, including X, Y, and Z; and C, having P and Q" would be infringed by a device containing 3A's, 2X's, 3Y's, Z, 6P's, and Q).

The indefinite articles "a" or "an" mean "one or more"; where, instead, a purely singular meaning is intended, a phrase such as "one," "only one," or "a single," will appear.

Where the phrase "means for" precedes a data processing or manipulation "function," it is intended that the resulting means-plus-function element be construed to cover any, and all, computer implementation(s) of the recited "function" using any standard programming techniques known by, or available to, persons skilled in the computer programming arts.

A claim that contains more than one computer-implemented means-plus-function element should not be construed to require that each means-plus-function element must be a structurally distinct entity (such as a particular piece of hardware or block of code); rather, such claim should be construed merely to require that the overall combination of hardware/software which implements the invention must, as a whole, implement at least the function(s) called for by the claims.

What is claimed is:

1. A noninvasive method of estimating blood flow, comprising:
   noninvasively obtaining a pulsatile signal indicative of pressure pulsations in a patient's artery;
   using said pulsatile signal to compute a longitudinal pressure gradient waveform;
   computing plural harmonic components of said pressure gradient waveform; and,
   using said plural harmonic components of said pressure gradient waveform to estimate plural harmonic blood flow components.

2. A method, as defined in claim 1, wherein computing plural harmonic components of said pressure gradient waveform involves an FFT process.

3. A method, as defined in claim 2, wherein said pressure gradient waveform is computed, at least in part, by differencing successive samples of said pulsatile signal.

4. A method, as defined in claim 3, wherein said estimated harmonic blood flow components are non-linearly dependent on harmonic frequency-related variables.

5. A method, as defined in claim 3, wherein said estimated harmonic blood flow components are non-linearly dependent on arterial radius-related variables.

6. A method, as defined in claim 3, wherein said estimated harmonic blood flow components are non-linearly dependent on elasticity-related variables.

7. A method, as defined in claim 3, wherein said pulsatile signal is obtained from a pressure cuff.

8. A method, as defined in claim 3, wherein plural pulsatile signals are obtained from plural respective pressure cuffs.

9. A method, as defined in claim 3, wherein estimating plural harmonic blood flow components involves estimating at least three harmonic blood flow components.

10. A method, as defined in claim 3, where said plural harmonic blood flow components are computed at each heartbeat.

11. A method, as defined in claim 1, wherein computing plural harmonic components of said pressure gradient waveform involves a DFT process.

12. A method of estimating blood flow, comprising:
    receiving a pulsatile signal related to pressure pulsations in a patient's artery;
    computing a longitudinal pressure gradient waveform, at least in part from said pulsatile signal;
    computing plural harmonic components of said pressure gradient waveform; and,
    using at least two of said plural harmonic components of said pressure gradient waveform to estimate blood flow.

13. A method, as defined in claim 12, wherein computing plural harmonic components of said pressure gradient waveform involves an FFT process.

14. A method, as defined in claim 12, wherein said pressure gradient waveform is computed, at least in part, by differencing successive samples of said pulsatile signal.

15. A method, as defined in claim 12, wherein said pulsatile signal is received from a pressure cuff.

16. A method, as defined in claim 12, wherein plural pulsatile signals are received from plural respective pressure cuffs.

17. A method, as defined in claim 12, wherein estimating blood flow involves estimating at least two harmonic blood flow components.

18. A method, as defined in claim 12, wherein computing plural harmonic components of said pressure gradient waveform involves a DFT process.

19. Estimating blood flow in a patient's artery using at least the following acts:
    computing a pressure gradient waveform related to longitudinal pressure variations along at least a portion of the patient's artery;
    computing plural harmonic components of said pressure gradient waveform; and,
    using at least two of said plural harmonic components of said pressure gradient waveform to estimate blood flow.

20. Estimating blood flow, using at least the acts of claim 19, wherein said pressure gradient waveform is computed, at least in part, by differencing successive samples of a pulsatile signal generated by sampling pressure pulsations in the patient's artery.

* * * * *